(12) United States Patent
James et al.

(10) Patent No.: US 7,648,962 B2
(45) Date of Patent: Jan. 19, 2010

(54) NATRIURETIC COMPOUNDS, CONJUGATES, AND USES THEREOF

(75) Inventors: Kenneth D. James, Mebane, NC (US); Balasingham Radhakrishnan, Chapel Hill, NC (US); Navdeep B. Malkar, Cary, NC (US); Mark A. Miller, Raleigh, NC (US); Nnochiri N. Ekwuribe, Cary, NC (US)

(73) Assignee: Biocon Limited (IN)

( * ) Notice: Subject to any disclaimer, the term of this patent is extended or adjusted under 35 U.S.C. 154(b) by 0 days.

(21) Appl. No.: 10/999,761

(22) Filed: Nov. 30, 2004

(65) Prior Publication Data

US 2006/0172933 A1    Aug. 3, 2006

Related U.S. Application Data

(63) Continuation-in-part of application No. 10/723,933, filed on Nov. 26, 2003.

(60) Provisional application No. 60/574,436, filed on May 26, 2004, provisional application No. 60/429,151, filed on Nov. 26, 2002.

(51) Int. Cl.
| | |
|---|---|
| *A61K 38/16* | (2006.01) |
| *C07K 14/00* | (2006.01) |
| *A61K 47/48* | (2006.01) |
| *A61K 9/00* | (2006.01) |

(52) U.S. Cl. .......................... 514/12; 530/324; 424/400
(58) Field of Classification Search ........................ None
See application file for complete search history.

(56) References Cited

U.S. PATENT DOCUMENTS

| | | | |
|---|---|---|---|
| 5,108,568 A | 4/1992 | Van Alstine | |
| 5,286,637 A * | 2/1994 | Veronese et al. | ............ 435/183 |
| 5,342,940 A | 8/1994 | Ono et al. | |
| 5,773,581 A | 6/1998 | Camble et al. | |
| 6,162,902 A | 12/2000 | Mischak et al. | |
| 6,506,730 B1 | 1/2003 | Lee et al. | |
| 6,586,396 B1 * | 7/2003 | Seilhamer et al. | ............. 514/12 |
| 6,703,381 B1 * | 3/2004 | Ekwuribe et al. | ........... 514/182 |
| 2003/0060606 A1 | 3/2003 | Ekwuribe et al. | |
| 2003/0069170 A1 | 4/2003 | Soltero et al. | |
| 2003/0153488 A1 | 8/2003 | May et al. | |
| 2003/0162710 A1 * | 8/2003 | Sudoh et al. | ................... 514/12 |

FOREIGN PATENT DOCUMENTS

| | | |
|---|---|---|
| EP | 0 295 679 | 12/1988 |
| WO | 96-21469 | 7/1996 |
| WO | 98-45329 | 10/1998 |
| WO | WO 00/69073 A2 * | 2/2000 |
| WO | WO 00/23034 A3 | 7/2000 |
| WO | WO 00/43034 | 7/2000 |
| WO | 00-69900 | 11/2000 |
| WO | 00-69900 A3 | 11/2000 |
| WO | WO 0071576 A2 * | 11/2000 |
| WO | WO 00/78302 A1 | 12/2000 |
| WO | WO 02/098232 A1 | 12/2002 |
| WO | WO 02/098446 A1 | 12/2002 |
| WO | WO 03/022208 A2 | 3/2003 |
| WO | WO 03/022210 A2 | 3/2003 |
| WO | WO 03/022996 A2 | 3/2003 |
| WO | 2004-011498 A2 | 2/2004 |
| WO | 2004-011498 A3 | 2/2004 |
| WO | 2004-047871 A2 | 6/2004 |
| WO | 2004-047871 A3 | 6/2004 |

OTHER PUBLICATIONS

H.F. Gaertner and R.E. Offord. Bioconj. Chem. (1996) 7(1), pp. 38-44.*
Mehvar, Reza; Modulation of the Pharmacokinetics and Pharmacodynamics of Proteins by Polyethylene Glycol Conjugation; *J. Pharm. Pharmaceut Sci.*; 3(1):125-136; 2000.
Brian D. Condon; Glyceryl *Bis*ether Sulfates. I: Improved Synthesis; JAOCS; 1994; vol. 71, No. 7, pp. 739-741.
Thomas K. Chang et al.; Subtiligase: A tool for semisynthesis of proteins; Proc. Natl. Acad. Sci.; 1994; vol. 91, pp. 12544-12548; Biochemistry, USA.
Kang Choon Lee et al.; Isolation, Characterization, and Stability of Positional Isomers of Mono-PEGylated Salmon Calcitonins; Pharmaceutical Research; 1999; vol. 16, No. 6, pp. 813-818; Plenum Publishing Corporation.
Haeshin Lee et al.; Preparation and Characterization of Mono-PEGylated Epidermal Growth Factor: Evaluation of in Vitro Biologic Activity; Pharmaceutical Research; 2002; vol. 19, No. 6, pp. 845-851; Plenum Publishing Corporation.
Andrea Lucke et al.; Biodegradable poly(D,L-lactic acid)-poly(ethylene glycol)-monomethyl ether diblock copolymers: structures and surface properties relevant to their use as biomaterials; Biomaterials; 2000; 21, pp. 2361-2370; Elsevier Science Ltd.
Jong-Hoon Lee et al.; Polymeric nanoparticle composed of fatty acids and poly(ethylene glycol) as a drug carrier; International Journal of Pharmaceutics; 2000; 251, pp. 23-32; Elsevier Science B.V.

* cited by examiner

*Primary Examiner*—Andrew D Kosar
(74) *Attorney, Agent, or Firm*—Marianne Fuierer; Moore & Van Allen, PLLC

(57) ABSTRACT

Modified natriuretic compounds and conjugates thereof are disclosed in the present invention. In particular, conjugated forms of hBNP are provided that include at least one modifying moiety attached thereto. The modified natriuretic compound conjugates retain activity for stimulating cGMP production, binding to NPR-A receptor, and in some embodiments an improved half-life in circulation as compared to unmodified counterpart natriuretic compounds. Oral, parenteral, enteral, subcutaneous, pulmonary, and intravenous forms of the compounds and conjugates may be prepared as treatments and/or therapies for heart conditions particularly congestive heart failure. Modifying moieties comprising oligomeric structures having a variety of lengths and configurations are also disclosed. Analogs of the natriuretic compound are also disclosed, having an amino acid sequence that is other than the native sequence.

61 Claims, 9 Drawing Sheets

Class 1: Non-hydrolyzable– conjugated drug remains intact

Alkyl inside    PEG inside

Class 2: Micropegylated– alkyl portion cleaved *in vivo*

Class 3: Fully hydrolyzable– entire oligomer cleaved *in vivo*

= Nobex amphiphilic oligomer    = hBNP

Figure 5:
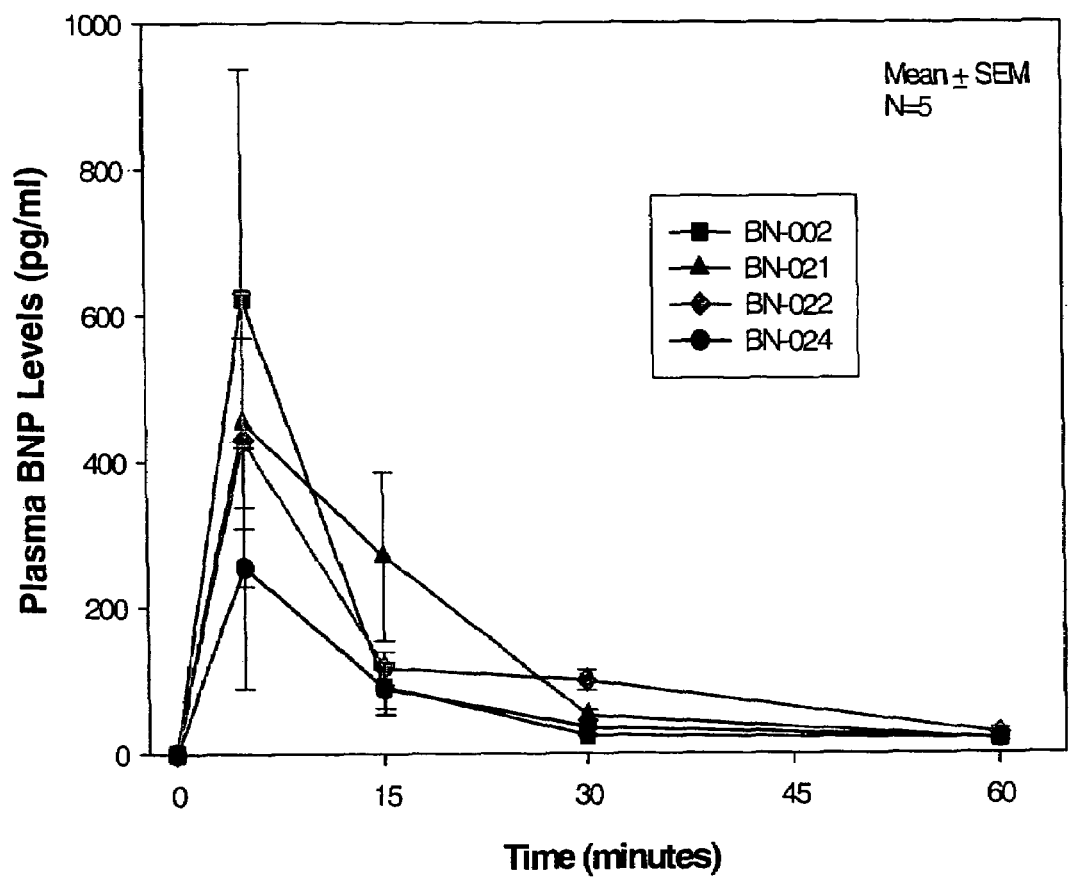
Figure 6C:
Figure 6C:
Figure 6C:
Figure 6C:
Figure 6C:
Figure 6C:
Figure 6C:
Figure 6C:
Figure 6C:
Figure 6C:

Figure 5: Plasma levels of hBNP conjugates at various times after oral dosing.

| NOBEX NUMBER | OLIGOMER STRUCTURE | # OF OLIGOMERS | AVERAGE EC5.0 | STANDARD DEVIATION | AVERAGE Emax | STANDARD DEVIATION | HYDROLYZABLE | n= |
|---|---|---|---|---|---|---|---|---|
| NATIVE BNP LOT UCB 050703 | N/A | N/A | 2.35E-07 | 1.1E-07 | 100.0 | 0.0 | N/A | 4 |
| BN-002 | MPEG$_7$O~~~C(O)~~~PEPTIDE | MONO-1 | 4.44E-07 | 3.0E-08 | 101.0 | 6.8 | NO | 2 |
| BN-002 SCALED UP | MPEG$_7$O~~~C(O)~~~PEPTIDE | MONO-1 | 3.48E-07 | 2.29E-07 | 112.6 | 30.3 | NO | 3 |
| BN-003 | MPEG$_7$O~~~C(O)~~~PEPTIDE | TRI | >1.00E-05 | N/A | <20.0 | N/A | NO | 4 |
| BN-004 | MPEG$_7$O~~~C(O)~~~PEPTIDE | TETRA | >1.00E-05 | N/A | <20.0 | N/A | NO | 2 |
| BN-007 | ( )$_{10}$ PEG$_2$O~~~C(O)~~~PEPTIDE | TRI | >1.00E-05 | N/A | <20.0 | N/A | MICROGYLATED | 2 |
| BN-008 | ( )$_{10}$ PEG$_2$O~~~C(O)~~~PEPTIDE | TETRA | >1.00E-05 | N/A | <20.0 | N/A | MICROGYLATED | 2 |
| BN-010 | PEG$_3$O~~~C(O)~~~PEPTIDE | TETRA | >1.00E-05 | N/A | <20.0 | N/A | MICROGYLATED | 3 |
| BN-011 | MPEG$_7$O~~~C(O)~~~PEPTIDE | MONO-2 | 1.11E-06 | 3.3E-07 | 71.2 | 21.2 | NO | 2 |
| BN-012 | MPEG$_7$O~~~C(O)~~~PEPTIDE | DI | 1.71E-08 | 2.5E-07 | 60.8 | 19.2 | NO | 2 |
| BN-013 | MPEG$_3$O~~~C(O)~~~PEPTIDE | TETRA MPEG 3 OF BN-010 | >1.00E-05 | N/A | <20.0 | N/A | MPEG 3 | 3 |

FIG. 6A

| NOBEX NUMBER | OLIGOMER STRUCTURE | # OF OLIGOMERS | AVERAGE EC50 | STANDARD DEVIATION | AVERAGE Emax | STANDARD DEVIATION | HYDROLYZABLE | n= |
|---|---|---|---|---|---|---|---|---|
| BN-014 | MPEG$_2$O-C(O)-PEPTIDE | TRI MPEG2 OF BN-007 | >1.00E-06 | N/A | 26.5 | 7.4 | MPEG 2 | 2 |
| BN-015 | MPEG$_2$O-C(O)-PEPTIDE | TETRA MPEG 2 OF BN-006 | >1.00E-05 | N/A | <20.0 | N/A | MPEG 2 | 2 |
| BN-016 | MEG-O-C(O)-PEPTIDE | TETRA | >1.00E-05 | N/A | 24.6 | 6.5 | MEG | 2 |
| BN-017 | MEG-O-C(O)-PEPTIDE | PENTA | >1.00E-05 | N/A | <20.0 | N/A | MEG | 1 |
| BN-018 | (-)$_4$-EG-C(O)-PEPTIDE | TETRA | >1.00E-05 | N/A | <20.0 | N/A | NO | 2 |
| BN-019 | (-)$_4$-EG-C(O)-PEPTIDE | PENTA | >1.00E-05 | N/A | <20.0 | N/A | NO | 1 |
| BN-021 | MPEG$_4$O-C(O)-CH(NH-C(O)-OPEG$_4$M)-PEPTIDE | MONO-1 | 3.69E-07 | 2.2E-07 | 91.8 | 1.9 | NO | 2 |
| BN-021 SCALED UP | MPEG$_4$O-C(O)-CH(NH-C(O)-OPEG$_4$M)-PEPTIDE | MONO-1 | 3.45E-07 | 1.2E-07 | 90.1 | 0.0 | NO | 3 |
| BN-022 | H$_3$C-(-)$_4$-C(O)-O-PEG$_7$-O-C(O)-PEPTIDE | MONO-1 | 2.81E-07 | 8.1E-08 | 75.7 | 9.2 | NO | 2 |
| BN-022 SCALED UP | H$_3$C-(-)$_4$-C(O)-O-PEG$_7$-O-C(O)-PEPTIDE | MONO-1 | 4.18E-07 | 7.03E-08 | 81.2 | 12.8 | NO | 3 |
| BN-024 | MPEG$_7$O-C(O)-(-)$_{11}$-PEPTIDE | MONO-1 | 3.21E-07 | 1.8E-07 | 106.2 | 42.7 | NO | 2 |

FIG. 6B

| NOBEX NUMBER | OLIGOMER STRUCTURE | # OF OLIGOMERS | AVERAGE EC50 | STANDARD DEVIATION | AVERAGE Emax | STANDARD DEVIATION | HYDROLYZABLE | n= |
|---|---|---|---|---|---|---|---|---|
| BN-024 SCALED UP |  | MONO-1 | 3.14E-07 | 2.26E-07 | 57.8 | 12.2 | NO | 3 |
| BN-025 |  | DI-1 | >1.00E-05 | N/A | 43.6 | 3.0 | NO | 2 |
| BN-028 |  | MONO-1 | >1.00E-05 | N/A | 28.3 | 2.4 | NO | 2 |
| BN-029 |  | MONO-2 | >1.00E-05 | N/A | 34.0 | 13.3 | NO | 2 |
| BN-030 |  | MONO-2 | 1.26E-07 | 4.7E-08 | 53.6 | 5.6 | NO | 2 |
| BN-033 |  | MONO-1/MONO-2 MIXTURE | 1.38E-07 | #DIV/0! | 81.1 | #DIV/0! | YES | 1 |
| BN-034 |  | DI-MIXTURE | 2.75E-07 | 3.3E-07 | 23.9 | 8.4 | YES | 2 |
| BN-038 |  | DI-MIXTURE | 2.24E-06 | 2.1E-06 | 62.3 | 31.0 | YES | 2 |
| BN-041 |  | MONO-1 | 3.58E-07 | 1.8E-07 | 30.6 | 6.9 | NO | 2 |
| BN-042 |  | MONO-4 | 1.46E-07 | 9.5E-08 | 37.9 | 12.2 | NO | 3 |

| NOBEX NUMBER | OLIGOMER STRUCTURE | # OF OLIGOMERS | AVERAGE EC5.0 | STANDARD DEVIATION | AVERAGE Emax | STANDARD DEVIATION | HYDROLYZABLE | n= |
|---|---|---|---|---|---|---|---|---|
| BN-046 | (MPEG structure) | MONO-1/MONO-2 MIXTURE | 2.45E-07 | 1.2E-07 | 60.6 | 23.6 | NO | 3 |
| BN-047 | MPEG7O-...-PEPTIDE | MONO-1/MONO-2 MIXTURE | 8.15E-07 | 5.5E-08 | 40.2 | 6.6 | NO | 4 |
| BN-048 | OPEG₄M-PEPTIDE | MONO-1 | 6.31E-07 | 6.6E-09 | 98.3 | 9.3 | YES | 2 |
| BN-049 | OPEG₄M-PEPTIDE | MONO-2 | 1.25E-06 | 1.5E-08 | 75.2 | 11.7 | YES | 2 |
| BN-050 | (structure)-PEPTIDE | MONO-1 | 1.71E-07 | 5.2E-08 | 94.4 | 22.9 | NO | 3 |
| BN-050 SCALED-UP | (structure)-PEPTIDE | MONO-1 | 4.33E-07 | 1.5E-07 | 104.6 | 23.2 | NO | 2 |
| BN-051 | (structure)-PEPTIDE | MONO-1/MONO-2 MIXTURE | 5.66E-07 | 2.4E-07 | 106.2 | 16.6 | NO | 3 |
| BN-052 | H₃C-(CH₂)₁₄-PEG₈O-PEPTIDE | MONO-1 | 2.12E-07 | 1.0E-08 | 60.1 | 7.4 | NO | 2 |
| BN-053 | MPEG₃O-PEPTIDE | MONO-1 | 2.65E-07 | 7.39E-08 | 99.0 | 3.6 | NO | 3 |

FIG.6D

NATRIURETIC COMPOUNDS, CONJUGATES, AND USES THEREOF

RELATED APPLICATIONS

This application is based on and claims priority to, U.S. provisional patent application Ser. No. 60/574,436, filed May 26, 2004, pending, entitled "NATRIURETIC COMPOUNDS, CONJUGATES, AND USES THEREOF", which is a continuation-in-part of and claims priority to, U.S. patent application Ser. No. 10/723,933, filed Nov. 26, 2003, pending, entitled "NATRIURETIC COMPOUNDS, CONJUGATES, AND USES THEREOF", which is based on and claims priority to U.S. Provisional Patent Application Ser. No. 60/429,151, filed Nov. 26, 2002, expired. The entire disclosure of each of these applications is incorporated here by reference in its entirety, and the benefit of the filing date of each such patent application is hereby claimed for all purposes that are legally served by such claim.

1. STATEMENT OF GOVERNMENT SUPPORT

The subject invention was made with government support under a research project supported by NIH Grant #1 R43 HL074529-01. The United States government has certain rights in this invention.

2. FIELD OF THE INVENTION

The present invention relates to the field of natriuretic compound conjugates and variant natriuretic compounds, and uses of these in the treatment of congestive heart disease and conditions related to this condition. For example, the compositions of the present invention provide a pharmacologically active natriuretic agent and prodrug that may be used in a formulation suitable for oral, nasal, intravenous, or subcutaneous administration. The invention also provides methods of preparing the natriuretic compound conjugates, compounds, and formulations containing them, as well as methods of using these conjugates and compounds. By way of example, the natriuretic compound conjugates comprise a natriuretic peptide including an NPR-A binding motif, at least one modifying moiety conjugation site, and also include at least one modifying moiety attached to the modifying moiety conjugation site. In some embodiments, the compound conjugates have retained pharmacological activity of the native natriuretic peptide, and have enhanced characteristics, such as improved bioavailability, enhanced resistance to proteolytic activity, and/or prolonged activity in the blood stream. In other embodiments, the compound conjugates are provided as hydrolysable prodrugs, which may have reduced pharmacological activity in the prodrug form relative to the native natriuretic peptide, and upon hydrolysis of the prodrug in vivo, an active natriuretic compound is released.

The present invention is also related to the field of recombinant peptides and proteins, as well as methods for preparing these recombinant peptides and proteins. In particular, analogs of natriuretic peptides and proteins are disclosed herein. The analog natriuretic compounds of the invention may be described in some embodiments as having an amino acid sequence that has at least one substituted amino acid relative to the native sequence of the corresponding natriuretic peptide. In some embodiments, the analog natriuretic compounds of the invention may be described as having a pharmacological activity of native forms of brain-type natriuretic peptides (BNP), especially human BNP (hBNP), urodilatin, canine brain natriuretic peptide (cBNP), atrial natriuretic peptide (ANP), especially human ANP (hANP), dendroaspis natriuretic peptide (DNP), or C-type natriuretic peptide (CNP), particularly human CNP (hCNP).

3. BACKGROUND OF THE INVENTION

Cardiovascular diseases constitute the leading cause of death in the United Sates regardless of gender or ethnicity. Of these diseases, congestive heart failure (CHF) is the only one that is increasing in prevalence (Massie and Shah 1997; Packer and Cohn 1999). According to the American Heart Association, the number of hospital discharges and the number of deaths due to CHF both rose roughly 2.5-fold from 1979 to 1999. Currently, about 5 million Americans have been diagnosed with CHF, and about 550,000 new cases occur annually (American Heart Association 2001). This life-threatening condition is accompanied by great financial impact. In fact, it is the single largest Medicare expense (Kayser 2002). Direct and indirect costs for treating CHF have been estimated as high as $56 billion (Hussar 2002). Hospital expenses for the treatment of HF are more than double those for all forms of cancer combined (O'Connell and Bristow 1994).

CHF is a common cause of death, is accompanied by high indirect costs for treatment, and has a high mortality rate. Once a patient has been diagnosed with CHF, the one-year mortality rate is about 20% (American Heart Association 2001). The probability for readmission for the same condition is very high, and several studies of readmission have recently been performed (Chin and Goldman 1997; Krumholz, Parent et al. 1997; Krumholz, Chen et al. 2000). Readmission rates in excess of 35% within one year of diagnosis are typical (Tsuchihashi, Tsutsui et al. 2001). Such frequent recurrence results in multiple emergency care visits and inpatient hospitalizations (Krumholz, Parent et al. 1997). Multiple hospitalizations and inadequate therapeutics define the current situation faced by those who suffer from CHF.

A recent randomized study indicated that home-based intervention can potentially decrease the rate of readmission, prolong survival, and improve the quality of life for patients with CHF (Stewart, Marley et al. 1999). In an independent study that looked at socioeconomic factors, Tsuchihashi, et. al. concluded that both outpatient and home-based care are needed in order to reduce the mortality rate and lower the overall costs associated with CHF (Tsuchihashi, Tsutsui et al. 2001). Clearly, new therapies with broad application that can be used on an outpatient basis are desperately needed in this growing market.

Brain type natriuretic peptide (BNP) is one of a family of peptides that are involved in cardiovascular, renal, and endocrine homeostasis. It was discovered in 1988 (Sudoh, Kangawa et al. 1988), almost a decade after the discovery of atrial natriuretic peptide (ANP). Although it was first isolated from porcine brain, it is known for its activity at receptors in vascular smooth muscle and endothelial cells. BNP is an endogenous peptide produced by the heart. It is first produced as prepro-BNP and is subsequently shortened twice to the active form, a 32-amino acid peptide with one disulfide bond.

Figure 1:
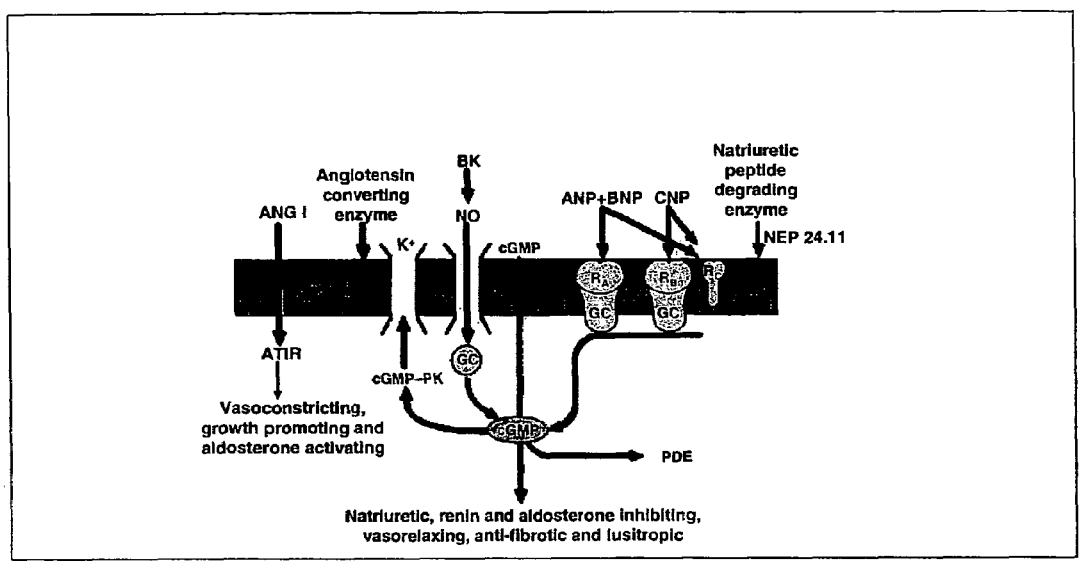

As illustrated in FIG. 1, BNP binds to the natriuretic peptide receptor A (NPR-A), a membrane bound protein on the cell surface. The binding event triggers the synthesis of cGMP in the cytosol by guanylate cyclase. It is through this secondary messenger that BNP accomplishes the cardio-vascular, renal, and endocrine effects with which it is associated. Regulation of BNP is accomplished by several different means. BNP molecules that bind to NPR-A and stimulate cGMP production are removed from circulation, but there are other means by which BNP is eliminated without invoking a response. The most common means of removal is through binding to the clearance receptor, natriuretic peptide receptor C (NPR-C). Upon binding to NPR-C, the peptide is taken into the cell and cleaved enzymatically. The next major means of clearance is degradation by neutral endopeptidase (NEP), which is a membrane-bound enzyme on the cell surface. Finally, BNP is removed to a small extent by renal filtration.

Under normal conditions, BNP is produced in low amounts in the atria and ventricles. However, when the ventricles are stretched during cardiac decompensation, the amount of BNP that is produced increases greatly. Although the atria are still involved, the ventricles become the main site of production. The heart produces BNP in response to a stretching of the ventricles that occurs during decompensation at the outset of CHF. The effects of BNP include natriuresis, diuresis, vasodilation, and a lowering of diastolic blood pressure. These effects are brought about through the actions of a secondary messenger, cyclic guanosine monophosphate (cGMP). Production of cGMP is triggered when BNP interacts with the natriuretic peptide receptor A (NPR-A) which is a membrane-bound receptor located on the surface of endothelial cells in blood vessels, kidneys, and lungs. Plasma concentration of BNP incrementally increases with increased severity of CHF. Despite this increase, the beneficial effects of BNP are blunted in severe CHF, raising the possibility of a relative deficiency state in overt CHF. Alternatively, as the assays currently employed to measure plasma concentration of BNP do not specifically differentiate between pre-pro BNP and the mature form, this pro-hormone may not be adequately processed to its mature form in overt CHF. Therefore, either the amount of BNP that the heart can produce is overcome or prepro-BNP is not adequately converted into its active form, thus reducing its beneficial actions. Because of its early production at the onset of heart disease, BNP has become important as a diagnostic marker to detect patients who are at high risk of developing CHF (Yamamoto, Burnett et al. 1996; McDonagh, Robb et al. 1998; Richards, Nicholls et al. 1998; Nagaya, Nishikimi et al. 2000; Kawai, Hata et al. 2001; Maisel, Krishnaswamy et al. 2002; McNairy, Gardetto et al. 2002).

BNP functions to relieve cardiac decompensation in several ways. As the name implies, BNP leads to the excretion of sodium and an increase in urine output, which lessen congestion. It also functions as a vasodilator, the effects of which are enhanced by several other actions. Most notable of these functions are the roles BNP plays in the interference of the renin-angiotensin-aldosterone system (RAAS). It leads to inhibition of renin, which is a key enzyme in the generation of the vasoconstrictive peptide angiotensin. It inhibits the overgrowth of epithelial cells lining vascular tissue, which left unchecked, can greatly reduce blood flow. A final way that BNP functions to relieve cardiac decompensation is its lusitropic effects. It improves myocardial relaxation of the ventricles, resulting in lower diastolic blood pressure.

Practical limitations exist in using peptides as drugs. Proteolysis, both in the gut and in the bloodstream, is a major barrier to using peptides as therapeutics. Another difficulty encountered with non-endogenous peptides is immunogenicity. As a result of these problems, the approach of the pharmaceutical industry has been to create small, non-peptide molecules using medicinal chemistry. While this approach has met with success, it is costly, time consuming, and fraught with uncertainty in terms of pharmacokinetics and toxicity. Furthermore, identification of small organic molecules with agonist activity at peptide receptors has proved exceptionally challenging.

While the use of "PEGylated" proteins is well established to date, they have been confined to injectable use. The present invention provides orally available conjugates of polypeptides, such as human brain-type natriuretic peptide (hBNP). Specifically, the present invention provides conjugates comprising PAG linked to therapeutic peptides and proteins in a formulation in the treatment of congestive heart failure. These preparations then function to protect the hBNP against proteolytic enzymes, and thereby permit the effective use of this agent as an agonist of human natriuretic peptide receptor A. As a result of this agonistic activity, there is enhanced production of cGMP.

In August 2001, hBNP (native peptide) was approved by the FDA under the trade name Natrecor® (Nesiritide) for the treatment of acute congestive heart failure. Natrecor® was the first drug approved for the treatment of CHF in over twelve years. It is administered by intravenous continuous infusion over a period of 48 hours. As the drug is expensive and requires hospitalization, Natrecor® is only used for the most acute cases. Despite this expense and inconvenience, Natrecor® may be considered less expensive than some other therapies by reducing the amount of time patients spend in intensive care units.

Currently, almost 5 million Americans have CHF and over 550,000 new cases are reported each year (American Heart Association 2001). Currently, direct costs for the treatment of CHF are well over $20 billion (American Heart Association 2001). With diagnostic procedures now available to detect the onset of heart failure before cardiac damage occurs, there is great need for a drug with expanded utility that can be used in an outpatient or home-based setting.

4. SUMMARY OF THE INVENTION

The present invention broadly comprises variant and modified forms of several naturally occurring natriuretic peptides, proteins, analogs, and chemical conjugates of these natiruertic peptides that possess one or more advantages over their naturally occurring counterparts. By way of example, some of these advantages include an increased resistance to proteolytic degradation, an improved time of persistence in the bloodstream, and/or an improved ability to traverse cell membrane barriers.

Natriuretic compound conjugates according to some embodiments of the present invention comprise a natriuretic compound that includes a natriuretic protein receptor A binding motif (an NPR-A), at least one modifying moiety conjugation site, and at least one modifying moiety attached to said modifying moiety conjugation site. By virtue of the modifying moiety attached to said natriuretic compound as part of the conjugate, the natriuretic compound conjugate can have modified hydrophilic characteristics relative to the native natriuretic compound that does not include a modifying moiety as described herein. By way of example and not limitation, and as described more fully herein, the modifying moiety may take the form of an oligomer of any variety of sizes, shapes, substitutions, and configurations.

In some cases, the natriuretic compound conjugate is characterized at least in part by its increased resistance to enzymatic degradation, such as proteolysis, relative to a corresponding unconjugated form of the native natriuretic compound. These compound conjugates may be even further characterized by a retained therapeutically significant percentage of biological activity, such as cGMP stimulating activity, relative to the corresponding unconjugated natriuretic compound. The retained cGMP stimulating activity is typically at least 30%, 40%, 50%, 60%, 70%, 90%, 95%, or even greater than 99% or 100% of the cGMP activity of an unconjugated form of the natriuretic peptide as measured in vitro. Other examples of improved characteristics of the natriuretic compound conjugates of the invention having a modifying moiety, relative to unmodified (unconjugated) natriuretic compound, include improved ability of the natriuretic compound to pass through the GI tract and enter the blood stream; improved hydrophilicity, hydrophobicity, or amphiphilicity of the natriuretic compound; improved solubility of the natriuretic compound in aqueous environments or organic solvents; improved ability of the natriuretic compound to cross cell membranes; improved ability of the natriuretic compound to traverse the blood-brain barrier; improved ability of the natriuretic compound to target a certain receptor, cell, tissue, or organ; and improved pharmacokinetic profile of the natriuretic compound. In a preferred embodiment, the degradation of the biologically active agent component of the natriuretic compound is less than the degradation of unmodified (unconjugated) biologically active natriuretic compound, at a pH of about 2 for less than about 2 hours. The natriuretic compound component of the natriuretic compound can, for example, be more stable as a component of the natriuretic compound conjugates than the unconjugated natriuretic compound in the presence of plasma, proteases, liver homogenate, acidic conditions and/or basic conditions.

Natriuretic peptide conjugates of the invention may induce the anti-hypertensive, cardiovascular, renal, and/or endocrine effects that are associated with the native peptide. In some embodiments, the modification of the natriuretic peptide will protect the peptide, such as hBNP, from proteolysis and facilitate delivery into the systemic circulation through the gut wall, resulting in natriuresis, diuresis, and/or vasodilation. Natriuretic peptide conjugates of the invention can therefore be effectively delivered as an oral formulation (instead of by continuous intravenous infusion for days in a hospital setting). This advantage is expected to reduce hospital costs associated with other CHF therapies by enabling self administration, which has not heretofore been possible, and is expected to expand the therapeutic use of natriuretic peptide, especially hBNP, to include early stage (e.g., class 1) and chronic CHF as well as acute CHF. A preferred embodiment of the present invention is a non-immunogenic peptide conjugate that has increased resistance to degradative enzymes and is suitable for oral delivery and transport across the intestinal epithelium.

The invention also provides several methods for the preparation of the natriuretic compound conjugates. These modifying moieties, can for example, take the form of linear and branched PAG or other polymeric structure.

5. DEFINITIONS

Unless otherwise defined, all technical and scientific terms used herein have the same meaning as commonly understood by one of ordinary skill in the art to which the invention belongs. The terminology used in the description of the invention herein is for the purpose of describing particular embodiments only and is not intended to be limiting of the invention. Headers are used for the convenience of the reader and are also not intended to be limiting of the invention. All publications, patent applications, patents, and other references mentioned herein are incorporated herein by reference in their entirety, as are the package inserts of any branded drugs referred to herein by their brand names.

Singular forms "a", "an", and "the", are intended to include the plural forms as well, unless the context clearly indicates otherwise.

As used in the specification and the claims set forth herein, the following terms have the meanings indicated:

"Amino acid" is defined herein as any naturally occurring, artificial, or synthetic amino acid in either its L or D stereoisomeric forms, unless otherwise specified. The term "residue" is used interchangeably with the term "amino acid", and is often designated as having a particular position in a given sequence of amino acids.

All amino acid abbreviations used in this disclosure are those accepted by the United States Patent and Trademark Office as set forth in 37 C.F.R. § 1.822(b). The following one-letter amino acid designations are used in the description of the present invention. Xaa is used to designate an unknown or undesignated amino acid. The integers above specific residues of the structure provided herein define the residue position number. This residue number is used in conjunction with the one letter amino acid nomenclature, described below, to designate the residue at which a substitution is made in the natriuretic peptide analogs of, for example, hBNP and ANP.

Thus for example, when a mutant hBNP is synthesized in which arginine (R) replaces lysine (K) at residue position number 3 of wild-type hBNP, the nomenclature "BNPK3R" or "hBNP(1-32)K3R" is used. Multiple substitutions are designated in the same manner with a comma separating each substitution as exemplified below.

The term "hBNP(1-32)K3R, K14R, K27R" designates a triple mutant hBNP having that hBNP sequence defined above with the substitution of arginine for lysine at residue position 3 (i.e. K3R), the substitution of arginine for lysine at residue position 14 (i.e. K14R), and the substitution of arginine for lysine at position 27 (i.e. K27R). Other mutants are defined in an analogous manner.

The term "hBNP(1-32)K3R, K14R" designates a double mutant having the lysine replaced with arginine at residue 3 and 14 of hBNP.

| | | |
|---|---|---|
| A = ala = alanine | L = leu = leucine | nle = Norleucine |
| R = arg = arginine | K = lys = lysine | cha = cyclohexylalanine |
| N = asn = asparagine | M = met = methionine | A* = har = hemoarginine |
| D = asp = aspartic acid | F = phe = phenylalanine | orn = ornithine |
| C = cys = cysteine | P = pro = proline | pen = penicillamine |
| Q = gln = glutamine | S = ser = serine | phg = phenyl glycine |
| E = glu = glutamic acid | T = thr = threonine | mpa = mercapto-propionic acid |
| G = gly = glycine | W = trp = tryptophan | a = ala* = D alanine |
| H = his = histidine | Y = tyr = tyrosine | C* = hemocysteine |
| I = ile = isoleucine | V = val = valine | |

"Amphiphilic" means the ability to dissolve in both water and lipids and/or having hydrophilic and lipophilic characteristics, and the terms "amphiphilic moiety" and "amphiphile" mean a moiety which is amphiphilic and/or which, when attached to a polypeptide or non-polypeptide drug, increases the amphiphilicity of the resulting conjugate, e.g., PEG-fatty acid oligomer, sugar fatty acid oligomer.

"Biologically active" refers to an agent having therapeutic or pharmacologic activity, such as an agonist, partial agonist or antagonist.

"Effective amount" as provided herein refers to a nontoxic but sufficient amount to provide the desired therapeutic effect. As will be pointed out below, the exact amount required will vary from subject to subject, depending on age, general condition of the subject, the severity of the condition being treated, the particular biologically active agent administered, and the like. An appropriate "effective" amount in any individual case may be determined by one of ordinary skill in the art by reference to the pertinent texts and literature and/or by using routine experimentation.

"Hydrolyzable" refers to molecular bonds which are subject to hydrolysis under physiological conditions.

"Hydrophilic" means the ability to dissolve in water, and the term "hydrophilic moiety" or "hydrophile" refers to a moiety which is hydrophilic and/or which when attached to another chemical entity, increases the hydrophilicity of such chemical entity. Examples include, but are not limited to, sugars and polyalkylene moieties such as polyethylene glycol.

"Lipophilic" means having an affinity for fat, such as chemicals that accumulate in fat and fatty tissues, the ability to dissolve in lipids and/or the ability to penetrate, interact with and/or traverse biological membranes, and the term, "lipophilic moiety" or "lipophile" means a moiety which is lipophilic and/or which, when attached to another chemical entity, increases the lipophilicity of such chemical entity.

"Lower alkyl" refers to substituted or unsubstituted alkyl moieties having 1, 2, 3, 4, 5, or 6 carbon atoms.

"Monodispersed" refers to a mixture of compounds wherein about 100 percent of the compounds in the mixture have the same molecular weight.

"Pharmaceutically acceptable" with respect to a component, such as a salt, carrier, excipient or diluent of a composition according to the present invention is a component that is compatible with the other ingredients of the composition, in that it can be combined with the natriuretic compound conjugates of the present invention without eliminating the biological activity of the biologically active agent and is suitable for use with subjects as provided herein without undue adverse side effects (such as toxicity, irritation, and allergic response). Side effects are "undue" when their risk outweighs the benefit provided by the pharmaceutical composition. Examples of pharmaceutically acceptable components include, without limitation, any of the standard pharmaceutical carriers such as phosphate buffered saline solutions, water, emulsions such as oil/water emulsion, microemulsions and various types of wetting agents.

"Polyalkylene glycol" or PAG refers to linear or branched polyalkylene glycol polymers such as polyethylene glycol (PEG), polypropylene glycol (PPG), and polybutylene glycol (PBG), and combinations thereof (e.g., linear or branched polymers including combinations of two or more different PAG subunits, such as two or more different PAG units selected from PEG, PPG, PPG, and PBG subunits), and includes the monoalkylether of the polyalkylene glycol. In a particular embodiment, the polyalkylene glycol is polyethylene glycol or "PEG." The term "PEG subunit" refers to a single polyethylene glycol unit, i.e., —($CH_2CH_2O$)—. The term "PPG subunit" refers to a single polypropylene glycol unit, i.e., —($CH_2CH_2CH_2O$)—. The term "PBG subunit" refers to a single polypropylene glycol unit, i.e., —($CH_2CH_2CH_2CH_2O$)—. PAG subunits may also include alkyl side chains, such as methyl, ethyl or propyl side chains.

"Prodrug" refers to a biologically active agent that has been chemically derivitized such that, upon administration to a subject, the prodrug is metabolized to yield the biologically active agent.

"Treat" or "treating" as used herein refers to any type of treatment that imparts a benefit to a subject afflicted with a disease or illness, including improvement in the condition of the subject (e.g., in one or more symptoms), delay in the progression of the condition, prevention or delay of the onset of the disease or illness, enhancement of normal physiological functionality, etc.

6. BRIEF DESCRIPTION OF THE DRAWINGS

FIG. 1—illustrates the mode of action and the regulation of BNP.

Figure 2:
Figure 2:
Figure 2:
Figure 2:
Figure 2:
Figure 2:
Figure 2:
Figure 2:
Figure 2:
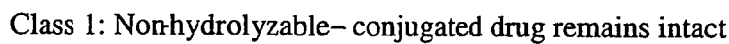

FIG. 2—A representative scheme for oligomer activation and conjugation following a three-tiered conjugation strategy. Class 1 modifying moieties are non-hydrolysable, Class 2 modifying moieties are microPAGylated, and Class 3 modifying moieties are fully hydrolysable.

Figure 3:
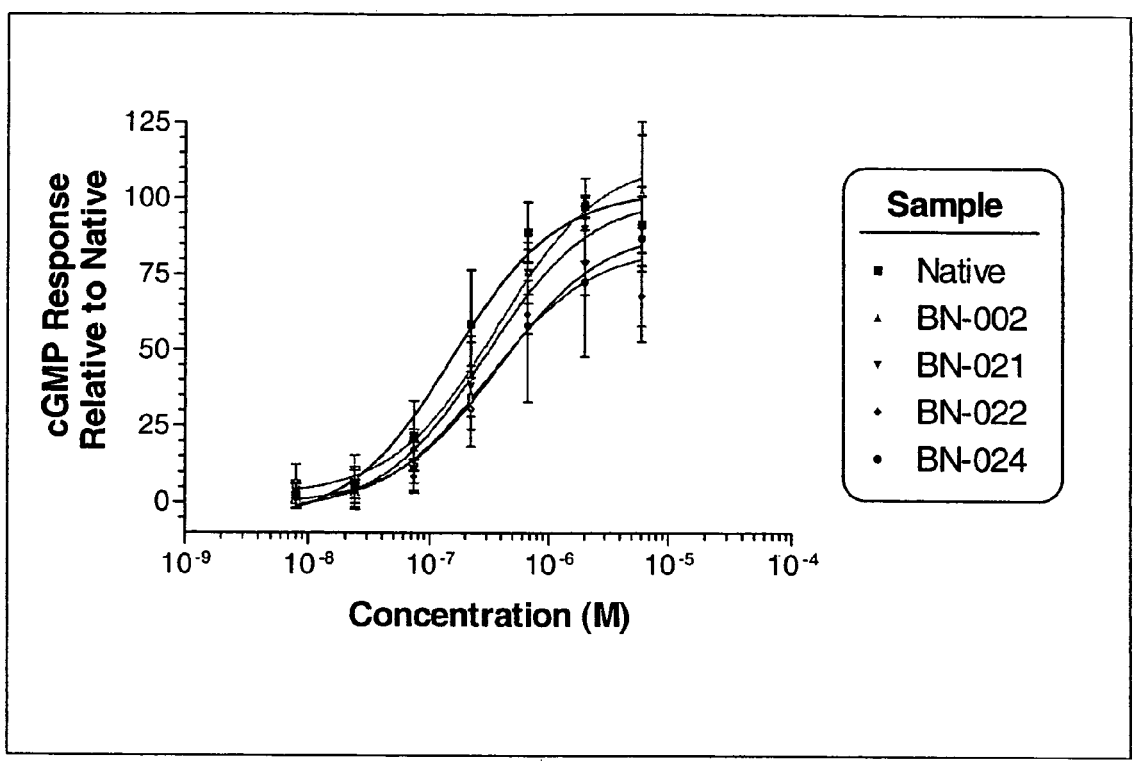

FIG. 3—Cyclic GMP production of HAEC cells as a function of concentration of hBNP or hBNP conjugate. (■=Native, ▲=BN-002, ▼=BN-021, ♦BN-022, ●=BN-024)

Figure 4:
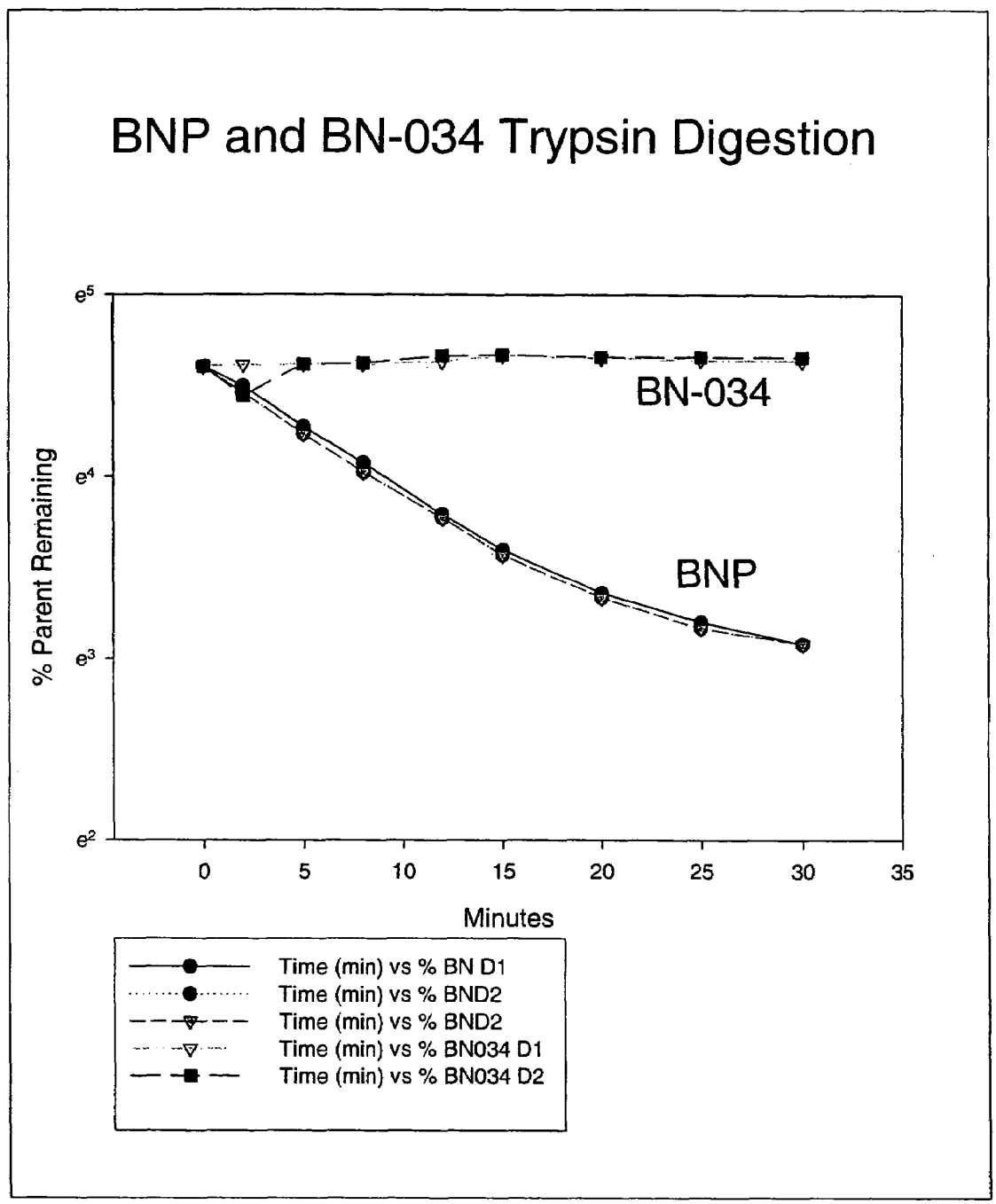

FIG. 4—BNP and BNP conjugate trypsin digestion. (-●-=Time (min) vs % BN D1, •●•=Time (min) vs % BND2, ▼=Time (min) vs % BND2, ▼=Time (min) vs % BN034 D1, ■=Time (min) vs % BN034 D2)

FIG. 5—Plasma levels of hBNP conjugates at various times after oral dosing in rats. (■=BN-002, ▲=BN-021, ♦=BN-022, ●=BN-024)

FIGS. 6A-D—Data showing structure and results of workup for conjugates in Classes 1, 2 and 3.

7. DETAILED DESCRIPTION OF THE INVENTION

Natriuretic compound conjugates according to some embodiments of the present invention comprise a natriuretic compound that includes a natriuretic peptide receptor A binding motif (NPR-A), at least one modifying moiety conjugation site, and at least one modifying moiety attached to said modifying moiety conjugation site. By virtue of the modifying moiety attached to said natiuretic compound as part of the conjugate, the natriuretic compound conjugate can have modified hydrophilic characteristics related to the native natriuretic compound that does not include a modifying moiety as described herein. By way of example and not limitation, and as described more fully herein, the modifying moiety may take the form of an oligomer of any variety of sizes, shapes, substitutions, and configurations.

7.1 Natriuretic Compound

The natriuretic compound conjugates of the invention include a natriuretic compound which includes a binding site for a natriuretic peptide receptor, such as NPR-A, as well as a conjugation site for coupling a modifying moiety thereto.

7.1.1 Native Natriuretic Peptide

The natriuretic compound may have the amino acid sequence of a native natriuretic peptide such as ANP, BNP, CNP or DNP, urodilatin, from any of a variety of species, such as humans, canines, and rats. Preferred native natriuretic peptides are human BNP, rat BNP, canine BNP, or hANP. Native sequences are also intended to include pro-natriuretic peptides and pre-pro peptides.

7.1.2 Natriuretic Compound Analogs

The natriuretic compound may also be a biologically active analog of a native natriuretic peptide (a natriuretic analog). For example, a biologically active analog can be a native natriuretic compound with truncations, deletions, insertions, substitutions, replacements, side chain extensions, and fusion proteins, or combinations of the foregoing which do not eliminate the biological activity of the original compound.

Preferably, the analog will include a native or artificial NPR-A binding motif and will retain some or all of the activity for binding NPR-A.

Natriuretic polypeptide analogs can be obtained by various means. For example, certain amino acids can be substituted for other amino acids in the native natriuretic peptide structure without eliminating interactive binding capacity. In some cases, as have been described in the art, such modifications have resulted in increased affinity for NPR-A, relative to NPR-C, the clearance receptor, resulting in extended half life.

Preferably, the analog will include a natriuretic molecule binding motif, such as an NPR-A binding motif.

The natriuretic peptide may, for example, be defined by the sequence:

```
CFGRXMDRISSSSGLGC,         (SEQ ID NO 1)
``` wherein X is a compound, such as an amino acid residue, including a modifying moiety conjugation site. X in some embodiments comprises an amino acid to which a modifying moiety may attach. For example, X may comprise the amino acid Lys or Cys to which a modifying moiety may be attached. In another embodiment, X may be other than lysine; In these embodiments, the unconjugated peptide is also an aspect of the invention where X is arginine or and amino acid other then lysine to which a conjugation site may be created.

An alternative structure for these embodiments is:

```
CFGRX¹MDRIX²GLGC,          (SEQ ID NO. 2)
``` where $X^1$ is lysine, $X^2$ is one to four amino acids. $X^2$ may be S, SS, SSS, SSSS (SEQ ID NO. 3), K, KS, KSS, or KSSS (SEQ ID NO. 4). Where K is included as $X^2$ or part of the sequences of $X^2$, a modifying moiety conjugation site.

The natriuretic compound may, for example, have the structure:

```
X¹-CFGRX³MDRISSSSGLGC(SEQ ID NO. 5)-X²,
``` wherein at least one of $X^1$ and $X^2$ is present, $X^1$ is a peptide of from 1 to 10 amino acids, wherein $X^2$ is a peptide of 1, 2, 3, 4, 5, or 6 amino acids, and wherein $X^3$ is other than lysine, such as arginine. For example, $X^1$ may include all or a C-terminal fragment of the 1-10 amino acid residue sequence from the N-terminus of hBNP. In one embodiment, $X^1$ includes SPZ¹MVQGSG- (SEQ ID NO: 6), SPZ¹MVQG (SEQ ID NO. 7), SPZ¹MVQ (SEQ ID NO. 8), SPZ¹MV (SEQ ID NO. 9), SPZ¹M (SEQ ID NO. 10), SPZ¹, PZ¹MVQGSG (SEQ ID NO. 11), Z¹MVQGSG (SEQ ID NO. 12), where $Z^1$ is lysine or arginine. Where $Z^1$ is lysine, a modifying moiety conjugation site is provided. In another embodiment, $X^2$ includes all or an N-terminal fragment of the 1-6 amino acid residue sequence from the C-terminus of hBNP. In one embodiment, $X^2$ is sequence Z²VLRRH (SEQ. ID. NO: 13), Z²VLRR (SEQ. ID. NO: 14), Z²VLR (SEQ. ID. NO: 15), Z²VL, K, R, RVLRR (SEQ. ID. NO: 16), RVLR (SEQ. ID. NO: 17), RVL, RV, or R, where $Z^2$ can be lysine or arginine. Where $Z^2$ is lysine, a modifying moiety conjugation site is provided. Where $Z^1$ is lysine, $Z^2$ may be other than lysine, and where $Z^2$ is lysine, $Z^1$ may be other than lysine. Alternatively, $X^1$ and $X^2$ may be any N-terminal and C-terminal tail amino acid sequence obtained from any natriuretic peptide. In some embodiments, an N-terminal and/or C-terminal tail sequence is present and is specifically not the N-terminal and C-terminal tails sequence of hBNP or any fragment thereof. It will be appreciated that the unconjugated natriuretic compound is also an aspect of the invention.

In one embodiment, the natriuretic compound analog comprises an amino acid sequence:

```
X¹MVQGSGC¹FGRX²MDRISSSSGLGC²X³,    (SEQ ID NO. 18)
``` wherein $X^1$, $X^2$ and $X^3$ are each independently selected from the group consisting of Lys and amino acids other than Lys, and wherein at least one of $X^1$, $X^2$ and $X^3$ is Lys and at least one of $X^1$, $X^2$ and $X^3$ is an amino acid other than Lys; and $C^1$ and $C^2$ are cysteines and may be coupled by a disulfide bond. It will be appreciated that the unconjugated peptide analog is also an aspect of the invention.

In one embodiment, at least one of $X^1$, $X^2$ and $X^3$ is Arg. In another embodiment, $X^1$ is Lys, $X^2$ is Arg and $X^3$ is Arg. This embodiment may also include an amino acid sequence as described herein, N-terminal to $X^1$ and/or C-terminal to $X^3$. For example, the N-terminal tail sequence, when present, may be S- or SP-, and the C-terminal tail, when present, may be -VLRRH (SEQ ID NO. 19), -VLRR (SEQ ID NO. 20), -VLR, -VL, or -V. In some embodiments, the N-terminal and/or C-terminal tail sequence is present and is specifically not N-terminal and C-terminal tail of hBNP or a fragment thereof.

In another embodiment, the natriuretic peptide analog includes an amino acid sequence:

```
CFGRX¹MDRISSSSGLGCX²,      (SEQ ID NO: 21)
``` wherein at least one of $X^1$ and $X^2$ is an amino acid comprising a modifying moiety conjugation site coupled to the modifying moiety and the other is any other amino acid or an unconjugated Lys. In one embodiment, $X^1$ is Lys coupled at its side chain to the modifying moiety and $X^2$ is another amino acid, for example Gly or Arg. Alternatively, $X^2$ is Lys coupled at its side chain to the modifying moiety and $X^1$ is another amino acid, for example Gly, Arg, or an amino acid other than lysine. In another embodiment, $X^1$ is Lys coupled at its side chain to the modifying moiety and $X^2$ is an unconjugated Lys. Alternatively, $X^2$ is Lys coupled at its side chain to the modifying moiety and $X^1$ is an unconjugated Lys. It will be appreciated that the unconjugated peptide is also an aspect of the invention.

Virtually any natriuretic peptide may be modified according to the present invention. By way of example peptide/ proteins that are suitable candidates for modification are described in PCTUS0217567, which is specifically incorporated herein by reference. BNP, for example, includes Lys residues in the native sequence that preferably serve as the conjugation sites for the oligomer. In some embodiments of the present invention in which BNP is the native peptide, it may be desirable to remove any conjugation sites from the binding region of the peptide or to eliminate a binding site. Where it is desired that an oligomer not attach at a particular Lys residue of the peptide sequence, the Lys may be replaced with another amino acid, such as arginine. For example, conjugation with non-hydrolysable oligomers in this region can be detrimental to activity, though the applicants have surprisingly discovered that conjugation at $Lys^{14}$ results in a significant amount of retained activity. Thus, it may be desirable to replace such conjugation sites with amino acids that have similar chemical properties but are not readily conjugated. For example, in the hBNP sequence, the $Lys^{14}$ may be substituted with Arg, and thereby favor conjugation of the peptide at the Lys³ of the peptide sequence for native BNP. Amino acid substitutions can be selected to replace Lys with an amino acid that is not readily conjugatable.

In some cases, it may be desirable to add an additional site for conjugation. For example, in some embodiments, a positively charged amino acid residue is replaced with a Lys residue, for example, in the ANP peptide (native sequence), Arg²⁷ can be replaced with Lys.

Mutations to add a conjugation site can be selected so that mutation and conjugation do not eliminate the activity of the resulting peptide conjugate, and in particular it's affinity for NPR-A. In one embodiment, the natriuretic compound is defined as the native hBNP amino acid sequence with one or more Lys residues are inserted within the hBNP sequence and/or added to an end of the hBNP sequence, and/or one or more native Lys residues deleted or replaced with conservative substitutions. Preferably such substitution or insertion is in one or more of the tail amino acid sequences of the natriuretic peptide.

The conjugation site may in some embodiments be inserted, replaced or added at or near the N-terminal tail, e.g., an insertion or substitution within the N-terminal tail amino acid sequence, preferably at the N-terminus, or positioned 1, 2, 3, 4 or 5 amino acids from the N-terminus, or alternatively, positioned 1, 2, 3, 4, 5, 6, 7, 8, or 9 amino acids in an N-terminal direction from the N-terminal Cys that forms a part of the Cys bridge creating the loop. In a preferred embodiment, the natriuretic compound is defined as the native hBNP sequence with one or more mutations selected from the group consisting of $Lys_3 \rightarrow Arg$, $Lys_{14} \rightarrow Arg$, $Arg_{30} \rightarrow Lys$, and $Lys_{27} \rightarrow Arg$, which one or more mutations do not eliminate the biological activity of the natriuretic peptide compound. Addition of more than one modifying moiety, such as an oligomer, may improve enzyme stability and/or enhance absorption.

Many of the natriuretic peptide analogs will include the loop component of a native natriuretic peptide, such as $Cys_{10}$-$Cys_{26}$ of hBNP in which $Cys_{10}$ and $Cys_{26}$ are coupled by a disulfide bond thereby forming a loop. In some cases, the loop may include substitutions, deletions, and/or insertions of amino acids differing from the native sequences, so long as such substitutions, deletions, and/or insertions do not eliminate the activity of the native sequences. Examples of such altered loop sequences can be found in Schoenfelda et al., "Mutations in B-type natriuretic peptide mediating receptor-A selectivity," FEBS Letters 414 (1997) 263-267, the entire disclosure of which is incorporated herein by reference, describes variants of BNP that preferentially bind natriuretic peptide receptor-A (NPR-A) compared to receptor-C (NPR-C). (U.S. Pat. No. 6,525,022 and U.S. Pat. No. 6,028,055). As an example, the natriuretic loop may include a native loop having one or more conservative substitutions which do not eliminate the natriuretic activity of the loop, e.g., in some cases that loop will have the sequence of the native loop (e.g., the native loop of hBNP) and have 1, 2, 3, 4, 5, 6, 7 or 8 conservative substitutions. In another embodiment the loop is shortened by removing a set of amino acids that does not eliminate biological activity. In one embodiment, the peptide analog includes the $Cys_{10}$-$Cys_{26}$ loop of hBNP in which Lys14 is replaced with Gly or Arg. In another embodiment, the SSSS (SEQ ID NO. 3) component of the loop is altered or deleted.

In addition, the natriuretic peptide loops or analogs of the native loops may include an N-terminal tail and/or a C-terminal tail, such as the tails of native natriuretic peptides, e.g., $hBNP_{1-9}$ and $hBNP_{27-32}$. The tails are single amino acids or peptides that do not eliminate biological activity. In some cases, the tails may include substitutions, deletions, and/or insertions of amino acids differing from the native sequences, so long as such substitutions, deletions, and/or insertions do not eliminate the beneficial activity of the native sequences. In one embodiment the tail or tails are based on native sequences, but truncated by one or more amino acids. For example, the N-terminal tail, when present, may selected from the following hBNP segments 8-9, 7-9, 6-9, 5-9, 4-9, 3-9, 2-9, and 1-9; and any of the foregoing segments in which one or more Lys residues is replaced with a Gly or Arg residue. Similarly, a C-terminal tail, when present, may be selected from: hBNP segments 27-28, 27-29, 27-30, 27-31, and 27-32; and any of the foregoing hBNP segments wherein one or more Lys residues is replaced with a Gly or an Arg residue. Examples of preferred loop-plus-tail natriuretic peptides include hBNP segment 1-29; hBNP segment 1-26; and either of the foregoing hBNP segments in which one or more Lys residues are replaced with a Gly or an Arg.

In addition to the foregoing analogs, a wide variety of analogs suitable for use in the invention have been described in the art. For example U.S. Pat. No. 5,114,923, issued May 19, 1992, the entire disclosure of which is incorporated herein by reference, describes a peptide having natriuretic activity of the formula R¹-Cys-Phe-Gly-Arg-Lys-Met-Asp-Arg-Ile-Ser-Ser-Ser-Ser-Gly-Leu-Gly-Cys (SEQ ID NO. 22)-R² wherein R¹ is selected from (H); Gly-; Ser-Gly-; Gly-Ser-Gly-; Gin-Gly-Ser-Gly-(SEQ ID NO. 23); Val-Gln-Gly-Ser-Gly-(SEQ ID NO. 24); Met-Val-Gln-Gly-Ser-Gly-(SEQ ID NO. 25); Lys-Met-Val-Gln-Gly-Ser-Gly-(SEQ ID NO. 26); Pro-Lys-Met-Val-Gln-Gly-Ser-Gly (SEQ ID NO. 27); Ser-Pro-Lys-Met-Val-Gln-Gly-Ser-Gly-(SEQ ID NO. 28); and R³-Ser-Pro-Lys-Met-Val-Gln-Gly-Ser-Gly-(SEQ ID NO. 29) wherein R³ is the 102 amino acid sequence of positions 1-99 for the human protein or a C-terminal portion thereof, and R² is (OH), NH2, NHR' or wherein the modifying moiety' and the modifying moiety" are independently lower alkyl (1-4C) or R2 is Lys; Lys-Val; Lys-Val-Leu; Lys-Val-Leu-Arg (SEQ ID NO. 30); Lys-Val-Leu-Arg-Arg (SEQ ID NO. 31); Lys-Val-Leu-Arg-Arg-His (SEQ ID NO. 32); or the amides ($NH_2$, NHR' or NR' the modifying moiety") thereof.

U.S. Pat. No. 4,904,763, issued Feb. 2, 1990, the entire disclosure of which is incorporated herein by reference, also describes natriuretic peptide analogs suitable for use in the present invention, such as X-Cys Phe Gly Arg Lys Met Asp Arg Ile Ser Ser Ser Ser Gly Leu Gly Cys Lys Val Leu Arg Arg His (SEQ ID NO. 33)-OH, wherein X is H, H-Gly-Ser-Gly-, or H-Ser-Pro-Lys-Met-Val-Gln-Gly-Ser-Gly (SEQ ID NO. 34).

U.S. Pat. No. 4,904,763, issued Feb. 27, 1990 (the entire disclosure of which is incorporated herein by reference) describes other natriuretic peptide analogs suitable for use in the present invention, including X-Cys-Phe-Gly-Arg-Arg-Leu-Asp-Arg-Ile-Gly-Ser-Leu-Ser-Gly-Leu-Gly-Cys (SEQ ID NO. 35)-Y (where the 2 cysteines are bridged by a disulfide bond) wherein X means H or H-Asp-Ser.-Gly- and Y denotes -Asn-Val-Leu-Arg-Arg-Tyr-OH (SEQ ID NO. 36), -Asn-Val-Leu-Arg-Arg-OH (SEQ ID NO. 37), -Asn-Val-Leu-Arg-Tyr-OH (SEQ ID NO. 38), -Asn-Val-Leu-Arg-OH (SEQ ID NO. 39), -Asn-Val-Leu-OH (SEQ ID NO. 40) or Asn-Ser-Phe-Arg-Tyr-OH (SEQ ID NO. 41), or a salt thereof. Another set of analogs suitable for use in PCT Publication No. W08912069, published Dec. 14, 1989.

A further set of natriuretic peptide analogs suitable for use in the present invention is described in U.S. Patent Publication No. 20030109430, published on Jun. 12, 2003, the entire disclosure of which is incorporated herein by reference. This publication describes a peptide having natriuretic activity of the formula: R¹-Cys-Phe-Gly-Arg-Arg/Lys-Leu/f/Met-Asp-Arg-Ile-Lys-Met-Gly/Ser-Ser-LeulSer-Ser-Gly-Leu-Gly-Cys (SEQ ID NO. 42)-R2 , wherein R¹ is selected from the group consisting of: (H); Gly-; Ser-Gly-; Asp/Lys/Gly-Ser-Gly-; Arg/His/Gln-Asp/Lys/Gly-Ser-Gly- (SEQ ID NO. 43); Met/Val-Arg/His/Gln-Asp/Lys/Gly-Ser-Gly- (SEQ ID NO. 44); Thr/Met-Met/Val-Arg/His/Gln-Asp/Lys/Gly-Ser-Gly- (SEQ ID NO. 45); Lys-Thr/Met-Met/Val-Arg/His/Gln-Asp/Lys/Gly-Ser-Gly-(SEQ ID NO. 46); Pro-Lys-Thr/Met-Met/Val-Arg/His/Gln-Asp/Lys/Gly-Ser-Gly- (SEQ ID NO. 47); Ser-Pro-Lys-Thr/Met-Met/Val-Arg/His/Gln-Asp/Lys/Gly-Ser-Gly-(SEQ ID NO. 48); or a 10 to 109-amino acid sequence of the native upstream sequence for porcine, canine or human BNP, or a composite thereof; R² is (OH), NH2, or NR'R" wherein R' and R" are independently lower alkyl (in this case, 1-4 C) or is Asn/Lys; Asn/Lys-Val; Asn/Lys-Val-Leu; Asn/Lys-Val-Leu-Arg (SEQ ID NO. 49); Asn/Lys-Val-Leu-Arg-Arg/Lys (SEQ ID NO. 50); Asn/Lys-Val-Leu-Arg-Arg/Lys-Tyr/His (SEQ ID NO. 51); or the amides (NH₂ or NR'R") thereof, with the proviso that if the formula is R¹-Cys-Phe-Gly-Arg-Arg-Leu-Asp-Arg-Ile-Gly-Ser-Leu-Ser-Gly-Leu-Gly-Cys-R² (SEQ ID NO. 52), and R¹ is Asp-Ser-Gly-, R² cannot be Asn-Val-Leu-Arg-Arg-Tyr (SEQ ID NO. 53).

Still another set of analogs is described in Scios, European Patent EP0542863B1, issued Nov. 26, 1997, which describes a fusion protein which comprises from N-terminal to C-terminal: a carrier protein of about 10 to about 50 kDa which does not contain Glu residues or Asp-Gly sequences as a *Staph* V8 cleavage site; a *Staph* V8 cleavage comprising a Glu residue or Asp-Gly sequence positioned at the C-terminal of said carrier; and; and a peptide not containing a *Staph* V8 cleavage site fused to said cleavage site; wherein said fusion protein exhibits a pI of about 8.0 or greater. The patent also describes the use of an N-terminal leader of 6 to 20 amino acids.

Other natriuretic peptide analogs suitable for use in the present invention are described in Daiichi's U.S. Patent Publication No. 20020086843, published on Jul. 4, 2002 (the entire disclosure of which is incorporated herein by reference), which describes a physiologically active polypeptide X-Cys-Phe-Gly-Arg-Lys-Met-Asp-Arg-Ile-Ser-Ser-Ser-Ser-Gly-Leu-Gly-Cys-Lys-Val-Leu-Arg-Arg-His (SEQ ID NO. 54)-OH [where the 2 cysteines are bridged] wherein X is H, H-Gly-Ser-Gly-, or H-Ser-Pro-Lys-Met-Val-Gln-Gly-Ser-Gly- (SEQ iD NO. 55).

In making such substitutions, the hydropathic index of amino acids can be considered. The importance of the hydropathic amino acid index in conferring interactive biologic function on a polypeptide is generally understood in the art. It is accepted that the relative hydropathic character of the amino acid contributes to the secondary structure of the resultant polypeptide, which in turn defines the interaction of the protein with other molecules. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagines (−3.5); Lys (−3.9); and Arg (4.5). As will be understood by those skilled in the art, certain amino acids can be substituted by other amino acids having a similar hydropathic index or score and still result in a polypeptide with similar biological activity, i.e., still obtain a biological functionally equivalent polypeptide. In making such changes, the substitution of amino acids whose hydropathic indices are within ±2 of each other is preferred, those which are within ±1 of each other are particularly preferred, and those within ±0.5 of each other are even more particularly preferred.

It is also understood in the art that the substitution of like amino acids can be made effectively on the basis of hydrophilicity. U.S. Pat. No. 4,554,101, the disclosure of which is incorporated herein in its entirety, provides that the greatest local average hydrophilicity of a protein, as governed by the hydrophilicity of its adjacent amino acids, correletates with a biological property of the protein. As detailed in U.S. Pat. No. 4,554,101, the following hydrophilicity values have been assigned to amino acid residues: Arg (+3.0); Lys (±3.0); aspartate (±3.0±1); glutamate (±3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). As is understood by those skilled in the art, an amino acid can be substituted for another having a similar hydrophilicity value and still obtain a biologically equivalent, and in particular, an immunologically equivalent polypeptide. In such changes, the substitution of amino acids whose hydrophilicity values are within ±2 of each other is preferred, those which are within ±1 of each other are particularly preferred, and those within +0.5 of each other are even more particularly preferred.

As outlined above, amino acid substitutions/insertions can be based on the relative similarity of the amino acid side-chain substituents, for example, their hydrophobicity, hydrophilicity, charge, size, and the like. Exemplary substitutions (i.e., amino acids that can be interchanged without significantly altering the biological activity of the polypeptide) that take various of the foregoing characteristics into consideration are well known to those skill in the art and include, for example Arg and Lys; glutamate and aspartate; serine and threonine; glutamine and asparagine; and valine, leucine and isoleucine.

As will be understood by those skilled in the art, natriuretic peptide (e.g., BNP) analogs can be prepared by a variety of recognized peptide synthesis techniques including, but not limited to, classical (solution) methods, solid phase methods, semi-synthetic methods, and recombinant DNA methods.

7.1.3 Multi-BNP Peptide

The natriuretic compound may also be a multipeptide having two or more natriuretic compound units in sequence and optionally including spacer sequences between the natriuretic compound units. The compounds may also optionally comprise a leader and/or extension sequence at either or both ends of the natriuretic peptide compound. For example, by way of example and not limiting and without limiting the structure and/or formula of each multipeptide may, have the following structures:

NP-[NP]$_n$;
NP-[Spacer-NP]$_n$;
Leader-NP-[NP]$_n$;
Leader-NP-[Spacer-NP]$_n$;
Leader-[Spacer-NP]$_n$;
Leader-[Spacer-NP]$_n$-Extension;
Leader-NP-[Spacer-NP]$_n$-Extension;

where n may, for example be 1, 2, 3, 4, 5, 6, 7, 8, 9 or 10;

NP is a natriuretic peptide or natriuretic peptide analog;

Spacer may be an amino acid residue or a series of amino acid residues that are cleaved by an enzyme or enzyme cocktail, preferably an amino acid residue or sequence of amino acids not present in NP (e.g., Glu-Asp-Ala-Gly-Glu (SEQ ID NO. 56); Arg-Thr-Arg-Arg (SEQ ID NO. 57); Arg-X-Lys-Arg (SEQ ID NO. 58); Arg-Val; Asp-Lys; Lys-Ile; Arg-Thr; Arg-Ile);

Leader may for example be a single amino acid, an amino acid sequence, a peptide (e.g., leader peptide or signal peptide), or a protein; and Leader is selected to block the N-terminus from conjugation, assists in purification of the multipeptide (e.g., (His)$_6$-Ala-Asp-Gly-Glu (SEQ ID NO. 59)—cleavable by enzyme cocktail: V8 protease (endoproteinase Glu-C), (His)$_6$-Ala-Asp-Arg-Thr-Arg-Arg- (SEQ ID NO. 60) or (His)6-Ala-Asp-Arg-X-Lys-Arg (SEQ ID NO. 61) where X can be any amino acid or (His)6-Ala-Asp-Arg-Glu-Arg-Arg (SEQ ID NO. 62)—cleavable by Furin; (His)6-Ala-Asp-Arg-Val (SEQ ID NO. 63)—cleavable by Urokinase; (His)6-Ala-Asp-Lys (SEQ ID NO. 64) or (His)6-Ala-Asp-Lys-Ile- (SEQ ID NO. 65) Cleavable by Enterokinase; (His)6-Ala-Asp-Arg-Thr (SEQ ID NO. 66) or (His)6-Ala-Asp-Arg-Ile- (SEQ ID NO. 67) Cleavable by Factor Xa or Factor 10a), improves solubility and/or assists in excretion from the cell (e.g., Ala-Asp-Gly-Glu (SEQ ID NO. 68)), and/or purification (e.g., (His)$_6$-Ala-Asp-Gly-Glu (SEQ ID NO. 69)); and Leader is preferably cleavable from the multipeptide by enzymatic or chemical cleavage, preferably by an enzyme that would not cleave the NP; the Leader can be a leader peptide from a native NP;

Extension may for example be a single amino acid, an amino acid sequence, a peptide (e.g., leader peptide or signal peptide), or a protein; and Extension is selected to block the C-terminus from conjugation, assist in purification of the multipeptide (e.g., (His)$_6$-Ala-Asp-Gly-Glu (SEQ ID NO. 69)), improves solubility, and/or assists in excretion from the cell, (e.g., Ala-Asp-Gly-Glu (SEQ ID NO. 68)—cleavable by enzyme cocktail: V8 protease (endoproteinase Glu-C) and endoproteinase (Asp-N), Arg-Thr-Arg-Arg- (SEQ ID NO. 57) or Arg-X-Lys-Arg (SEQ ID NO. 58) where X can be any amino acid or Arg-Glu-Arg-Arg (SEQ ID NO. 70)—cleavable by Furin; Arg-Val-cleavable by enzyme cocktail Urokinase and carboxypeptidase B; Asp-Lys or Lys-Ile-Cleavable by Enterokinase; Arg-Thr or Arg-Ile-Cleavable by Factor Xa or Factor 10a); and Extension is preferably cleavable from the multipeptide by enzymatic or chemical cleavage preferably by an enzyme that would not cleave the NP.

Enzyme cleavage sites, such those included in the Spacer, or separating the leader and/or extension from the NP, are preferably selected so that a single enzyme or enzyme cocktail will cleave all of the cleavage sites. For example, the cleavage site Arg-Thr-Arg-Arg (SEQ ID NO. 57) can be cleaved by Furin.

In one embodiment, Leader is (His)$_6$-Ala-Asp-Gly-Glu (SEQ ID NO. 69), Extension is (His)$_6$-Ala-Asp-Gly-Glu (SEQ ID NO. 69), Spacer is GluAla-Asp-Gly-Glu (SEQ ID NO. 71). This embodiment can be cleaved by V8 protease (endoproteinase Glu-C). The resulting product is NP-Glu or NP-Glu conjugate.

In another embodiment, Leader is (His)$_6$-Ala-Asp-Gly-(-Arg-Thr-Arg-Arg (SEQ ID NO. 72) or Arg-X-Lys-Arg (SEQ ID NO. 73)) (where X is can be any amino acid), Extension is (His)$_6$-Ala-Asp-Gly-(-Arg-Thr-Arg-Arg (SEQ ID NO. 72) or Arg-X-Lys-Arg (SEQ ID NO. 73)) (where X can be any amino acid), and Spacer is Arg-Thr-Arg-Arg (SEQ ID NO. 57) or Arg-X-Lys-Arg (SEQ ID NO. 58) (where X is any amino acid). This embodiment can be cleaved by Furin. The resulting product is NP or NP conjugate.

In another embodiment, Leader is (His)$_6$-Ala-Asp-Gly-Arg-Val (SEQ ID NO. 74), Extension is (His)$_6$-Ala-Asp-Gly-Arg-Val (SEQ ID NO. 74), and Spacer is Arg-Val. This embodiment can be cleaved by a Urokinase/Carboxypeptidase B cocktail. The resulting product is NP or NP conjugate.

In another embodiment, Leader is (His)$_6$-Ala-Asp-Gly-(-Asp-Lys (SEQ ID NO. 75) or -Lys-Ile (SEQ ID NO. 76)), Extension is (His)$_6$-Ala-Asp-Gly-(-Asp-Lys (SEQ ID NO. 75) or -Lys-Ile (SEQ ID NO. 76) and Spacer is Asp-Lys or Lys-Ile). This embodiment can be cleaved by a Enterokinase. The resulting product is NP or NP conjugate.

In another embodiment, Leader is (His)$_6$-Ala-Asp-Gly-(-Arg-Thr (SEQ ID NO. 77) or -Arg-Ile (SEQ ID NO. 78)), Extension is (His)$_6$-Ala-Asp-Gly-(-Arg-Thr (SEQ ID NO. 77) or -Arg-Ile (SEQ ID NO. 78)), and Spacer is Arg-Thr or Arg-Ile. This embodiment can be cleaved by a Factor Xa or Factor 10a/Carboxypeptidase B enzyme cocktail. The resulting product is NP or NP conjugate.

In another embodiment, Spacer is Arg-Arg-Asp-Ala-Glu-Asp-Pro-Arg (SEQ ID NO. 79), Leader is Glu-Gly-Asp-Arg-Arg (SEQ ID NO. 80), and Extension is (His)$_6$-Glu-Gly-Asp-Arg-Arg (SEQ ID NO. 81). In this embodiment, the NP or NP conjugate can be released using a trypsin and carboxypeptidse B enzyme cocktail under controlled conditions.

In another embodiment, Spacer is Arg-Arg-Asp-Ala-Glu-Asp-Arg-Arg (SEQ ID NO. 82), Leader is Glu-Gly-Asp-Arg-Arg (SEQ ID NO. 83), Extension is (His)$_6$ (SEQ ID NO. 84)-AAA-Glu-Gly-Asp-Arg-Arg (SEQ ID NO. 83), where AAA is an amino acid sequence from 3 to 40 amino acid residue in length, preferably 3-15. In this embodiment, the NP or NP conjugate can be released using a trypsin and carboxypeptidse B enzyme cocktail under controlled conditions.

In another embodiment, Spacer is Arg-Gly-Asp-Ala-Glu-Asp-Pro-Arg (SEQ ID NO. 85), Leader is Glu-Gly-Asp-Pro-Arg (SEQ ID NO. 86), and Extension is (His)$_6$-Glu-Gly-Asp-Pro-Arg (SEQ ID NO. 87). In this embodiment, the NP or NP conjugate can be released using a thrombine and Carboxypeptidse B enzyme cocktail.

In another embodiment, Spacer is Ala-Arg-Gly-Asp-Ala-Glu-Asp-Pro-Arg (SEQ ID NO. 88), Leader is Glu-Gly-Asp-Pro-Arg (SEQ ID NO. 89), and Extension is (His)$_6$-Glu-Gly-Asp-Pro-Arg (SEQ ID NO. 90). In this embodiment, the NP or NP conjugate can be released using a thrombine and carboxypeptidse A enzyme cocktail.

In another embodiment, Spacer is Met-Met, Leader is Met-Met, and extension is (His)$_6$ (SEQ ID NO. 84)-AAA-Met-Met, where AAA is any amino acid sequence from 3 to 40 amino acid residues in length. In this embodiment, the NP or NP conjugate can be released using CNBr.

In another embodiment, Spacer is Asp-Asp-Ala-Gly-Glu (SEQ ID NO. 92), Leader is Ala-Asp-Gly-Glu (SEQ ID NO. 93), and Extension is (His)$_6$-Ala-Asp-Gly-Glu (SEQ ID NO. 59). In this embodiment, the NP or NP conjugate can be released using a V8 protease (endoproteinase Glu-C) and endoproteinase Asp-N coctail.

In another embodiment, Spacer is Glu-Ala-Gly-Glu (SEQ ID NO. 94), Leader is Ala-Asp-Gly-Glu (SEQ ID NO. 68), and Extension is (His)$_6$-Ala-Asp-Gly-Glu (SEQ ID NO. 69). In this embodiment, the NP or NP conjugate can be released using a V8 protease (endoproteinase Glu-C) to yield NP-Glu, a novel NP analog or a conjugate of NP Glu.

In another embodiment, Spacer is Glu-Glu, Leader is Glu-Gly-Asp-Ala (SEQ ID NO. 95) at the C-terminus and Extension is Glu-Gly-Asp-Ala(His)$_6$-Glu (SEQ ID NO. 96), where the C-terminus is linked with a fusion partner, an appropriate fusion protein, which can, for example, be cleavable via enterokinase. In this embodiment, the NP or NP conjugate can be released using a V8 protease (endoproteinase Glu-C) to yield NP-Glu, a novel NP analog or a conjugate of NP Glu.

In another embodiment, Spacer is Glu-Glu, Leader is Ala-Asp-Gly-Glu (SEQ ID NO. 68) and Extension is (His)$_6$-Ala-Asp-Gly-Glu (SEQ ID NO. 69) where the N-terminus is linked with a fusion partner, an appropriate fusion protein, which can, for example, be cleavable via enterokinase. In this embodiment, the NP or NP conjugate can be released using a V8 protease (endoproteinase Glu-C) to yield NP-Glu, a novel NP analog or a conjugate of NP Glu.

In another embodiment, Spacer is Glu-Glu, Leader is Glu-Gly-Asp-Ala-Glu (SEQ ID NO. 97) and the Extension is Glu-Gly-Asp-Ala-Glu (SEQ ID NO. 97), and the C-terminus is linked with a fusion partner, an appropriate fusion protein. In this embodiment, the NP or NP conjugate can be released using a V8 protease (endoproteinase Glu-C) to yield NP-Glu, a novel NP analog, or a conjugate of NP Glu.

In another embodiment, Spacer is Glu-Glu, Leader is Ala-Asp-Gly-Glu (SEQ ID NO. 68) and Extension is Glu-(His)$_6$-Ala-Asp-Gly-Glu (SEQ ID NO. 98) where the N-terminus is linked with a fusion partner, an appropriate fusion protein. In this embodiment, the NP or NP conjugate can be released using a V8 protease (endoproteinase Glu-C) to yield NP-Glu, a novel NP analog or a conjugate of NP Glu.

7.2 Modifying Moieties

Modifying moieties are moieties that modify the natriuretic compound, such as a BNP peptide compound, and provide the compound with desired properties as described herein. For example, the modifying moiety can reduce the rate of degradation of the natriuretic compound in various environments (such as the GI tract, and/or the bloodstream), such that less of the natriuretic compound is degraded in the modified form than would be degraded in the absence of the modifying moiety in such environments. Preferred modifying moieties are those which permit the natriuretic compound conjugate to retain a therapeutically significant percentage of the biological activity of the parent natriuretic compound.

7.2.1 Moieties that Effect Stability, Solubility, and/or Biological Activity There are numerous moieties that can be attached to the natriuretic compound to form the natriuretic compound conjugates described herein that modify the stability, solubility, and/or biological activity of the parent natriuretic compound. Examples include hydrophilic polymers or oligomers, amphiphilic polymers or oligomers, and lipophilic polymers or oligomers.

The polymers (or shorter chain oligomers) can include weak or degradable linkages in their backbones. For example, the polyalkylene glycols can include hydrolytically unstable linkages, such as lactide, glycolide, carbonate, ester, carbamate and the like, which are susceptible to hydrolysis. This allows the polymers to be cleaved into lower molecular weight fragments. Examples of such polymers are described, for example, in U.S. Pat. No. 6,153,211 to Hubbell et al.

Representative hydrophilic, amphiphilic, and lipophilic polymers and oligomers are described in more detail below.

7.2.2 Hydrophilic Moieties

The hydrophilic moiety may be various hydrophilic moieties as will be understood by those skilled in the art including, but not limited to, polyalkylene glycol moieties, other hydrophilic polymers, sugar moieties, polysorbate moieties, and combinations thereof.

7.2.2.1 Polyalkylene Glycol Moieties

Polyalkylene glycols are compounds with repeat alkylene glycol units. In some embodiments, the units are all identical (e.g., polyethylene glycol or polypropylene glycol). In other embodiments, the alkylene units are different (e.g., polyethylene-co-propylene glycol, or PLURONICS®). The polymers can be random copolymers (for example, where ethylene oxide and propylene oxide are co-polymerized) or branched or graft copolymers.

Polyethylene glycol, or PEG, is a preferred polyalkylene glycol, and is useful in biological applications because it has highly desirable properties and is generally regarded as safe (GRAS) by the Food and Drug Administration. PEG has the formula —$(CH_2CH_2O)_n$—, where n can range from about 2 to about 4000 or more. PEG typically is colorless, odorless, water-soluble or water-miscible (depending on molecular weight), heat stable, chemically inert, hydrolytically stable, and generally nontoxic. PEG is also biocompatible, and typically does not produce an immune response in the body. Preferred PEG moieties of the invention include a number of PEG subunits selected from the following ranges shown in order of increasing preference: 2-50, 2-40, 2-30, 2-25, 2-20, 2-15, 2-10. In certain embodiments, the modifying moieties will include 2, 3, 4, 5, 6, 7, 8, 9, or 10 subunits.

The PEG may be monodispersed (e.g., as previously described by the applicants in U.S. patent application Ser. Nos. 09/873,731 and 09/873,797, both filed Jun. 4, 2001 the entire disclosures of which are incorporated herein by reference) or polydispersed as commonly supplied on the market. By mono-dispersed, it is meant that the polyalkylene glycol can have a single molecular weight, or a relatively narrow range of molecular weights. One advantage of using the relatively low molecular weight, monodispersed polymers is that they form easily defined conjugate molecules, which can facilitate both reproducible synthesis and FDA approval.

The PEG can be a linear polymer with a hydroxyl group at each terminus (before being conjugated to the remainder of the natriuretic compound). The PEG can also be an alkoxy PEG, such as methoxy-PEG (or mPEG), where one terminus is a relatively inert alkoxy group, while the other terminus is a hydroxyl group (that is coupled to the natriuretic compound). The PEG can also be branched, which can in one embodiment be represented as R(-PEG-OH)$_m$ in which R represents a central (typically polyhydric) core agent such as pentaerythritol or glycerol, and m represents the number of arms. Each branch can be different and can be terminated, for example, with ethers and/or esters. The number of arms m can range from three to a hundred or more, and one or more of the terminal hydroxyl groups can be coupled to the remainder of the natriuretic compound, or otherwise subject to chemical modification. Other branched PEG include those represented by the formula ($CH_3O$-PEG-)$_p$R-Z, where p equals 2 or 3, R represents a central core such as Lys or glycerol, and Z represents a group such as carboxyl that is subject to ready chemical activation. Still another branched form, the pendant PEG, has reactive groups, such as carboxyls, along the PEG backbone rather than, or in addition to, the end of the PEG chains. Forked PEG can be represented by the formula PEG (-LCHX$_2$)$_n$ is another form of branched PEG, where L is a linking group and X is an activated terminal group. The term polyethylene glycol or PEG represents or includes all forms of linear or branched PEG, and polyalkalene glycol or PEG includes all forms of linear or branched PEG.

7.2.2.2 Sugar Moieties

The natriuretic compounds described herein can include sugar moieties, as such as known by those skilled in the art. In general, the sugar moiety is a carbohydrate product of at least one saccharose group. Representative sugar moieties include, but are not limited to, glycerol moieties, mono-, di-, tri-, and oligosaccharides, and polysaccharides such as starches, glycogen, cellulose and polysaccharide gums. Specific monosaccharides include $C_6$ and above (preferably $C_6$ to $C_8$) sugars such as glucose, fructose, mannose, galactose, ribose, and sedoheptulose; di- and trisaccharides include moieties having two or three monosaccharide units (preferably $C_5$ to $C_8$) such as sucrose, cellobiose, maltose, lactose, and raffinose. An example of a modifying moiety including a sugar moiety is as follows:

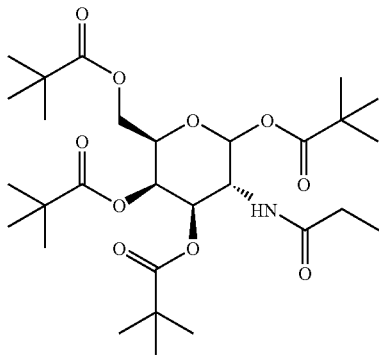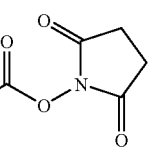

Conjugation using sugar moieties is described in U.S. Pat. Nos. 5,681,811, 5,438,040, and 5,359,030, the entire disclosures of which are incorporated herein by reference.

7.2.2.3 Polysorbate Moieties

The polysorbate moiety may be various polysorbate moieties as will be understood by those skilled in the art including, but are not limited to, sorbitan esters, and polysorbate derivatized with polyoxyethylene. Conjugation using polysorbate moieties is described in U.S. Pat. Nos. 5,681,811, 5,438,040, and 5,359,030, the entire disclosures of which are incorporated herein by reference.

7.2.2.4 Biocompatible Water-Soluble Polycationic Moieties

In some embodiments, biocompatible water-soluble polycationic polymers can be used. Biocompatible water-soluble polycationic polymers include, for example, any polymer having protonated heterocycles attached as pendant groups. "Water soluble" means that the entire polymer is soluble in aqueous solutions, such as buffered saline or buffered saline with small amounts of added organic solvents as cosolvents, at a temperature between 20 and 37° C. In some embodiments, the polymer itself is not sufficiently soluble in aqueous solutions per se but is brought into solution by grafting with water-soluble polymers such as PEG chains. Examples include polyamines having amine groups on either the polymer backbone or the polymer sidechains, such as poly-L-Lys and other positively charged polyamino acids of natural or synthetic amino acids or mixtures of amino acids, including poly(D-Lys), poly(ornithine), poly(Arg), and poly(histidine), and nonpeptide polyamines such as poly(aminostyrene), poly (aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan.

7.2.2.5 Other Hydrophilic Moieties

Other hydrophilic polymers can also be used. Examples include poly(oxyethylated polyols) such as poly(oxyethylated glycerol), poly(oxyethylated sorbitol), and poly(oxyethylated glucose); poly(vinyl alcohol) ("PVA"); dextran; carbohydrate-based polymers and the like. The polymers can be homopolymers or random or block copolymers and terpolymers based on the monomers of the above polymers, linear chain or branched.

Specific examples of suitable additional polymers include, but are not limited to, poly(oxazoline), difunctional poly (acryloylmorpholine) ("PAcM"), and poly(vinylpyrrolidone) ("PVP"). PVP and poly(oxazoline) are well known polymers in the art and their preparation should be readily apparent to the skilled artisan. PAcM and its synthesis and use are described in U.S. Pat. Nos. 5,629,384 and 5,631,322, the disclosures of which are incorporated herein by reference in their entirety.

7.2.3 Bioadhesive Polyanionic Moieties

Certain hydrophilic polymers appear to have potentially useful bioadhesive properties. Examples of such polymers are found, for example, in U.S. Pat. No. 6,197,346 to Mathiowitz, et al. Those polymers containing carboxylic groups (e.g., poly(acrylic acid)) exhibit bioadhesive properties, and also are readily conjugated with the natriuretic compounds described herein. Rapidly bioerodible polymers that expose carboxylic acid groups on degradation, such as poly(lactide-co-glycolide), polyanhydrides, and polyorthoesters, are also bioadhesive polymers. These polymers can be used to deliver the natriuretic compounds to the gastrointestinal tract. As the polymers degrade, they can expose carboxylic acid groups to enable them to adhere strongly to the gastrointestinal tract, and can aid in the delivery of the natriuretic compound conjugates.

7.2.4 Lipophilic Moieties

In some embodiments, the modifying moiety comprises a lipophilic moiety. The lipophilic moiety may be various lipophilic moieties as will be understood by those skilled in the art including, but not limited to, alkyl moieties, alkenyl moieties, alkynyl moieties, aryl moieties, arylalkyl moieties, alkylaryl moieties, fatty acid moieties, adamantantyl, and cholesteryl, as well as lipophilic polymers and/or oligomers.

The alkyl moiety can be a saturated or unsaturated, linear, branched, or cyclic hydrocarbon chain. In some embodiments, the alkyl moiety has at least 1, 2, 3, or more carbon atoms. In other embodiments, the alkyl moiety is a linear, saturated or unsaturated alkyl moiety having between 1, 2, 3, 4, 5, 6, 7, 8, 9, 10, 11, 12, 13, 14, 15, 16, 17, 18, 19 or 20 carbon atoms. Examples include saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. In other embodiments, the alkyl moiety is a lower alkyl moiety. In still other embodiments, the alkyl moiety is a $C_1$ to $C_3$ lower alkyl moiety. In some embodiments, the modifying moiety specifically does not consist of an alkyl moiety, or specifically does not consist of a lower alkyl moiety, or specifically does not consist of an alkane moiety, or specifically does not consist of a lower alkane moiety.

The alkyl groups can either be unsubstituted or substituted with one or more substituents, and such substituents preferably either do not interfere with the methods of synthesis of the conjugates or eliminate the biological activity of the conjugates. Potentially interfering functionality can be suitably blocked with a protecting group so as to render the functionality non-interfering. Each substituent may be optionally substituted with additional non-interfering substituents. The term "non-interfering" characterizes the substituents as not adversely affecting any reactions to be performed in accordance with the process of this invention.

The fatty acid moiety may be various fatty acid moieties including natural or synthetic, saturated or unsaturated, linear or branched fatty acid moieties. In some embodiments, the fatty acid moiety has at least 2, 3, 4, or more carbon atoms. In other embodiments, the fatty acid moiety has 2, 3, 4, 5, 6, 7, 8, 9, 10, 11, 12, 13, 14, 15, 16, 17, 18, 19, 20, 21, 22, 23, or 24 carbon atoms.

When the modifying moiety is an aryl ring, the ring can be functionalized with a nucleophilic functional group (such as OH, SH, or NHR') that is positioned so that it can react in an intramolecular fashion with the carbamate moiety and assist in its hydrolysis. In some embodiments, the nucleophilic group is protected with a protecting group capable of being hydrolyzed or otherwise degraded in vivo, with the result being that when the protecting group is deprotected, hydrolysis of the conjugate, and resultant release of the parent natriuretic compound, is facilitated.

7.2.5 Amphiphilic Moieties

In some embodiments, the modifying moiety includes an amphiphilic moiety. Many polymers and oligomers are amphiphilic. These are often block co-polymers, branched copolymers or graft co-polymers that include hydrophilic and lipophilic moieties, which can be in the form of oligomers and/or polymers, such as linear chain, branched, or graft polymers or co-polymers.

The hydrophilic polymers or oligomers described may include combinations of any of the lipophilic and hydrophilic moieties described herein. Such polymers or oligomers typically include at least one reactive functional group, for example, halo, hydroxyl, amine, thiol, sulfonic acid, carboxylic acid, isocyanate, epoxy, ester, and the like, which are often at the terminal end of the polymer. These reactive functional groups can be used to attach a lipophilic linear or branched chain alkyl, alkenyl, alkynyl, arylalkyl, or alkylaryl group, or a lipophilic polymer or oligomer, thereby increasing the lipophilicity of the hydrophilic polymers or oligomers (and thereby rendering them generally amphiphilic).

The lipophilic groups can, for example, be derived from mono- or di-carboxylic acids, or where appropriate, reactive equivalents of carboxylic acids such as anhydrides or acid chlorides. Examples of suitable precursors for the lipophilic groups are acetic acid, propionic acid, butyric acid, valeric acid, isobutyric acid, trimethylacetic acid, caproic acid, caprylic acid, heptanoic acid, capric acid, pelargonic acid, lauric acid, myristic acid, palmitic acid, stearic acid, behenic acid, lignoceric acid, ceratic acid, montanoic acid, isostearic acid, isononanoic acid, 2-ethylhexanoic acid, oleic acid, ricinoleic acid, linoleic acid, linolenic acid, erucic acid, soybean fatty acid, linseed fatty acid, dehydrated castor fatty acid, tall oil fatty acid, tung oil fatty acid, sunflower fatty acid, safflower fatty acid, acrylic acid, methacrylic acid, maleic anhydride, orthophthalic anhydride, terephthalic acid, isophthalic acid, adipic acid, azelaic acid, sebacic acid, tetrahydrophthalic anhydride, hexahydrophthalic anhydride, succinic acid and polyolefin carboxylic acids.

The terminal lipophilic groups need not be equivalent, i.e., the resulting copolymers can include terminal lipophilic groups that are the same or different. The lipophilic groups can be derived from more than one mono or di-functional alkyl, alkenyl, alkynyl, cycloalkyl, arylalkyl or alkylaryl group as defined above.

7.2.5.1 PEG/Alkyl Modifying Moieties

The modifying moiety may be a linear or branched polymeric moiety comprising one or more linear or branched polyalkylene glycol moieties and/or one or more linear or branched, substituted or unsubstituted alkyl moieties. However, in certain embodiments, the modifying moiety specifically does not consist of an alkyl moiety and in other embodiments, the modifying moiety specifically does not consist of an alkane moiety. The polyalkylene glycol moieties in some embodiments include 1, 2, 3, 4, 5, 6, 7, 8, 9, 10, 11, 12, 13, 14, 15, 16, 17, 18, 19, 20, 21, 22, 23, 24, or 25 PAG subunits, preferably PEG or PPG subunits or combinations thereof. The alkyl moieties are saturated or unsaturated and are preferably 1, 2, 3, 4, 5, 6, 7, 8, 9, 10, 11, 12, 13, 14, 15, 16, 17, 18, 19, or 20 carbon atoms. The alkyl moieties are preferably alkane moieties.

The modifying moiety may, for example, have a formula:

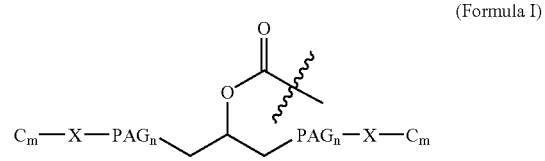

(Formula I)

wherein each C is independently selected and is an alkyl moiety having m carbons and m is 1, 2, 3, 4, 5, 6, 7, 8, 9, 10, 11, 12, 13, 14, 15, 16, 17, 18, 19, or 20; and each PAG is independently selected and is a polyalkylene glycol moiety having n subunits and n is 1, 2, 3, 4, 5, 6, 7, 8, 9, 10, 11, 12, 13, 14, 15, 16, 17, 18, 19, 20, 21, 22, 23, 24, or 25; each X is independently selected and is a linking moiety coupling PAG to C, and is preferably —C—, —O—, —C(O)—, —C(O)O—, —OC(O)—, —NH—, —NHC(O)—, or —C(O)NH—. In some embodiments the Cm—X moiety is absent, and the $PAG_n$ moiety is terminated with a capping group, such as an —OH moiety or an —OCH3 moiety. For example, the PAG may be methoxy-terminated or hydroxy-terminated PEG, having 1, 2, 3, 4, 5, 6, 7, 8, 9, 10, 11, 12, 13, 14, 15, 16, 17, 18, 19 or 20 PEG subunits.

It will be appreciated that the oligomer of Formula I is itself an aspect of the invention. The oligomer may be provided, for example, as a primary alcohol, a carboxylic acid or as an activated oligomer, and may be used to conjugate biologically active compounds, other than BNP, such as insulin, calcitonin, interferons, growth hormones, etc.

In another aspect, the modifying moiety may have a formula:

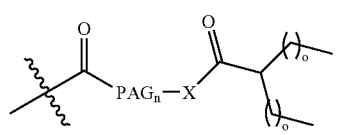

(Formula II)

wherein PAG is a polyalkylene glycol moiety having n subunits and n is 1, 2, 3, 4, 5, 6, 7, 8, 9, 10, 11, 12, 13, 14, 15, 16, 17, 18, 19, 20, 21, 22, 23, 24, or 25; X is —O—, or —NH—; each o is independently selected and is 0, 1, 2, 3, 4, 5, 6, 7, 8, 9, 10, 11, 12, 13, 14, or 15.

It will be appreciated that the oligomer of Formula II is itself an aspect of the invention. The oligomer may be provided, for example, as a primary alcohol, a carboxylic acid or as an activated oligomer, and may be used to conjugate biologically active compounds, other than BNP, such as insulin, calcitonin, interferons, growth hormones, etc.

In another aspect, the modifying moiety may have a formula:

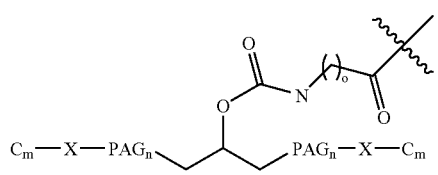

(Formula III)

wherein each C is independently selected and is an alkyl moiety having m carbons and m is 1, 2, 3, 4, 5, 6, 7, 8, 9, 10, 11, 12, 13, 14, 15, 16, 17, 18, 19, or 20; and each PAG is independently selected and is a polyalkylene glycol moiety having n subunits and n is 1, 2, 3, 4, 5, 6, 7, 8, 9, 10, 11, 12, 13, 14, 15, 16, 17, 18, 19, 20, 21, 22, 23, 24, or 25; each X is independently selected and is a linking moiety coupling PAG to C, and is preferably —C—, —O—, —C(O)—, —C(O)O—, —OC(O)—, —NH—, —NHC(O)—, or —C(O)NH—; o is 0, 1, 2, 3, 4, 5, 6, 7, 8, 9, 10, 11, 12, 13, 14, or 15. The $C_m$—X moiety may be absent, and the $PAG_n$ moiety terminated with an —OH moiety or an —OCH$_3$ moiety. For example, the PAG may be methoxy-terminated or hydroxy-terminated PEG, having 1, 2, 3, 4, 5, 6, 7, 8, 9, 10, 11, 12, 13, 14, 15, 16, 17, 18, 19 or 20 subunits.

In another aspect, the modifying moiety may have a formula:

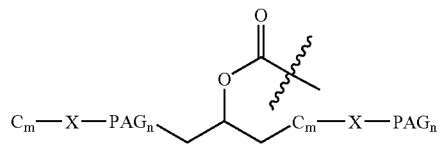

(Formula IV)

wherein each C is independently selected and is a saturated or unsaturated alkyl moiety having m carbons and m is 1, 2, 3, 4, 5, 6, 7, 8, 9, 10, 11, 12, 13, 14, 15, 16, 17, 18, 19, or 20; and each PAG is independently selected and is a polyalkylene glycol moiety having n subunits and n is 1, 2, 3, 4, 5, 6, 7, 8, 9, 10, 11, 12, 13, 14, 15, 16, 17, 18, 19, 20, 21, 22, 23, 24, or 25; each X is independently selected and is a linking moiety coupling PAG to C, and is preferably —C—, —O—, —C(O)—, —C(O)O—, —OC(O)—, —NH—, —NHC(O)—, or —C(O)NH—. It will be appreciated that the oligomers of Formulas I, II, III and IV are themselves an aspect of the invention. These oligomers may be provided, for example, as primary alcohols, carboxylic acids or as activated oligomers. They may be sold as reagents, e.g., for use in conjugating biologically active compounds, such as insulin, calcitonin, interferons, growth hormones, etc. They may be sold in kits containing the oligomers and reagents for activating them and/or conjugating them to other compounds.

In another aspect, the modifying moiety may have a formula:

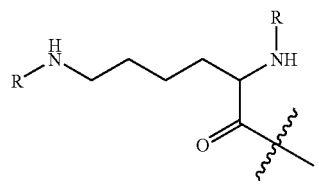

(Formula V)

wherein each R is independently selected and is any of Formulas I, II, III or IV above.

The pharmaceutical characteristics, such as hydrophilicity/lipophilicity of the conjugates can be varied by adjusting the number of PEG monomers, the type and length of alkyl chain, the nature of the PEG-peptide linkage, and the number of conjugation sites. The exact nature of the PEG-peptide linkage can be varied such that it is stable and/or sensitive to hydrolysis at physiological pH or in plasma.

7.2.6 Salt-Forming Moieties

In some embodiments, the modifying moiety comprises a salt-forming moiety. The salt-forming moiety may be various suitable salt-forming moieties as will be understood by those skilled in the art including, but not limited to, carboxylate and ammonium. In some embodiments wherein the modifying moiety includes a salt forming moiety, the natriuretic compound conjugate is provided in salt form. In these embodiments, the natriuretic compound conjugate is associated with a suitable pharmaceutically acceptable counterion as will be understood by those skilled in the art including, but not limited to, negative ions such as chloro, bromo, iodo, phosphate, acetate, carbonate, sulfate, tosylate, and mesylate, or positive ions such as sodium, potassium, calcium, lithium, and ammonium.

The modifying moiety can include any hydrophilic moieties, lipophilic moieties, amphiphilic moieties, salt-forming moieties, and combinations thereof. In preferred embodiments, the modifying moiety is selected from the group consisting of $(CH_2CH_2O)_pCH_3$ where p is 0, 1, 2, 3, 4, 5, 6, 7, 8, 9, 10, 11, 12, 13, 14, 15, 16, 17, 18, 19 or 20; $(CH_2)_qCH_3$ where q is 0, 1, 2, 3, 4, 5, 6, 7, 8, 9, 10, 11, 12, 13, 14, 15, 16, 17, 18, 19 or 20; $CH_2CH_2(OCH_2CH_2)_rOH$ where r is 0, 1, 2, 3, 4, 5, 6, 7, 8, 9, 10, 11, 12, 13, 14, 15, 16, 17, 18, 19 or 20; $C(CH_2OH)_3$; $CH(CH_2OH)_2$; $C(CH_3)_3$; $CH(CH_3)_2$; $CH_2CH_2(OCH_2CH_2)_nC(O)(CH_2)_nCH_3$ where s is 0, 1, 2, 3, 4, 5, 6, 7, 8, 9, 10, 11, 12, 13, 14, 15, 16, 17, 18, 19 or 20 and t is 0, 1, 2, 3, 4, 5, 6, 7, 8, 9, 10, 11, 12, 13, 14, 15, 16, 17, 18, 19 or 20; and $(CH_2CH_2O)_nC(O)(CH_2)_nCH_3$ where y is 0, 1, 2, 3, 4, 5, 6, 7, 8, 9, 10, 11, 12, 13, 14, 15, 16, 17, 18, 19 or 20 and z is 0, 1, 2, 3, 4, 5, 6, 7, 8, 9, 10, 11, 12, 13, 14, 15, 16, 17, 18, 19 or 20.

The foregoing examples of modifying moieties for specific purposes is intended as illustrative of the invention and should not be taken as limiting in any way. One skilled in the art will recognize that suitable moieties for conjugation to achieve particular functionality will be possible within the bounds of the chemical conjugation mechanisms disclosed and claimed herein. Accordingly, additional moieties can be selected and used according to the principles of the invention as disclosed herein.

7.3 Conjugation Strategies

The natriuretic compound conjugates of the invention can have a different level of biological activity relative to the corresponding unconjugated natriuretic compound conjugates. In some embodiments, the natriuretic compound retains some or all of the activity of the unmodified form, but by virtue of factors such as the degree of conjugation with modifying moieties, selection of conjugation sites on the molecule and selection of modifying moieties, is less susceptible to in vivo degradation, and thus, has an increased plasma half life. For example, the natriuretic compounds of the invention may be modified to include a modifying moiety at one, two, three, four, five, or more sites on the natriuretic compound structure at appropriate attachment (i.e., modifying moiety conjugation) sites suitable for facilitating the association of a modifying moiety thereon. By way of example, such suitable conjugation sites may comprise an amino acid residue, such as a Lys amino acid residue.

In many embodiments, for example, the biologically active agent functions, in part, by binding to an active site in a receptor. Often, when a functional group, such as an amino acid residue is modified, the agent no longer binds in the active site. In the case of BNP, for example, the peptide has a particular affinity for binding NPR-A. Depending on the site at which the natriuretic molecule is modified to include the modifying group, the affinity that the BNP has for the receptor may be the same, or may be reduced. In some embodiments, the natriuretic compound conjugates have less activity than the native, unconjugated natriuretic compound conjugates, but retain improved characteristics relative to unconjugated natriuretic compound conjugates, such as increased resistance to proteolysis and plasma half life or ability to cross a cell membrane. It is envisioned that reduced activity can be preferred, for example, when long term release of the natriuretic compound is desirable.

In some embodiments, the natriuretic compound conjugates are monoconjugates. In other embodiments, the natriuretic compound conjugates are multi-conjugates, such as di-conjugates, tri-conjugates, tetra-conjugates, penta-conjugates and the like. The number of modifying moieties on the natriuretic compound is limited only by the number of conjugation sites on the natriuretic compound. In still other embodiments, the natriuretic compound conjugates of the present invention are a mixture of mono-, di-, tri, tetra, and/or penta-modifying moiety conjugates. For example, in some embodiments, the biologically active natriuretic compound is hBNP, which includes within its 32 native amino acid sequence includes four preferred conjugation sites, including the N-terminus, $Lys^3$, $Lys^{14}$ and $Lys^{27}$. The work of the inventors points to monoconjugates conjugated at the N-terminus, $Lys^3$, $Lys^{14}$ or $Lys^{27}$, and diconjugates at $Lys^3/Lys^{14}$ and $Lys^3/Lys^{27}$ as highly preferred strategies for hBNP and related natriuretic peptides and analogs.

The modifying moiety is preferably covalently coupled to the natriuretic compound. More than one moiety on the modifying moiety may be covalently coupled to the natriuretic compound. Coupling may employ hydrolysable or non-hydrolysable bonds or mixtures of the two (i.e., different bonds at different conjugation sites).

In some embodiments, the natriuretic compound is coupled to the modifying moiety utilizing a hydrolysable bond (e.g., an ester, carbonate or carbamate bond). Use of a hydrolysable coupling will provide a natriuretic compound conjugate that acts as a prodrug. A prodrug approach may be desirable where the natriuretic compound-modifying moiety conjugate is inactive (i.e., the conjugate lacks the ability to affect the body through the natriuretic compound's primary mechanism of action), such as when the modifying moiety conjugation site is in a binding region of natriuretic compound. Use of a hydrolyzable coupling can also provide for a time-release or controlled-release effect, administering the natriuretic compound over a given time period as one or more modifying moieties are cleaved from their respective natriuretic compound-modifying moiety conjugates to provide the active drug.

In other embodiments, the natriuretic compound is coupled to the modifying moiety utilizing a non-hydrolyzable bond (e.g., a carbamate, amide, or ether bond). Use of a non-hydrolyzable bond may be preferable when it is desirable to allow the natriuretic compound-modifying moiety conjugate to circulate in the bloodstream for an extended period of time, preferably at least 2 hours. Bonds used to covalently couple the natriuretic compound to the modifying moiety in a non-hydrolysable fashion are typically selected from the group consisting of covalent bond(s), ester moieties, carbonate moieties, carbamate moieties, amide moieties and secondary amine moieties.

In still other embodiments, a partial prodrug approach may be used, in which a portion of the modifying moiety is hydrolyzed. For example, U.S. Pat. No. 6,309,633 (the entire disclosure of which is incorporated herein by reference) describes modifying moieties comprising hydrophilic and lipophilic components in which the lipophilic components hydrolyze in vivo to yield a microPAGylated conjugate.

More than one modifying moiety (i.e., a plurality of modifying moietys) may be coupled to the natriuretic compound. The modifying moieties in the plurality are preferably the same. However, it is to be understood that the modifying moieties in the plurality may be different from one another, or, alternatively, some of the modifying moieties in the plurality may be the same and some may be different. When a plurality of modifying moieties are coupled to the natriuretic compound, it may be preferable to couple one or more of the modifying moieties to the natriuretic compound with hydrolyzable bonds and couple one or more of the modifying moieties to the natriuretic compound with non-hydrolyzable bonds. Alternatively, all of the bonds coupling the plurality of modifying moieties to the natriuretic compound may be hydrolyzable, but have varying degrees of hydrolyzability such that, for example, one or more of the modifying moieties may be rapidly removed from the natriuretic compound by hydrolysis in the body and one or more of the modifying moieties is slowly removed from the natriuretic compound by hydrolysis in the body.

The modifying moiety may be coupled to the natriuretic compound at various nucleophilic residues of the drug including, but not limited to, nucleophilic hydroxyl functions and/or amino functions. Nucleophilic hydroxyl functions may be found, for example, at serine and/or tyrosine residues, and nucleophilic amino functions may be found, for example, at histidine and/or Lys residues, and/or at the one or more N-terminus of the polypeptide. When a modifying moiety is coupled to the N-terminus of the natriuretic peptide, coupling preferably forms a secondary amine.

7.4 Synthesis of the Conjugates

Exemplary syntheses are described in the examples set forth below. The reaction conditions (e.g., selected molar ratios, solvent mixtures and/or pH) may be controlled according to known principles. For example, conjugation at the amino functionality of Lys may be suppressed by maintaining the pH of the reaction solution below the $pK_a$ of Lys.

The mixture of natriuretic compound conjugates may be separated and isolated utilizing, for example, HPLC to provide natriuretic compound conjugates, for example mono-, di-, or tri-conjugates. The degree of conjugation (e.g., whether the isolated molecule is a mono-, di-, or tri-conjugate) of a particular isolated conjugate may be determined and/or verified utilizing various techniques as will be understood by those skilled in the art including, but not limited to, mass spectroscopy. The particular conjugate structure (e.g., $Lys^3$, $Lys^{14}$, $Lys^{27}$, or the N-terminus of hBNP monoconjugate) may be determined and/or verified utilizing various techniques as will be understood by those skilled in the art including, but not limited to, sequence analysis, peptide mapping, selective enzymatic cleavage, and/or endopeptidase cleavage.

One or more of the reaction sites on the natriuretic compound may be blocked by, for example, reacting the natriuretic compound with a suitable blocking reagent such as N-tert-butoxycarbonyl (t-BOC), or N-(9-fluorenylmethyloxycarbonyl) (N-FMOC). This process may be preferred, for example, when it is desired to form an unsaturated natriuretic compound conjugate (i.e., a conjugate wherein not all nucleophilic residues are conjugated) having a modifying moiety at one or more of the N-terminus of the polypeptide. Following such blocking, the substantially monodispersed mixture of blocked natriuretic compounds may be reacted with the substantially monodispersed mixture of activated modifying moieties to provide a mixture of natriuretic compound conjugates having modifying moiety(s) coupled to one or more nucleophilic residues and having blocking moieties coupled to other nucleophilic residues. After the conjugation reaction, the natriuretic compound-modifying moiety conjugates may be de-blocked as will be understood by those skilled in the art. If necessary, the mixture of natriuretic compound conjugates may then be separated as described above to provide a mixture of natriuretic compound conjugates. Alternatively, the mixture of natriuretic compound-modifying moiety conjugates may be separated prior to de-blocking.

In a surprising aspect of the invention, the inventors discovered that synthesis of an hBNP conjugate using a PEG-alkyl moiety with the alkyl moiety adjacent to the natriuretic compound (i.e., positioned between the natriuretic compound and the PEG moiety) results in preferential conjugation at the highly desirable $Lys^3$ conjugation site. Thus, in one aspect, the invention provides a method of preferentially conjugating hBNP at $Lys^3$ comprising activating the alkyl component of a PEG-alkyl oligomer and coupling the activated PEG-alkyl oligomer to the hBNP.

7.5 Pharmaceutical Compositions

Pharmaceutical compositions including the natriuretic compound conjugates described herein can be prepared. Such compositions typically include the modified natriuretic compound in combination with, or in admixture with, a pharmaceutically acceptable carrier. The carrier must, of course, be acceptable in the sense of being compatible with any other ingredients in the pharmaceutical composition and should not be deleterious to the patient. The carrier may be a solid or a liquid, or both, and is preferably formulated with the prodrug as a unit-dose formulation, for example, a tablet, which may contain from about 0.01 or 0.5% to about 95% or 99% by weight of the natriuretic compound conjugate. The pharmaceutical compositions may be prepared by any of the well-known techniques of pharmacy including, but not limited to, admixing the components, optionally including one or more accessory ingredients.

The pharmaceutical compositions according to embodiments of the present invention include those suitable for oral, rectal, nasal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend on the nature and severity of the condition being treated and on the nature of the particular prodrug which is being used.

Pharmaceutical compositions suitable for oral administration may be presented in discrete units, such as capsules, cachets, lozenges, or tablets, each containing a predetermined amount of the prodrug; as a powder or granules; as a solution or a suspension in an aqueous or non-aqueous liquid; or as an oil-in-water or water-in-oil emulsion. Such formulations may be prepared by any suitable method of pharmacy that includes the step of bringing into association the prodrug and a suitable carrier (which may contain one or more accessory ingredients as noted above). In general, the pharmaceutical composition according to embodiments of the present invention are prepared by uniformly and intimately admixing the prodrug with a liquid or finely divided solid carrier, or both, and then, if necessary, shaping the resulting mixture. For example, a tablet may be prepared by compressing or molding a powder or granules containing the prodrug, optionally with one or more accessory ingredients. Compressed tablets may be prepared by compressing, in a suitable machine, the mixture in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Pharmaceutical compositions suitable for buccal (sub-lingual) administration include lozenges comprising the prodrug in a flavored base, usually sucrose and acacia or tragacanth; and pastilles comprising the prodrug in an inert base such as gelatin and glycerin or sucrose and acacia.

Pharmaceutical compositions according to embodiments of the present invention suitable for parenteral administration comprise sterile aqueous and non-aqueous injection solutions of the prodrug, which preparations are preferably isotonic with the blood of the intended recipient. These preparations may contain anti-oxidants, buffers, bacteriostats and solutes which render the composition isotonic with the blood of the intended recipient. Aqueous and non-aqueous sterile suspensions may include suspending agents and thickening agents. The compositions may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, an injectable, stable, sterile composition comprising a prodrug in a unit dosage form in a sealed container may be provided. The prodrug is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the prodrug. When the prodrug is substantially water-insoluble, a sufficient amount of emulsifying agent which is physiologically acceptable may be employed in sufficient quantity to emulsify the prodrug in an aqueous carrier. One such useful emulsifying agent is phosphatidyl choline.

Pharmaceutical compositions suitable for topical application to the skin preferably take the form of an ointment, cream, lotion, paste, gel, spray, aerosol, or oil. Carriers which may be used include petroleum jelly, lanolin, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6): 318 (1986)) and typically take the form of an optionally buffered aqueous solution of the prodrug. Suitable formulations comprise citrate or bis\tris buffer (pH 6) or ethanol/water and contain from 0.1 to 0.2M active ingredient.

7.6 Methods of Administration and Treatment

The natriuretic compound conjugates and pharmaceutical formulations of the invention exhibit one or more improved characteristics relative to the unmodified (unconjugated) biologically active natriuretic compound, the addition of the modifying moiety can protect the biologically active natriuretic compound, from degradation in various environments (such as the gastrointestinal tract (GI tract)), such that less of it is degraded in the unmodified form than would be degraded in the absence of the modifying moiety in such environments. In particular, certain modified forms of the invention can be orally administered in a dosage that ultimately provides a pharmaceutically acceptable amount of the biologically active natriuretic compound in systemic circulation. That is to say, a sufficient amount of natriuretic compound can survive in the GI tract and enter the bloodstream such that the biologically active natriuretic compound is systemically present in a pharmacologically active amount sufficient to trigger production of cGMP. Preferably, the addition of the modifying moiety improves the delivery of orally administered unconjugated natriuretic compound into the bloodstream upon oral administration relative to the delivery of orally administered unconjugated natriuretic compound into the bloodstream. More preferably, the improvement of the delivery of active compound into the bloodstream for orally administered natriuretic compound conjugates is at least 2 times the delivery of orally administered unconjugated parent biologically active natriuretic compound, into the bloodstream. Still more preferably, the improvement of the delivery of active compound into the bloodstream for orally administered natriuretic compound conjugates is at least 3, 4, 5, 6, 7, 8, 9, 10, 15, 20, 25, 30, 40, 50, 60, 70, 80, 90, 100, 150, 200, 300, 400, or 500 times the delivery of orally administered unmodified (unconjugated) biologically active natriuretic compound, into the bloodstream. Thus, administration of the natriuretic compound conjugates of the invention can provide greater bioavailability of the biologically active natriuretic compound relative to administration of unmodified biologically active natriuretic compound. An oral route of administration (instead of by continuous intravenous infusion for days in a hospital setting) may reduce hospital costs associated with other CHF therapies and/or expand the therapeutic use of hBNP to include early stage and chronic CHF as well as acute CHF.

Thus, in one aspect, the invention provides a method of treating a disease condition susceptible to treatment using a natriuretic peptide compound by administering to a subject in need thereof a therapeutically effective amount of a natriuretic compound conjugate of the invention. The natriuretic compound conjugate may be suitably administered by a variety of routes, including for example, parenteral and enteral routes. Examples of preferred routes include oral, subcutaneous, sublingual, buccal, nasal, intravenous and intramuscular.

Several approaches may be used in the use of the present natriuretic compound conjugates for the treatment of heart failure. For example, it is envisioned that the natriuretic compound conjugates can be presented as a monotherapy, preferably in an oral dosage form alone. Alternatively, the natriuretic compound conjugates may be used together with more conventional therapeutic agents as part of a combination therapy. The primary categories of drugs that are currently used include the following:

Diuretics—alleviate the fluid accumulation and resultant stretching of the heart associated with CHF.

Vasodilators—expand arteries and veins, allowing for increased blood flow.

Inotropic agents—increase the force of contraction of cardiac muscle.

Digitalis drugs—increase force of contraction of the heart and reduce heart rate.

Angiotensin converting enzyme (ACE) inhibitors—inhibit the production of the vasoconstrictor angiotensin II in the last stage of its synthesis.

Angiotensin receptor blockers (ARB's)—permit angiotensin to be produced, but inhibit its arterial activity.

Calcium channel blockers—inhibit calcium influx, resulting in vascular and smooth muscle relaxation.

Nitrates—relax smooth muscles and dilate veins and arteries.

Beta-blockers—block the action of catecholamines, resulting in less stress on the heart and lower force and rate of contraction.

Some of the advantages of the natriuretic compound conjugates can be considered first in relation to the other approaches to treat CHF and compared to the current use of the natriuretic peptide in its unmodified form, that is continuously infused. The oral natriuretic compound conjugates of the invention exhibit natriuretic and diuretic properties that may be expected to relieve congestion through the elimination of sodium and excess water. Such functions are currently addressed with diuretics and potassium supplements. The natriuretic compound conjugates of the invention are expected to possess vascular and myocardial relaxant properties that are currently effected using vasodilators, calcium channel blockers, and nitrates. The natriuretic compound conjugates of the invention are expected to inhibit the renin-angiotensin-aldosterone system (RAAS) currently effected using ACE inhibitors and ARB's. Moreover, the natriuretic compound conjugates are expected to lack the negative effects and risk of sudden death associated with the inotropic and digitalis drugs. The natriuretic compound conjugates may have many, if not all, of the benefits of several groups of cardiovascular drugs while having a reduced amount of or lacking the negative effects of conventional therapies.

The natriuretic compound-conjugates of the invention also have advantages over NATRECOR® (nesiritide, made by Scios, Inc., Sunnyvale, Calif.). Some of the advantages can be attributed to the enhanced pharmacokinetic profile that amphiphilic oligomers according to embodiments of the present invention provide. For example, resistance to degradation by proteases (such as NEP) may lead to a longer circulating half-life as compared to the unconjugated peptide. A significant advantage may result from the ability of BNP or ANP conjugated with such oligomers to be delivered orally. For instance, NATRECOR® is dosed by continuous infusion over 48 hours and carries a high cost per dose plus hospital costs. An oral hBNP compound conjugate according to embodiments of the present invention may be dosed at an overall lower cost, and may be available on an outpatient basis and may be self-administered. Instead of being limited to use with inpatients having the most acute cases of CHF, oral conjugates according to embodiments of the present invention can be used for those suffering with the gradual onset of chronic CHF. The ease of administration, reduced demand on hospital resources, and/or lower cost support the utility of an the natriuretic compound conjugates as a preventative therapy, self administered (e.g., at home) for those patients who are at high risk of heart failure. Oral preparations of the hBNP compound conjugate according to embodiments of the present invention are thus expected to have many, if not all the benefits of Natrecor®, with the advantages of an improved pharmacokinetic profile, greater ease of administration, reduced hospitalization expenses, expansion of indication to include chronic CHF, and/or utility in early-stage cardiovascular disease.

Subjects taking or inclined to take the parent natriuretic compound can alternatively (or additionally) take the natriuretic compound preparation described herein. For example, patients suffering from disorders that are conventionally treated using a parenterally administered natriuretic compound, such as NATRECOR®, can be treated using an effective amount of the modified form of that agent described herein. Advantageously, where such agents were previously only administrable via injection or intraveneous administration, the natriuretic compound can be administered via inhalation or, more preferably, oral administration.

In one embodiment, the invention provides a method of delivering a biologically active agent to a subject, wherein the biologically active agent is orally administered as a component of a modified natriuretic compound of the invention, a portion of the orally administered natriuretic compound survives intact in the GI tract and traverses the intestinal wall to enter the bloodstream, and after leaving the GI tract, some or all of the natriuretic compound is hydrolyzed in vivo to yield a pharmaceutically acceptable amount of the biologically active agent. The hydrolysis may, for example, take place in the bloodstream or in the liver. In this method, the modified forms of the natriuretic compound enhances the oral bioavailability of the orally administered biologically active agent relative to the oral bioavailability of a corresponding orally administered unconjugated biologically active agent.

The effective amount of any natriuretic the use of which is in the scope of present invention, will vary somewhat from agent to agent, and patient to patient, and will depend upon factors such as the age and condition of the patient and the route of delivery. Such dosages can be determined in accordance with routine pharmacological procedures known to those skilled in the art. As a general proposition, a dosage from about 0.1 to about 50 mg/kg will have therapeutic efficacy, with all weights being calculated based upon the weight of the patient. Toxicity concerns at the higher level may restrict intravenous dosages to a lower level such as up to about 10 mg/kg, with all weights being calculated based upon the weight of the active base. A dosage from about 10 mg/kg to about 50 mg/kg may be employed for oral administration. Typically, a dosage from about 0.5 mg/kg to 5 mg/kg may be employed for intramuscular injection. The frequency of administration is usually one, two, or three times per day or as necessary to control the condition. The duration of treatment depends on the type of condition being treated and may be for as long as the life of the patient.

Suitable subjects to be treated according to the present invention include, but are not limited to, avian and mammalian subjects, preferably mammalian. Mammals according to the present invention include but are not limited to canine, felines, bovines, caprines, equines, ovines, porcines, rodents (e.g. rats and mice), lagomorphs, primates, humans, and the like, and encompass mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and include birds in ovo.

7.7 Assays

Natriuretic peptide analogs of the invention may induce the cardiovascular, renal, and/or endocrine effects that are associated with the native peptide. Cell based assays may be used to show which conjugates are proficient agonists of the human natriuretic peptide receptor A, leading to the suitable production of cGMP. Biochemical assays may be used to show which conjugates offer the suitable protection against proteolytic enzymes. In vivo experiments may be used to show which conjugates afford a desirable bioavailability. Leading conjugates can be tested in established dog models. Desirable candidates may be subjected to detailed pharmacokinetic, pharmacodynamic, and toxicity studies in rats and dogs. BNP conjugates according to embodiments of the present invention will be useful for the treatment of early-stage, chronic, and acute congestive heart failure.

The novel peptides and novel conjugates of the invention can be tested for agonist activity at the human natriuretic peptide receptor A (NPR-A) in vitro. The vasorelaxant, natriuretic, and diuretic properties of BNP are ascribed to a secondary messenger, cyclic GMP (cGMP). The production of cGMP is accomplished by guanylate cyclase, an enzyme that is activated when BNP binds to NPR-A. cGMP production can be measured in cultures of human aortic endothelial cells that endogenously express NPR-A. Thus, the relative activity of the natriuretic compound conjugates and natriuretic peptide analogs of the invention can be determined by the level of cGMP production in these cells.

The conjugates of the invention can be tested for increased resistance to proteases. In general, drugs that are delivered orally are subjected to digestive enzymes such as pepsin, trypsin, and/or chymotrypsin. In the case of peptide drugs, these enzymes may be particularly problematic. However, peptide conjugation has been shown to increase resistance to these enzymes. Digestive enzyme cocktails can be used to test for increased resistance of hBNP conjugates and other conjugates of the invention to proteases of the digestive tract. Natriuretic compound conjugates are preferably less susceptible to proteolytic degradation than corresponding unconjugated natriuretic compounds, i.e., the conjugates digest more slowly than the corresponding unconjugated compound.

The conjugates can be tested for oral bioavailability. Oral bioavailability of the conjugates can be tested in rats, for example. The conjugates can be administered to the gastrointestinal tract by oral gavage and the presence of hBNP conjugates in the bloodstream can be assayed using available radioimmunoassay procedures. Conjugates according to embodiments of the present invention may preferably be orally and/or perorally available, i.e., a therapeutically significant amount of the conjugate can be delivered by the oral and/or peroral routes.

The conjugate may retain some or all of the activity of native natriuretic peptide (e.g., hBNP) with the additional benefits of oral administration. Such a compound may lower costs associated with treatment of acute CHF and/or expand the applicability of this therapeutic to include early stage and chronic CHF.

In one aspect, the invention provides a method of generating data comprising assaying a natriuretic compound assaying a natriuretic compound conjugate of the invention or a series of such natriuretic compound conjugates, and compiling data resulting from such assaying. The data itself is therefore understood to constitute yet another embodiment of the invention, as well as the use of this data.

8.8 Branched Oligomeric Modifying Moieties

The present invention also provides several PEG linear and branched, amine, microPAGylated and alkyl-PEG modifying moieties.

7.7.1 Branched Oligomeric Modifying Moiety Formulas

The present invention provides a compound having a formula:

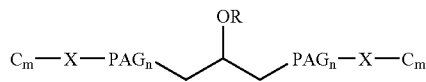

(Formula VI)

wherein R is —H, —C(O)OH or an activating moiety, such as C(O)X' (where $X^1$ is a halide (e.g., Cl, Br) or p-nitrophenol), or

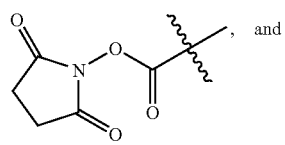

, and

C, m, X, PAG, and n are as described above for Formula I.

The present invention also presents a compound having a formula:

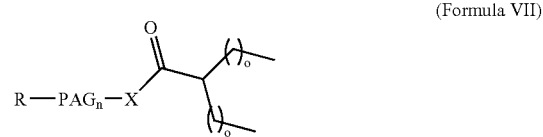

(Formula VII)

wherein R is H (it will be understood that the atom in PAG coupled to R is O, and therefore that the terminating moiety is OH), C(O)OH or an activating moiety, such as C(O)X' (where X' is a halide (e.g., Cl, Br) or p-nitrophenol), or

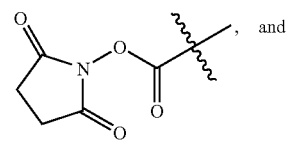

, and

PAG, n, X, and o are as described above for Formula II.

In yet another embodiment, a compound is provided having a formula:

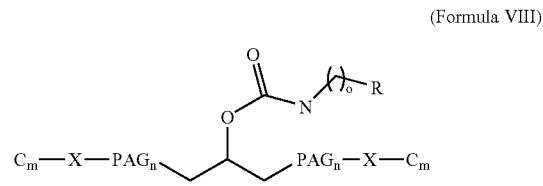

(Formula VIII)

wherein R is —H, —OH, —C(O)OH or an activating moiety, such as C(O)X' or OC(O)X' (where X' is a halide (e.g., Cl, Br) or p-nitrophenol), or

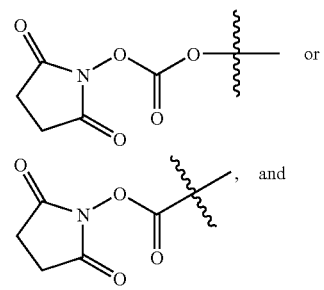

or

, and

C, m, X, PAG, n and o are as described above for Formula III.

In another aspect, the modifying moiety may have a formula:

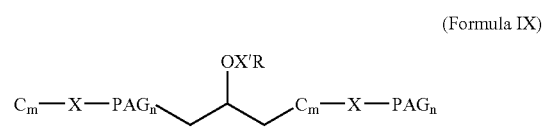

(Formula IX)

wherein R is H, C(O)OH or an activating moiety, such as C(O)X" (where X" is a halide (e.g., Cl, Br) or p-nitrophenol), or

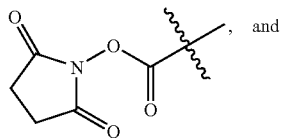, and

X' is

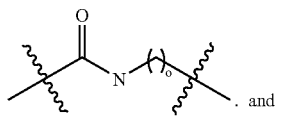, and

C, m, PAG, n, and X are as described above for Formula IV.

In another aspect, the modifying moiety may have a formula:

(Formula X)

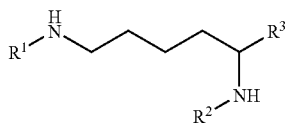

wherein $R^3$ is —OH, —C(O)OH or an activating moiety, such as

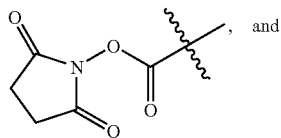, and $R^1$ and $R^2$ are each independently selected and are any of Formulas I, II, III or IV above.

7.7.2 Methods of Making Oligomeric Modifying Moieties

The present invention also provides several methods for preparing the modifying moieties disclosed herein. A method of making a compound of the formula:

(Formula XI)

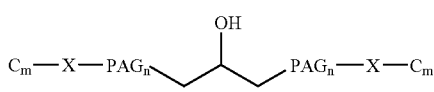

is provided, wherein C, m, X, PAG, and n are as described above for Formula I. This method may be described as comprising the steps of reacting a compound of formula:

with a compound of formula:

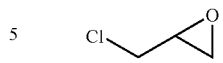

(note that Cl may be replaced with another leaving group, such as another halide) in the presence of a base and a solvent to yield a product of a formula:

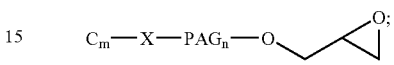

reacting the product a with a compound of formula:

in the presence of a Lewis acid and a solvent to yield:

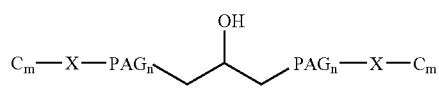

wherein C, m, X, PAG, and n as defined above for Formula I. Cl may be replaced with another halogen, such as Br. By way of example, the base may be further defined as NaH, and the solvent may be further defined as tetrahydrofuran. The Lewis acid to be used in this method may also be further defined as $BF_3OEt_2$.

Another method of the invention is also disclosed for making a compound of the formula:

(Formula XII)

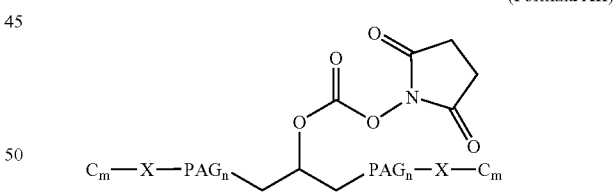

wherein C, m, X, PAG and n are as defined above for Formula I. This method may be further defined as comprising the steps of reacting a product

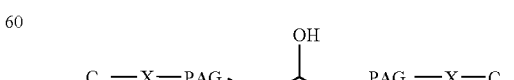

wherein C, m, X, PAG, and n defined as above, with paranitrochloroformate or disuccimidyl carbonate.

Yet another embodiment of the invention is provided in a method of making a compound of the formula:

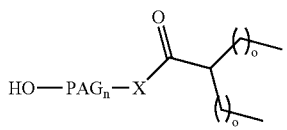

wherein PAG, n, X, and o are as defined above for Formula II. This method may be further described as comprising the steps of reacting a compound of formula:

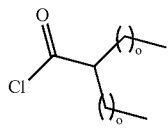

(note that Cl may be replaced with another leaving group, such as another halide) wherein o is as defined above for Formula I, with a compound of formula:

HO-PAG$_n$-X wherein X is —NH or —OH, in a solvent, to yield a compound of formula:

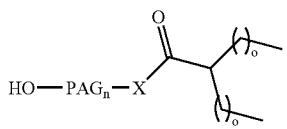

wherein PAG, n, X, and o are as defined above for Formula II.

The invention also provides a method of making a compound of the formula:

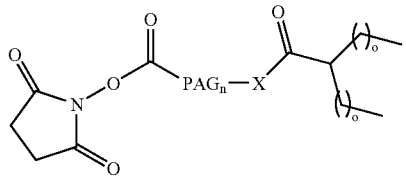

(Formula XIII)

wherein PAG, n, X, and o are as defined above for Formula II. This method may be described as comprising the steps of activating a product

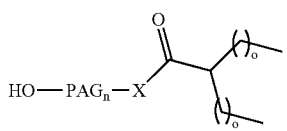

(wherein PAG, n, X, and o are defined above for Formula II using an activating agent, such as disuccinimidyl carbonate, paranitrochloroformate, phosgene and N-hydroxysuccinimide.

Yet another embodiement of the invention provides a method of making a compound of the formula:

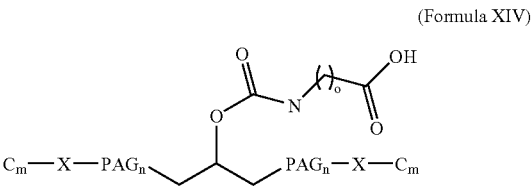

(Formula XIV)

wherein C, m, X, PAG, n, and o are as defined above for Formula III. This method may be described as comprising the steps of reacting the product identified here as Formula XII above with a compound of formula:

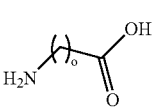

in the presence of a base in a solvent, wherein o is as defined above for Formula III. In preferred embodiments of this method, the base is K$_2$CO$_3$ and the solvent is an aqueous and/or organic solvent.

In addition, the invention further provides a method of making a compound of the formula:

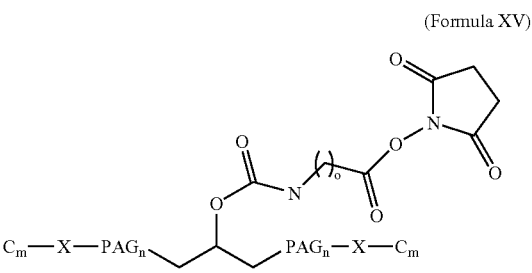

(Formula XV)

wherein C, m, PAG, n, and o are as defined above for Formula III. The method generally comprises reacting a compound produced according to the method of preparing the Formula XIV as defined above, with an activating agent such as N-hydroxysuccinimide.

8. EXAMPLES

The following examples have been included to illustrate models of the invention. Certain aspects of the following examples are described in terms of techniques and procedures found to demonstrate the best mode of practicing the invention. In light of the present disclosure and the general level of skill known in the relevant art of the present invention, those of skill will appreciate that the following examples are intended to be exemplary only and that numerous changes, modifications, and alterations can be employed without departing from the scope of the invention.

8.1 Activation of PEG-Alkyl Modifying Moiety (carbonic acid 2,5-dioxo-pyrrolidin-1-yl ester 2-[2-(2-{2-[2-(2-hexadecyloxy-ethoxy)-ethoxy]-ethoxy}-ethoxy)-ethoxy]-ethyl ester (II))

Hexaethyleneglycol monohexadecyl ether, I (0.202 g, 0.4 mmol) was dissolved in acetonitrile (5 mL) and disuccinimidyl carbonate (DSC, 0.157 g, 0.6 mmol) was added. Then triethylamine (0.12 g, 1.2 mmol) was added dropwise and after 10 min the reaction mixture became clear. Reaction was stirred overnight at RT. After stirring for ~16 hours, the crude reaction was evaporated to dryness and then dissolved in saturated NaHCO$_3$ (10 mL), washed with ethyl acetate (2×20 mL), dried over MgSO$_4$, and evaporated to dryness. The crude product mixture was purified via column chromatography (silica, EtOAc/methanol, 10:1) to yield 0.258 g (81%) of the title compound II as an oil. ESI MS: m/e 648.84 (M+H)$^+$.

To a cooled solution of 2-(2-Amino-ethoxy)-ethanol (575 g, 5.47 mmol) in 10 ml dichloromethane, 2-hexyl-decanoyl chloride II (750 mg, 2.74 mmol) was added drop wise over a period of thirty minutes. After the addition was complete, the temperature of the reaction mixture temperature was increased to 25° C. Reaction was stirred overnight at room temperature. After stirring for ~20 hours, the crude reaction was acidified with 1NHCl and diluted with 10 ml H$_2$O. The reaction mixture was then extracted with dichloromethane. The organic layer was then washed with 1N HCl, water, dried over MgSO$_4$, filtered and concentrated. Crude material was purified by flash chromatography (silica, gradient elution: 2-5% methanol in CHCl$_3$), to yield 902 mg (96%) of the monodispersed compound III as an off-white solid. ESI MS: m/e 344.54 (M+H)$^+$.

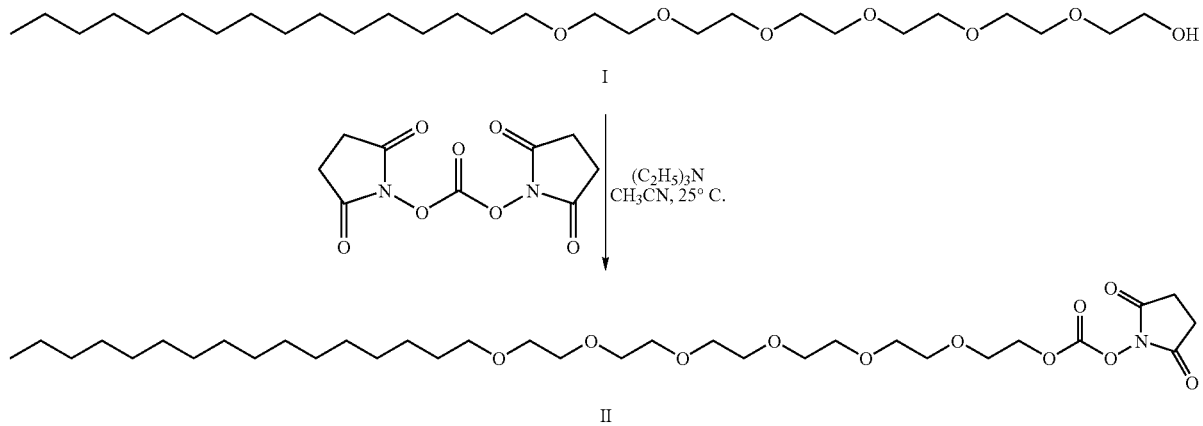

8.2 Synthesis of Branched PEG Amine Modifying Moiety (carbonic acid 2,5-dioxo-pyrrolidin-1-yl ester 2-[2-(2-hexyl-decanoylamino)-ethoxy]-ethyl ester (IV))

Thionyl chloride (5.5 gm, 46.6 mmol) was added drop wise over a period of thirty minutes to a solution of 2-Hexyldecanoic acid I (10 gm, 38.9 mmol) in 100 mL carbon tetrachloride. After the addition was complete, the reaction mixture was refluxed for 3 hours. After the reaction was complete, the carbon tetrachloride was removed by distillation and the reaction mixture was concentrated to get crude acid chloride. The crude acid chloride was purified by fractional distillation to obtain II as a clear liquid (10.1 gm, 91%). ESI MS: m/e 275.87 (M+H)$^+$.

Monodispersed branched C16-PEG2 III (200 mg, 0.58 mmol) was dissolved in acetonitrile (5 mL) and disuccinimidyl carbonate (DSC, 0.224 g, 0.87 mmol). Then triethylamine (0.118 g, 1.17 mmol) was added dropwise and after 10 min the reaction mixture became clear. Reaction was stirred at room temperature overnight. After stirring for ~16 hours, the crude reaction was evaporated to dryness and then dissolved in saturated NaHCO$_3$ (10 mL), washed with ethyl acetate (2×20 mL), dried over MgSO$_4$, and evaporated to dryness. The residue was purified via column chromatography (silica, EtOAc/methanol, 10:1) to yield 0.206 g (74%) of the oil IV (0.206 g, 74% yield). ESI MS: m/e 485.63 (M+H)$^+$.

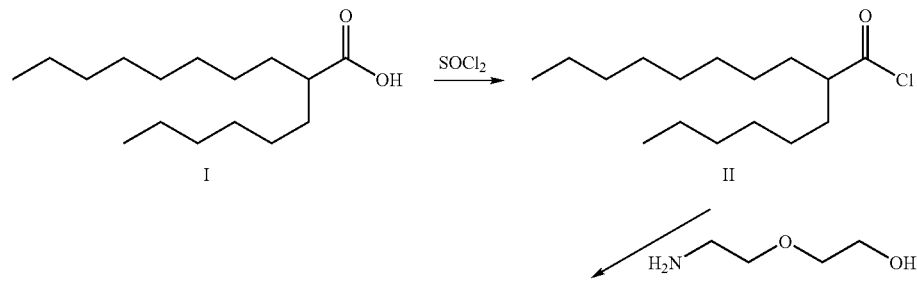

-continued

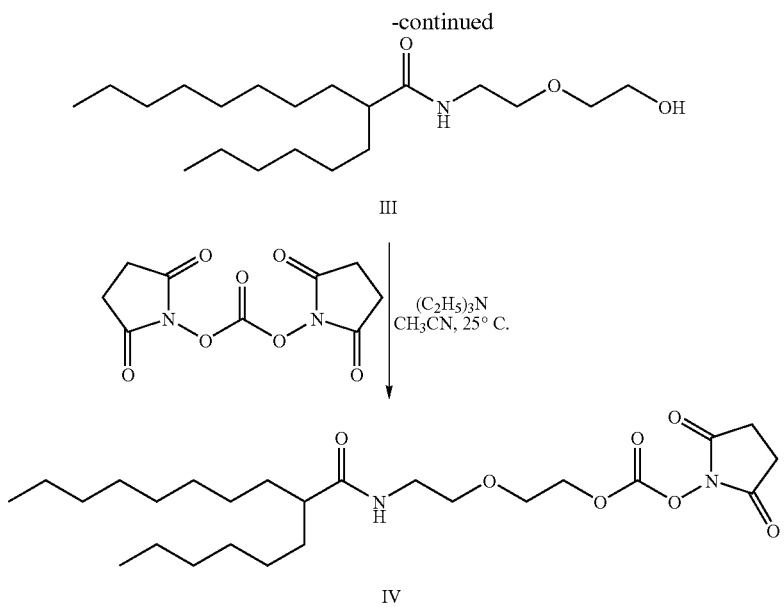

8.3 Synthesis and Activation of PEG-Alkyl Modifying Moiety (16-(2-{2-[2-(2-{2-[2-(2-Methoxy-ethoxy)-ethoxy]-ethoxy}-ethoxy)-ethoxy]-ethoxy}-ethoxy)-hexadecanoicacid 2,5-dioxo-pyrrolidin-1-yl ester)

To a solution of monodispersed 16-bromo-hexadecanoic acid (15.3 g, 45 mmol) in ethanol (300 mL) was added H₂SO₄ (1.5 mL, 31.25 mmol) and the reaction was stirred for 48 h. The crude reaction mixture was diluted with water and extracted with dichlormethane (2×300 mL). The organic layer was washed with H₂O (300 mL), sat. NaHCO₃ (2×300 mL), H₂O (300 mL), dried MgSO₄, and evaporated to dryness to afford a off-white solid II (16.03 g, 98% yield).

To a solution of monodispersed heptaethylene glycol monomethyl ether (8.51 g, 25 mmol) in THF (250 mL) was added potassium t-butoxide (3.1 g, 27.5 mmol, small portions over ~30 min). The reaction mixture was then stirred for 1 h and then II (10 g, 27.5 mol) dissolved in THF (90 mL) was added dropwise and the reaction mixture was stirred overnight. The crude reaction mixture was filtered through Celite (washed CH₂Cl₂, ~200 mL) and evaporated to dryness to afford oil. The crude oil was purified via flash chromatography (silica, gradient elution: 2-5% methanol in CHCl₃) to give clear yellow oil IV, 2.48 g (16%).

To the oil of the monodispersed compound IV (2.22 g, 3.56 mmol) was added 1N NaOH (50.0 mL), 25 mL methanol, 25 mL ethanol and the reaction mixture was stirred for 24 h. The crude reaction mixture was concentrated, acidified (pH~2), saturated with NaCl, and washed CH₂Cl₂ (3×75 mL). The organic layers were combined, washed sat. NaCl, dried MgSO₄, and evaporated to dryness to afford the monodispersed compound V as a white solid. The crude solid was purified via flash chromatography (silica, ethyl acetate) to give V, 858 mg (40%).

Monodispersed mPEG7-C16-acid V (324 mg, 544 mmol) was dissolved in 15 ml of anhydrous methylene chloride and then solution of N-hydroxysuccinimide (94 mg, 816 mmol) and 1-ethyl-3-(3'-dimethylaminopropyl)carbodiimide. HCl (EDCl.HCl, 156 mg, 816 mmol) in anhydrous methylene chloride added. Reaction was stirred for 24 hours, then washed with 1N HCl, water, dried over MgSO₄, filtered and concentrated. Crude material was purified by flash chromatography (silica, gradient elution: 2-5% methanol in CHCl₃), to afford monodispersed activated MPEG7-C16 VI as a clear oil (290 mg, 77%).

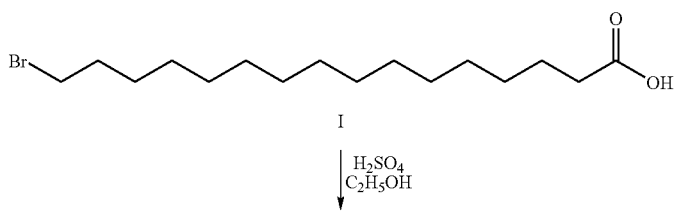

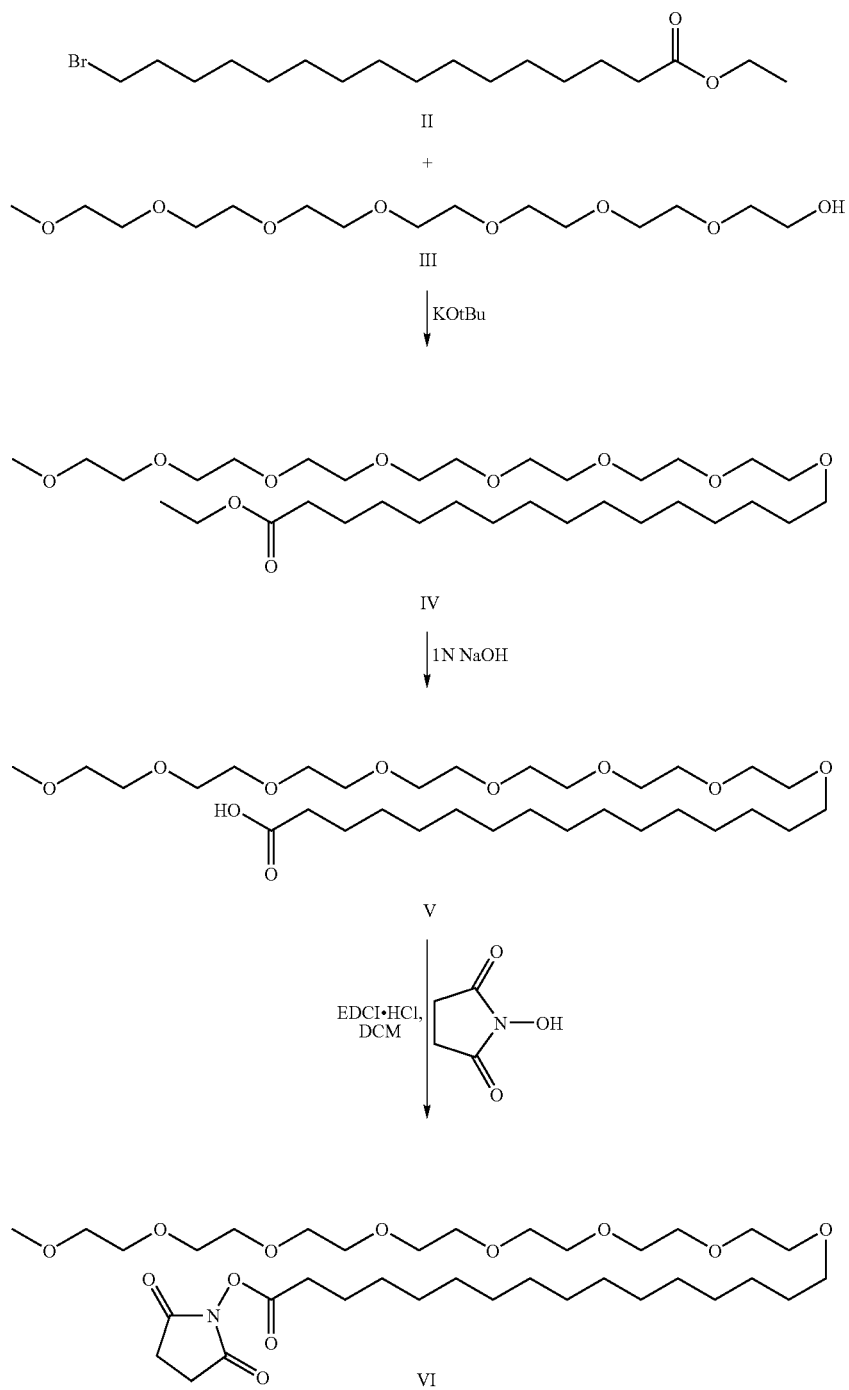

8.4 Activation of PEG-Alkyl Modifying Moiety (12-(2-{2-[2-(2-{2-[2-(2-Methoxy-ethoxy)-ethoxy]-ethoxy}-ethoxy)-ethoxy]-ethoxy}-ethoxy)-dodecanoic acid 2,5-dioxo-pyrrolidin-1-yl ester)

Monodispersed mPEG7-C12-acid 1 (500 mg, 0.78 mmol) was dissolved in 20 ml of anhydrous methylene chloride and then solution of N-hydroxysuccinimide (160 mg, 1.39 mmol) and 1-ethyl-3-(3'-dimethylaminopropyl)carbodiimide. HCl (EDCl.HCl, 233 mg, 1.390 mmol) in anhydrous methylene chloride added. Reaction was stirred for 24 hours, then washed with 1N HCl, water, dried over MgSO$_4$, filtered and concentrated. Crude material was purified by flash chromatography (silica, gradient elution: 2-5% methanol in CHCl$_3$), to afford monodispersed activated MPEG7-C16 VI as a clear oil (370 mg, 62%).

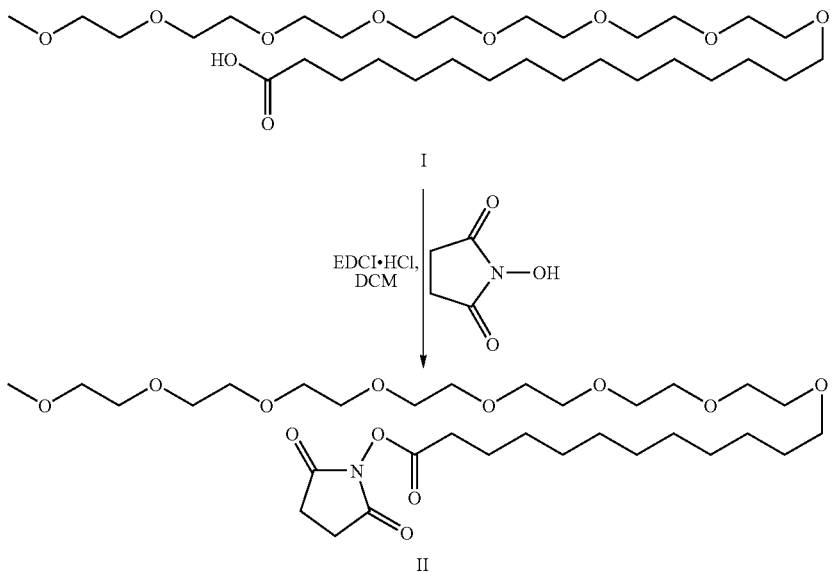

8.5 Synthesis of PEG Modifying Moiety (carbonic acid 2,5-dioxo-pyrrolidin-1-yl ester 2-methoxy-ethyl ester)

Monodispersed branched MPEG1 I (200 mg, 2.63 mmol) was dissolved in acetonitrile (20 mL) and disuccinimidyl carbonate (DSC, II, 1.00 g, 3.94 mmol) was added. Then triethylamine (0.399 g, 3.94 mmol) was added dropwise and after 10 min the reaction mixture became clear. Reaction was stirred overnight at RT. After stirring for ~16 h, the crude reaction was evaporated to dryness and then dissolved in sat. NaHCO$_3$ (20 mL), washed ethyl acetate (2×50 mL), dried MgSO$_4$, and evaporated to dryness. Column chromatography (silica, EtOAc/MeOH, 10:1) afforded the solid III (0.346 g, 60% yield). ESI MS: m/e 218.09 (M+H)$^+$.

8.6 Synthesis of Hydrolysable MicroPAGylated Modifying Moiety (hexanoic acid 2-(2,5-dioxo-pyrrolidin-1-yloxycarbonyloxy)-ethyl ester)

Monodispersed branched C6-PEG1 I (100 mg, 0.625 mmol) was dissolved in acetonitrile (10 mL) and disuccinimidyl carbonate (DSC, II, 0.240 g, 0.936 mmol) was added. Then triethylamine (0.095 g, 0.936 mmol) was added dropwise and after 10 min the reaction mixture became clear. Reaction was stirred overnight at RT. After stirring for ~16 h, the crude reaction was evaporated to dryness and then dissolved in sat. NaHCO$_3$ (10 mL), washed ethyl acetate (2×20 mL), dried MgSO$_4$, and evaporated to dryness. Column chromatography (silica, EtOAc/MeOH, 10:1) afforded an off-white solid III (0.146 g, 78% yield). ESI MS: m/e 302.29 (M+H)$^+$.

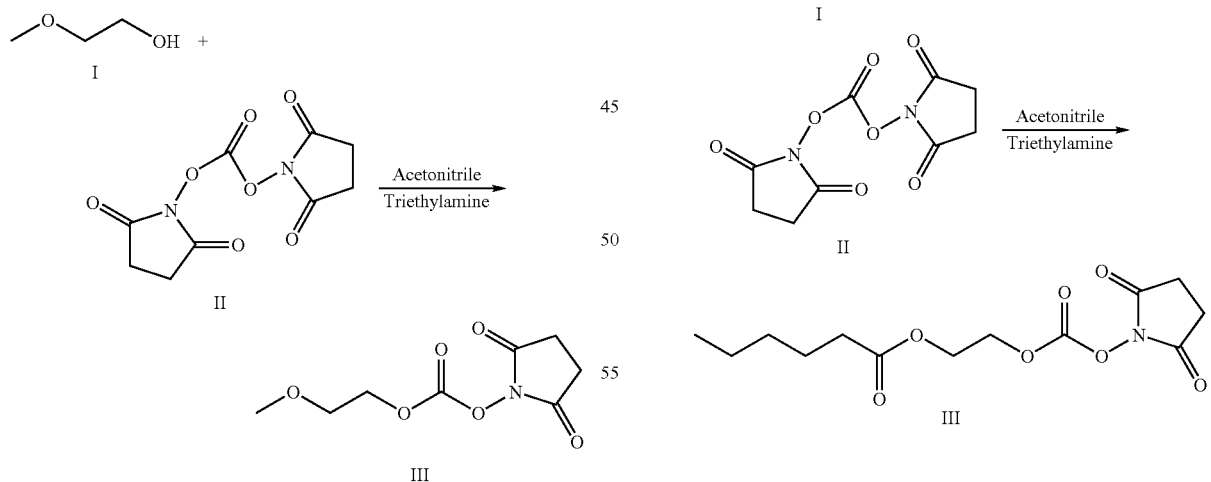

8.7 Synthesis of Linear mPEG Modifying Moiety (carbonic acid 2,5-dioxo-pyrrolidin-1-yl ester 2-(2-methoxy-ethoxy)-ethyl ester)

Monodispersed branched MPEG2 I (470 mg, 3.91 mmol) was dissolved in acetonitrile (20 mL) and disuccinimidyl carbonate (DSC, II, 1.50 g, 5.87 mmol) was added. Then triethylamine (0.594 g, 5.87 mmol) was added dropwise and after 10 min the reaction mixture became clear. Reaction was stirred overnight at RT. After stirring for ~16 h, the crude reaction was evaporated to dryness and then dissolved in sat. NaHCO$_3$ (20 mL), washed ethyl acetate (2×50 mL), dried MgSO$_4$, and evaporated to dryness. Column chromatography (silica, EtOAc/MeOH, 10:1) afforded the solid III (0.632 g, 62% yield). ESI MS: m/e 262.23 (M+H)$^+$.

8.9 Synthesis Linear PEG Modifying Moiety (carbonic acid 2,5-dioxo-pyrrolidin-1-yl ester 2-[2-(2-methoxy-ethoxy)-ethoxy]-ethyl ester)

Monodispersed branched MPEG3 I (200 mg, 1.21 mmol) was dissolved in acetonitrile (20 mL) and disuccinimidyl carbonate (DSC, II, 0.468 g, 1.82 mmol) was added. Then triethylamine (0.184 g, 1.82 mmol) was added dropwise and after 10 min the reaction mixture became clear. Reaction was stirred overnight at RT. After stirring for ~16 h, the crude reaction was evaporated to dryness and then dissolved in sat. NaHCO$_3$ (20 mL), washed ethyl acetate (2×50 mL), dried MgSO$_4$, and evaporated to dryness. Column chromatography (silica, EtOAc/MeOH, 10:1) afforded the solid III (0.206 g, 55% yield). ESI MS: m/e 306.11 (M+H)$^+$.

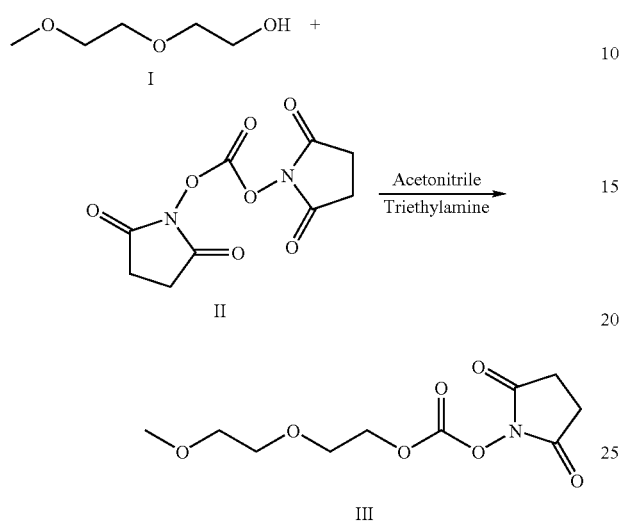

8.8 Synthesis of Hydrolysable MicroPAGylated Modifying Moiety (dodecanoic acid 2-[2-(2,5-dioxo-pyrrolidin-1-yloxycarbonyloxy)-ethoxy]-ethyl ester)

Monodispersed branched C12-PEG2 I (200 mg, 0.69 mmol) was dissolved in acetonitrile (10 mL) and disuccinimidyl carbonate (DSC, II, 0.265 g, 1.035 mmol) was added. Then triethylamine (0.104 g, 1.035 mmol) was added dropwise and after 10 min the reaction mixture became clear. Reaction was stirred overnight at RT. After stirring for ~16 h, the crude reaction was evaporated to dryness and then dissolved in sat. NaHCO$_3$ (10 mL), washed ethyl acetate (2×20 mL), dried MgSO$_4$, and evaporated to dryness. Column chromatography (silica, EtOAc/MeOH, 10:1) afforded the oil III (0.247 g, 83% yield). ESI MS: m/e 430.50 (M+H)$^+$.

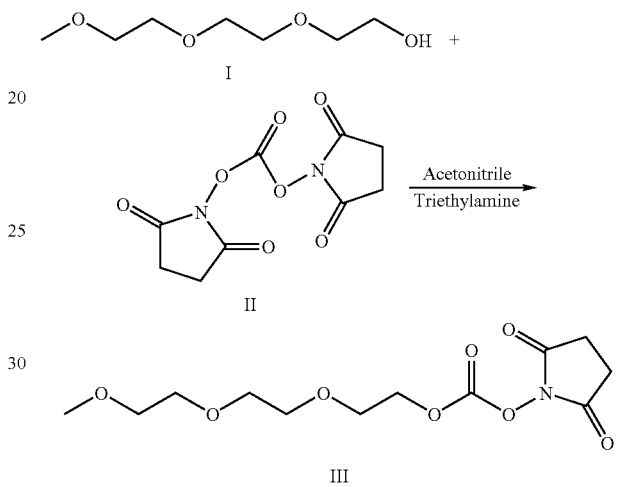

8.10 Synthesis of Hydrolysable MicroPAGylated Modifying Moiety (hexanoic acid 2-{2-[2-(2,5-dioxo-pyrrolidin-1-yloxycarbonyloxy)-ethoxy]-ethoxy}-ethyl ester)

Monodispersed branched C6-PEG3 I (200 mg, 0.80 mmol) was dissolved in acetonitrile (20 mL) and disuccinimidyl carbonate (DSC, II, 0.309 g, 1.209 mmol) was added. Then triethylamine (0.122 g, 1.209 mmol) was added dropwise and after 10 min the reaction mixture became clear. Reaction was

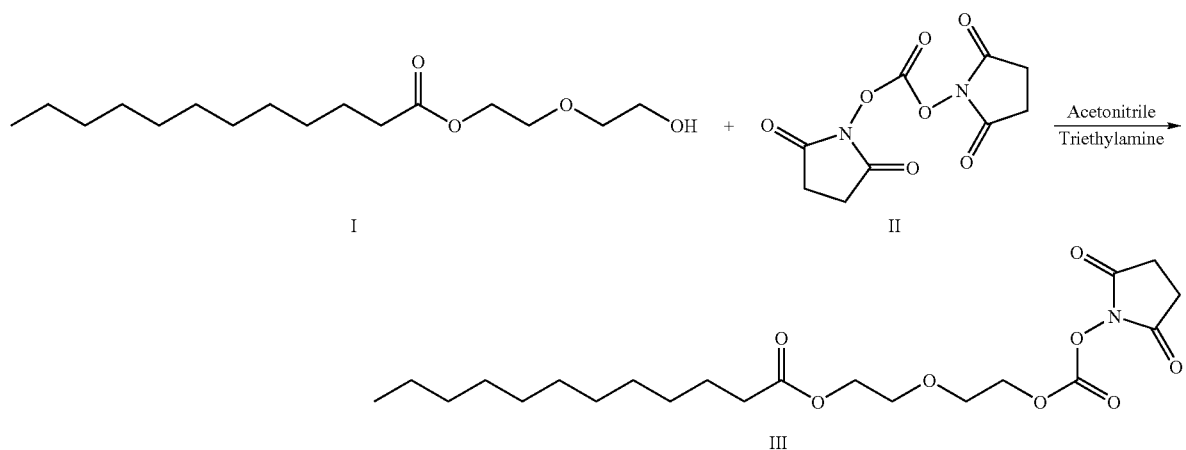

stirred overnight at RT. After stirring for ~16 h, the crude reaction was evaporated to dryness and then dissolved in sat. NaHCO₃ (10 mL), washed ethyl acetate (2×20 mL), dried MgSO₄, and evaporated to dryness. Column chromatography (silica, EtOAc/MeOH, 10:1) afforded the oil III (0.203 g, 64% yield). ESI MS: m/e 390.40 (M+H)⁺.

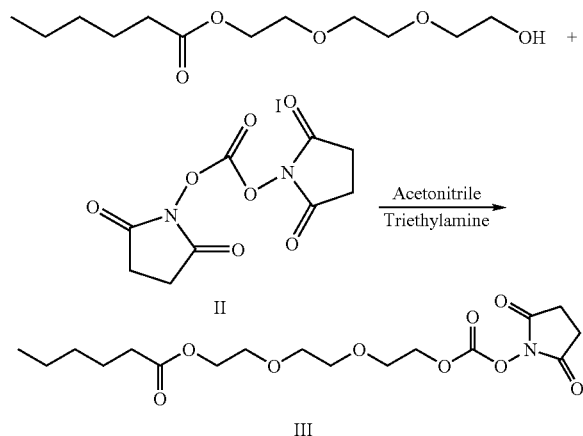

8.11 Synthesis of Benzyl Elimination Hydrolysable Oligomer (6-{2-[2-(2-{2-[2-(2-Methoxy-ethoxy)-ethoxy]-ethoxy}-ethoxy)-ethoxy]-ethoxy}-hexanoic acid 4-(4-nitrophenoxycarbonyloxymethyl)-phenyl ester)

Potassium tert-butoxide (3.64 g, 32.4 mmol) was dissolved in 250 mL THF. MPEG₆ alcohol (9.58 g, 32.3 mmol) in 10 mL THF was added. The solution was stirred for two hours The mesylate (7.0 g, 29.4 mmol) prepared from commercially available ethyl 6-hydroxy-hexanoate was dissolved in 15 mL THF and added to the PEG solution. The reaction was stirred at room temperature overnight. The reaction was quenched with 25 mL MeOH and filtered through a short pad of Celite. The filtrate was concentrated in vacuo and the residue purified by flash chromatography (EtOAc/2% MeOH) to give 3.19 g (25%) of I. ESI MS: m/e 461.07 (M+Na)⁺.

To hydrolyze the ethyl ester, 1.1 g (2.51 mmol) of I was treated with 35 mL 1 N NaOH. After six hours, the initially cloudy mixture had become a clear, yellow-colored solution. The mixture was saturated with NaCl and acidified with concentrated HCl until the pH was 2. The solution was extracted with 100 mL CH₂Cl₂. The organics were dried over Na₂SO₄, filtered and concentrated in vacuo to afford 0.80 g (78%) of the carboxylic acid II. ESI MS: m/e 411.07 (M+H)⁺, 433.10 (M+Na)⁺.

Carboxylic acid III (0.80 g, 1.95 mmol) was dissolved in 16 mL CH₂Cl₂ and placed under N₂. To the solution, 0.486 g (2.5 mmol) EDC and 0.288 g (2.5 mmol) N-hydroxysuccinimide (NHS) were added. After five hours, another 0.2 g EDC and 0.12 g NHS were added to drive reaction to completion. When TLC indicated that no unreacted carboxylic acid remained, the mixture was diluted with 60 mL CH₂Cl₂ and washed with cold 1 N HCl (1×100 mL), cold water (2×100 mL) and brine (3×100 mL). The organics were dried over Na₂SO₄, filtered and concentrated in vacuo to yield 0.71 g (71%) of III. ESI MS: m/e 508.17 (M+H)⁺, 530.07 (M+Na)⁺.

In 120 mL dry CH₂Cl₂, 4-hydroxybenzyl alcohol (2.93 g, 3.6 mmol) and 2.98 g (24.4 mmol) DMAP were dissolved. Compound III (1.2 g, (2.37 mmol) was dissolved in another 40 mL CH₂Cl₂ and added. The reaction was stirred at room temperature overnight. The mixture was washed with 1 N HCl (2×200 mL) and brine (2×200 mL). The organics were dried over Na₂SO₄, filtered and evaporated to dryness. The residue was purified via flash chromatography (silica, EtOAc/10% MeOH) to give 0.701 g (58%) of oligomer IV. ESI MS: 539.10 m/e (M+Na)⁺.

The oligomer IV (0.562 g, 1.09 mmol) was dissolved in 15 mL dry CH₂Cl₂. To this solution was added 0.23 mL (1.64 mmol) TEA and 0.329 g (1.64 mmol) p-nitro-phenylchloroformate. The reaction was stirred overnight at room temperature. The mixture was then diluted with a further 15 mL CH₂Cl₂ and washed with 15 mL 1 N HCl followed by 15 mL water. The organics were dried over MgSO₄, filtered and concentrated to dryness. The crude product was purified via flash chromatography (silica, gradient elution: 3/1 EtOAc/hexanes-EtOAc) to give 504 mg (74%) of the activated oligomer. ESI MS: m/e 682.72 (M+H)⁺, 704.72 (M+Na)⁺.

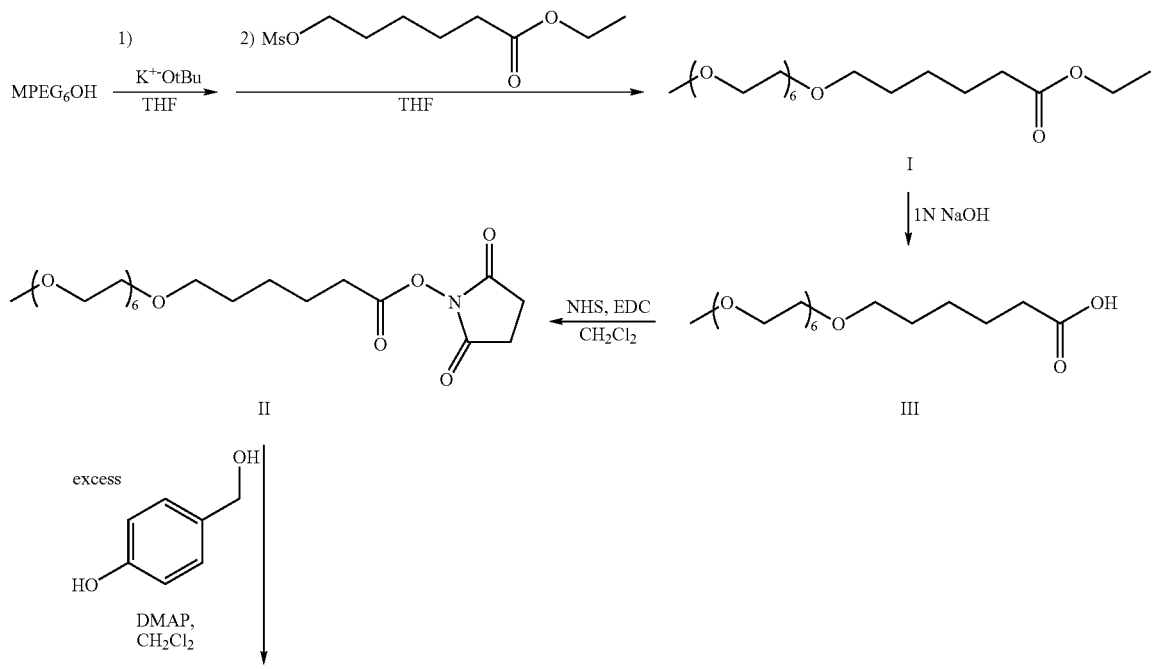

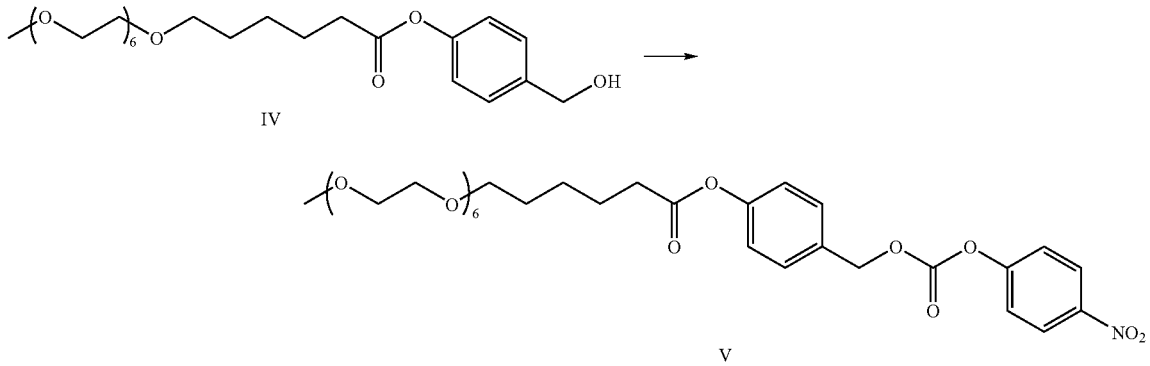

8.12 Synthesis of Aryl Carbamate Hydrolysable Modifying Moiety (carbonic acid 4-(6-{2-[2-(2-{2-[2-(2-methoxy-ethoxy)-ethoxy]-ethoxy}-ethoxy)-ethoxy]-ethoxy}-hexyloxy)-phenyl ester 4-nitro-phenyl ester)

MPEG$_6$ alcohol (10.0 g, 33.7 mmol) was dissolved in 40 mL dry CH$_2$Cl$_2$ and the resulting solution was cooled to 0° C. in an ice bath. TEA (5.64 mL, 40.5 mmol) was added and then 3.13 mL (40.5 mmol) methanesulfonyl chloride was added drop wise. The reaction was stirred for thirty minutes at 0° C. and then removed from the ice bath, allowed to come to room temperature and stirred overnight. The reaction mixture was diluted with more CH$_2$Cl$_2$ and washed with saturated NaHCO$_3$ and water. The organics were dried over MgSO$_4$, filtered and concentrated in vacuo to afford 12.4 g (98%) of MPEG$_6$ mesylate, I.

A solution of 1,6-hexanediol was prepared from 6.311 g of the diol (53.41 mmol) and 180 mL of dry THF. The solution was cooled to 0° C. and placed under a N$_2$ atmosphere. Potassium tert-butoxide (5.996 g, 53.41 mmol) was added to the solution and the resulting mixture was stirred for one hour. I (10.0 g, 26.7 mmol) in 30 mL THF was added to the mixture. All was stirred for a further 30 minutes at 0° C., then allowed to warm to room temperature and stirred overnight. The reaction mixture was filtered through Celite. The Celite was rinsed with CH$_2$Cl$_2$ and the combined filtrate was concentrated in vacuo. The residue was redissolved in CH$_2$Cl$_2$ and washed with water. The organics were dried over Na$_2$SO$_4$, filtered and evaporated to dryness. Purification by flash chromatography (silica, CHCl$_3$/10% MeOH). Some material was further purified by preparatory TLC (EtOAc/10% MeOH). Combined yield was 3.923 g (37%) of II.

II (3.923 g, 9.89 mmol) was dissolved in 16 mL dry CH$_2$Cl$_2$ and the resulting solution was cooled to 0° C. and placed under N$_2$. Triethylamine (1.65 mL, 11.9 mmol) was added and then 0.92 mL (11.9 mmol) methanesulfonyl chloride was added dropwise. The reaction was stirred at 0° C. for a further thirty minutes and then allowed to come to room temperature and stirred overnight. The reaction mixture was diluted with more CH$_2$Cl$_2$ and washed with saturated NaHCO$_3$ and water. The organics were dried over Mg$_2$SO$_4$, filtered and concentrated in vacuo to provide 4.25 g (91%) of mesylate III.

In a flask containing 50 mL dry THF, 5.001 g (24.97 mmol) of 4-benzyloxyphenol was dissolved. Potassium tert-butoxide (1.202 g, 9.989 mmol) was added and the resulting mixture was stirred for one hour at room temperature under an inert atmosphere. A solution of 3.950 g (8.324 mmol) of III in 20 mL THF was added. After a further 18 hours, the entire mixture was quenched with 10 mL MeOH and filtered through a short pad of Celite. The filtrate was concentrated in vacuo and the residue purified by flash chromatography (silica, EtOAc/MeOH 20:1) to provide 1.584 g (33%) of compound IV. ESI MS: m/e 579.16 (M+H)$^+$, 601.14 (M+Na)$^+$.

Compound IV (0.683 g, 1.18 mmol) was dissolved in 20 mL MeOH. To this solution was added a slurry of 136 mg of 5% Pd/C in MeOH. The entire mixture was placed under H$_2$ and stirred until TLC confirmed that all of the starting material had been consumed. The mixture was then filtered through Celite and the filtrate was evaporated to dryness to yield 412 mg (71%) of V. ESI MS: m/e 511.09 (M+Na)$^+$.

The oligomer V (0.605 g, 1.09 mmol) was dissolved in 15 mL dry CH$_2$Cl$_2$. To this solution was added 0.23 mL (1.64 mmol) TEA and 0.329 g (1.64 mmol) p-nitro-phenylchloroformate. The reaction was stirred overnight at room temperature. The mixture was then diluted with a further 15 mL CH$_2$Cl$_2$ and washed with 15 mL 1 N HCl followed by 15 mL water. The organics were dried over MgSO$_4$, filtered and concentrated to dryness. The crude product was purified via flash chromatography (silica, gradient elution: 3/1 EtOAc/hexanes-EtOAc) to give 491 mg (75%) of the activated oligomer. ESI MS: m/e 654.71 (M+H)$^+$, 675.71 (M+Na)$^+$.

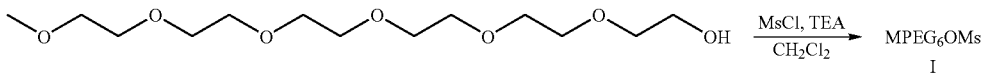

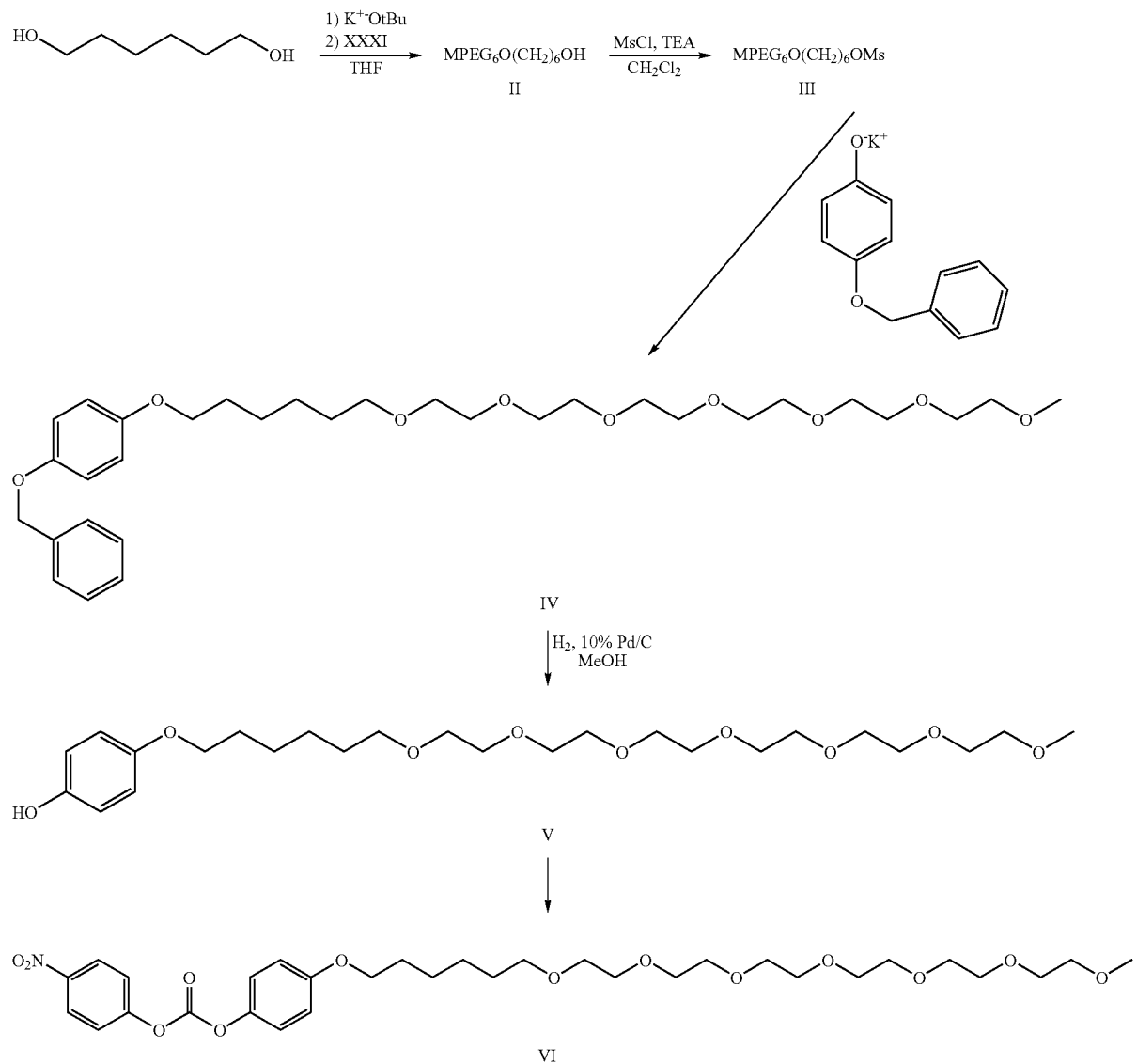

IV

V

VI

8.13 Methods For Activating Oligomeric Moieties

The present example describes methods by which a oligomeric moiety of the present invention may be activated.

8.13.1 Method 1—Activation Using DSC

Alkyl-PEG-OH, I (0.4 mmol, 1 eq.) was dissolved in acetonitrile (5 mL) and disuccinimidyl carbonate (DSC, 0.6 mmol, 1.5 eq.) was added. Then triethylamine (1.2 mmol, 1.5 eq.) was added dropwise and after 10 min the reaction mixture became clear. Reaction was stirred overnight at RT. After stirring for ~16 h, the crude reaction was evaporated to dryness and then dissolved in sat. NaHCO$_3$ (10 mL), washed ethyl acetate (2×20 mL), dried MgSO$_4$, and evaporated to dryness. Column chromatography (silica, EtOAc/MeOH, 10:1) afforded the activated oligomer II.

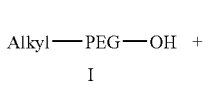

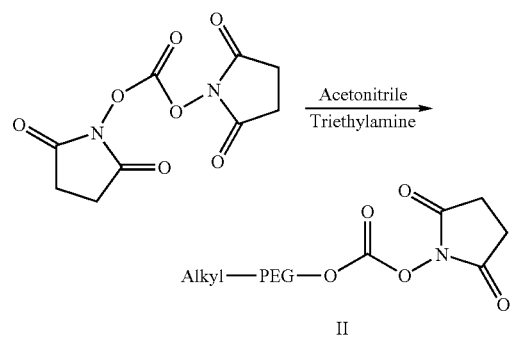

8.13.2 Method II: Activation Using NHS

MPEG-alkyl-acid I (0.544 mmol, 1.0 eq.) was dissolved in 15 ml of anhydrous methylene chloride and then solution of N-hydroxysuccinimide (0.816 mmol, 1.5 eq.) and I-ethyl-3-(3'-dimethylaminopropyl)carbodiimide. HCl (EDCI.HCl, 0.816 mmol, 1.5 eq.) in anhydrous methylene chloride added. Reaction was stirred for several hours, then washed with 1N HCl, water, dried over MgSO$_4$, filtered and concentrated. Crude material was purified by flash chromatography (silica, gradient elution: 2-5% methanol in CHCl$_3$), to afford activated MPEG-alkyl-acid II.

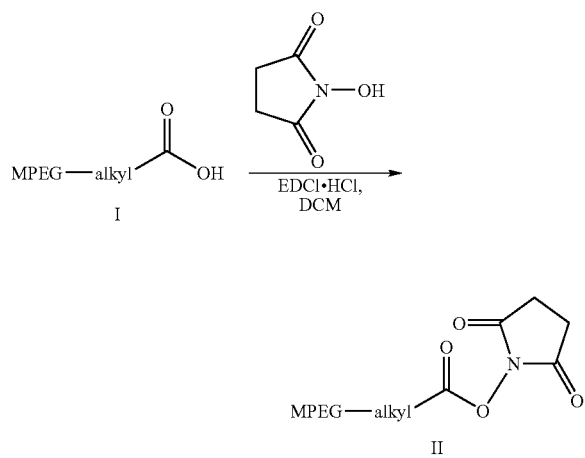

8.14 Synthesis of Modifying Moiety with Branched PEG
(6-[2-(2-{2-[2-(2-Methoxy-ethoxy)-ethoxy]-ethoxy}-ethoxy)-1-(2-{2-[2-(2-methoxy-ethoxy)-ethoxy]-ethoxy}-ethoxymethyl)-ethoxycarbonylamino]-hexanoic acid 2,5-dioxo-pyrrolidin-1-yl ester)

1. Tetraethylene glycol monomethyl ether (14.0 g, 67 mmol) was dissolved in tetrahydrofuran (90 mL) and NaH (1.77 g, 74 mmol) was added portion wise and reaction was stirred for 2 h. Then epichlorohydrin (26.3 mL, 0.34 mol) was added dropwise and the reaction was stirred at RT for 48 h. The crude reaction mixture was filtered through Celite and washed CH$_2$Cl$_2$ (250 mL). The filtrate was washed H$_2$O (2×250 mL), dried MgSO$_4$, and evaporated to dryness. Column chromatography (silica, ethyl acetate) afforded 1 a clear oil (10.15 g, 57% yield).

2. Tetraethylene glycol monomethyl ether (7.96 g, 0.038 mol) and 1 (10.1, 0.038 mol) were dissolved in CH$_2$Cl$_2$ (100 mL) and BF$_3$OEt$_2$ (0.48 mL, 0.0038 mol) was added. The reaction was stirred overnight at RT. Crude reaction was diluted with CH$_2$Cl$_2$ (200 mL), washed sat. NaHCO$_3$ (300 mL), H$_2$O (300 mL), dried MgSO$_4$, and evaporated to dryness. Column chromatography (silica, ethyl acetate/MeOH, 10:1) afforded 2 a clear oil (4.5 g, 25% yield).

3. 4-Nitrochloroformate (2.87 g, 14.3 mmol) and 2 (4.5 g, 9.5 mmol) were dissolved in CH$_2$Cl$_2$ (45 mL). After stirring for 10 min, TEA (2.1 mL, 15 mmol) was added and reaction stirred overnight at RT. Crude reaction was diluted with CH$_2$Cl$_2$ (130 mL), washed 1M HCl (175 mL), H$_2$O (175 mL), dried MgSO$_4$, and evaporated to dryness. Column chromatography (silica, ethyl acetate/MeOH, 15:1) afforded 3 a yellowish oil (2.38 g, 40% yield).

4. 6-Aminocaproic acid (0.126 g, 0.96 mmol) and K$_2$CO$_3$ (0.221 g, 1.6 mmol) were dissolved in H$_2$O (DI, 5 mL). Then 3 (0.5 g, 0.8 mmol) was dissolved in THF (0.7 mL) and added dropwise. The reaction was stirred overnight at RT. Crude reaction was diluted with H$_2$O (20 mL), acidified to pH ~1 with HCl, washed CH$_2$Cl$_2$ (2×25 mL), organic layers dried MgSO$_4$, and evaporated to dryness. Column chromatography (silica, CHCl$_3$/MeOH, 15:1) afforded 4 a clear oil (0.428 g, 85% yield)

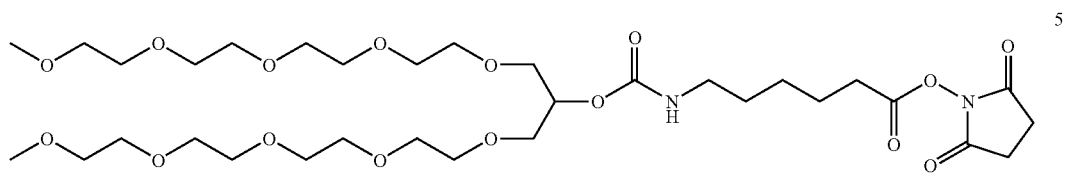

5. Activated using Method II: 4 (0.40 g, 0.64 mmol), N-hydroxysuccinimide (0.088 g, 0.77 mmol), EDCI (0.160 g, 0.83 mmol), and CH$_2$Cl$_2$ (5 mL). Column chromatography (silica, ethyl acetate/MeOH, 10:1) afforded 5 a clear oil (0.320 g, 69% yield).

was added dropwise. The reaction was stirred at 0° C. for 0.5 h and then at RT for 4 hours. The crude reaction was filtered through Celite, washed CH$_2$Cl$_2$ (100 mL), filtrate washed with sat NaHCO$_3$ (150 mL), H$_2$O (150 mL), dried MgSO$_4$, and evaporated to dryness to afford 2 a yellow oil (11.06 g, 85% yield).

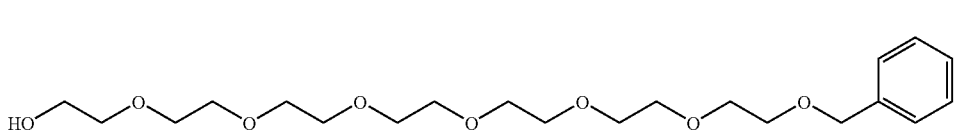

8.15 Synthesis of Linear PEG-Alkyl Modifying Moiety (Carbonic acid 2,5-dioxo-pyrrolidin-1-yl ester 2-{2-[2-(2-{2-[2-(2-hexyloxy-ethoxy)-ethoxy]-ethoxy}-ethoxy)-ethoxy]-ethoxy}-ethyl ester)

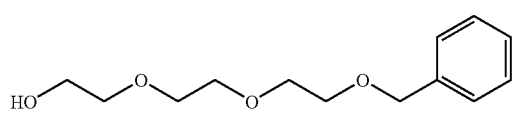

1. Triethylene glycol (30 g, 0.2 mol) was dissolved in a solution of NaOH (8 g in 8 mL of H$_2$O) and stirred for 10 min. Then benzyl chloride (7 mL, 0.062 mol) was added and the reaction mixture was heated to 100° C. and stirred overnight. The crude reaction was diluted with sat NaCl (500 mL), washed CH$_2$Cl$_2$ (2×400 mL), organic layers dried MgSO$_4$, and evaporated to dryness. Column chromatography (silica, ethyl acetate to ethyl acetate/MeOH, 10:1) afforded 1 a yellowish oil (9.87 g, 67% yield).

3. Tetraethylene glycol (7.32 g, 0.038 mol) was dissolved in tetrahydrofuran (140 mL) and NaH was added portion wise over 0.5 h and the reaction was stirred for an additional 1 h. Then 2 (6.0 g, 0.019 mol) was dissolved in CH$_2$Cl$_2$ (20 mL) and added dropwise and the reaction was stirred overnight at RT. Crude reaction was filtered through Celite, washed CH$_2$Cl$_2$, and evaporated to dryness. The resultant oil was dissolved in CH$_2$Cl$_2$ (150 ml), washed H$_2$O (150 mL), sat. NaHCO$_3$ (150 mL), H$_2$O (150 mL), dried MgSO$_4$, and evaporated to dryness. Column chromatography (silica, ethyl acetate/MeOH, 10:1) afforded 3 yellowish oil (3.83 g, 49% yield).

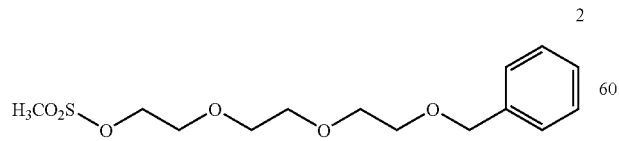

2. To a solution of 1 (9.87 g, 0.041 mol) in CH$_2$Cl$_2$ (50 mL) was added TEA (7.1 mL, 0.054 mol). The solution was then cooled to 0° C. in an ice bath and then methanesulphonyl chloride (3.9 mL, 0.049 mol) dissolved in CH$_2$Cl$_2$ (10 mL)

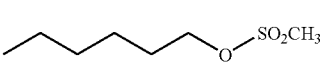

4. Prepared in the same manner as 2: hexanol (6.2 mL, 0.05 mol), methanesulphonyl chloride (4.6 mL, 0.058 mol), TEA (8.6 mL, 0.065 mol), and CH$_2$Cl$_2$ (60 mL) afforded 4 a yellow oil (7.8 g, 86% yield).

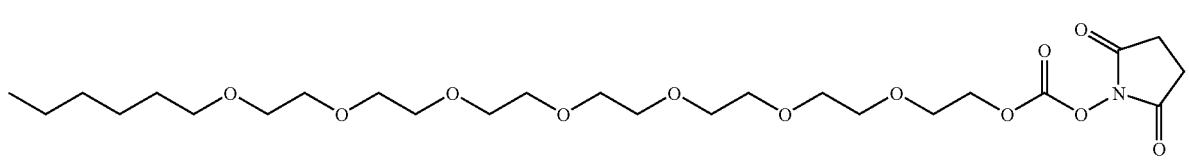

5. To a solution of 3 (5.45 g, 0.13 mol) in tetrahydrofuran (160 mL) was added potassium tert-butoxide (1.60 g, 0.0144 mol) and the reaction was stirred for 1.5 h. Then 4 (2.59 g, 0.0144 mol) dissolved in tetrahydrofuran (20 mL) was added dropwise and the reaction was stirred overnight. The crude reaction was filtered through Celite, washed $CH_2Cl_2$, and evaporated to dryness. The resultant oil was dissolved in ethyl acetate (150 mL), washed $H_2O$ (2×150 mL), dried $MgSO_4$, and evaporated to dryness. Column chromatography (silica, ethyl acetate) afforded 5 a yellowish oil (2.40 g, 36% yield).

8.16 Synthesis Branched Alkyl-PEG-Alkyl (6-[2-(2-{2-[2-(2-Heptyloxy-ethoxy)-ethoxy]-ethoxy}-ethoxy)-1-(2-{2-[2-(2-heptyloxy-ethoxy)-ethoxy]-ethoxy}-ethoxymethyl)-ethoxycarbonylamino]-hexanoic acid 2,5-dioxo-pyrrolidin-1-yl ester)

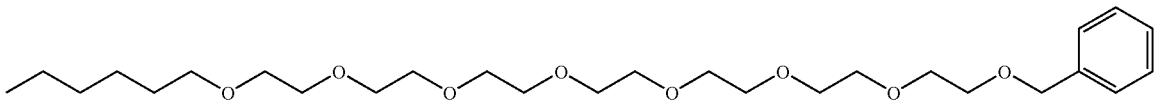

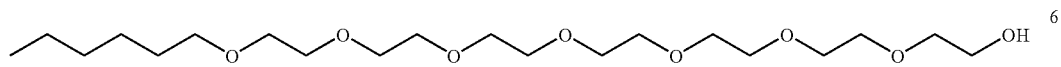

6. To a solution of 5 (2.4 g, 4.8 mmol) in ethyl acetate (160 mL) was added palladium on activated carbon 10 wt % (1.0 g) and the reaction vessel sealed with a septum. A balloon containing $H_2$ was then inserted in the septum via needle and the reaction was stirred overnight at RT. Crude reaction mixture was filtered through Celite, washed ethyl acetate, and evaporated to dryness to afford 6 a clear oil (1.61 g, 82% yield).

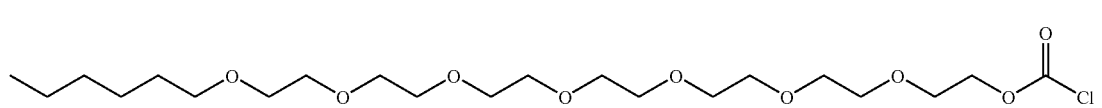

7. A phosgene solution (15 mL of a 20% phosgene in toluene) was cooled to −10° C. and 6 (1.60 g, 3.9 mmol) dissolved in toluene (5 mL) was added dropwise. The reaction was stirred at −10° C. for 0.5 h and then 4 h at RT. The phosgene and toluene was then distilled off and the resultant oil was dried under vacuum to afford 7 a yellowish oil.

1. Prepared in the same manner as shown in Example 8.15: hexanol (18 mL, 0.15 mol), methanesulphonyl chloride (12.3 mL, 0.16 mol), TEA (25 mL, 0.18 mol), and $CH_2Cl_2$ (180 mL) afforded 1 a yellow oil (23.1 g, 85% yield).

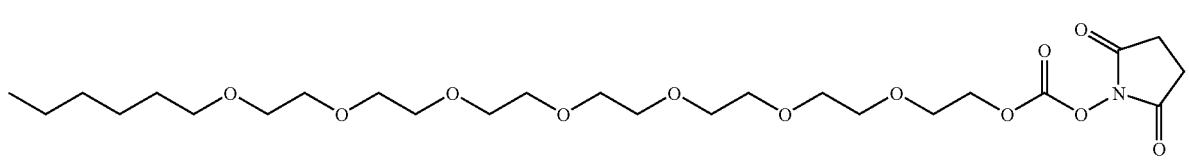

8. Activated using Method II: 7 (1.65 g, 0.79 mmol), N-hydroxysuccinimide (0.437 g, 3.8 mmol), TEA (2.7 mL, 3.8 mmol), and $CH_2Cl_2$ (10 mL). Column chromatography (silica, ethyl acetate/MeOH, 15:1) afforded 8 a clear oil (1.06 g, 57% yield).

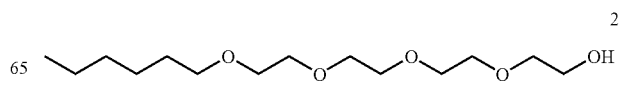

2. Tetraethylene glycol (50.5 g, 0.26 mol) was dissolved in tetrahydrofuran (350 mL) and potassium tert-butoxide (29.2 g, 0.26 mol) was added portion wise over 0.5 h. The reaction was stirred an additional 1 h and then 1 (23.0 g, 0.13 mol) dissolved in THF (50 mL) was added. The reaction was stirred overnight at RT. The crude reaction was filtered through Celite, washed CH$_2$Cl$_2$, and evaporated to dryness. The resultant oil was dissolved in CH$_2$Cl$_2$ (300 mL), washed H$_2$O (2×300 mL), dried MgSO$_4$, and evaporated to dryness. Column chromatography (silica, ethyl acetate) afforded 2 a clear oil (18.51 g, 51% yield).

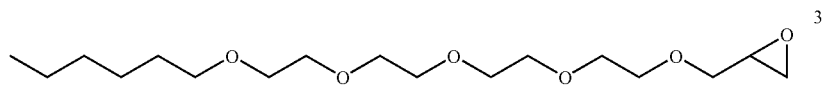

3

3. To a solution of 2 (10.0 g, 36 mmol) in tetrahydrofuran (60 mL) was added NaH (0.95 g, 40 mmol) portion wise and reaction was stirred for 0.5 h. Then epichlorohydrin (14.1 mL, 0.34 mol) was added dropwise and the reaction was stirred at RT for 48 h. The crude reaction mixture was filtered through Celite, washed CH$_2$Cl$_2$, and evaporated to dryness. The resultant oil was dissolved CH$_2$Cl$_2$ (200 mL), washed sat. NaCl (200 mL), sat. NaHCO$_3$ (200 mL), H$_2$O (200 mL), dried MgSO$_4$, and evaporated to dryness. Column chromatography (silica, ethyl acetate/hexanes, 10:1) afforded 3 a clear oil (5.46 g, 45% yield).

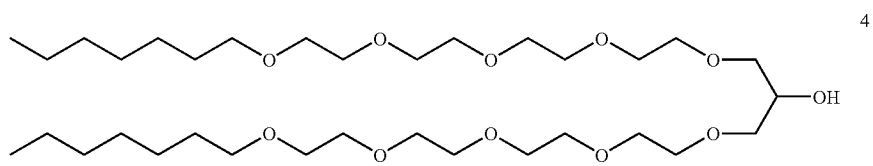

4

4. To a solution of 2 (4.54 g, 16 mmol) and 3 (5.46, 16 mmol) in CH$_2$Cl$_2$ (50 mL) was added BF$_3$.OEt$_2$ (0.48 mL, 0.0038 mol). The reaction was stirred overnight at RT. Crude reaction was diluted with CH$_2$Cl$_2$ (50 mL), washed sat. NaHCO$_3$ (100 mL), H$_2$O (100 mL), dried MgSO$_4$, and evaporated to dryness. Column chromatography (silica, ethyl acetate to ethyl acetate/MeOH, 10:1) afforded 4 a clear oil (2.40 g, 24% yield).

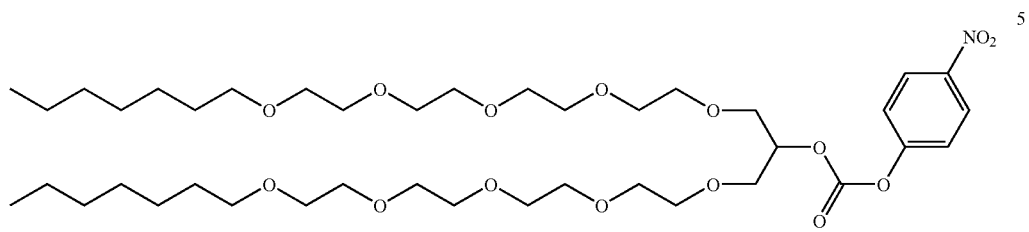

5

5. 4-nitrochloroformate (1.18 g, 5.8 mmol) and 4 (2.4 g, 3.9 mmol) were dissolved in CH$_2$Cl$_2$ (25 mL). After stirring for 10 min, TEA (0.89 mL, 6.4 mmol) was added and reaction stirred overnight at RT. Crude reaction was diluted with CH$_2$Cl$_2$ (75 mL), washed 1M HCl (100 mL), H$_2$O (100 mL), dried MgSO$_4$, and evaporated to dryness. Column chromatography (silica, ethyl acetate) afforded 5 a yellowish oil (1.04 g, 34% yield).

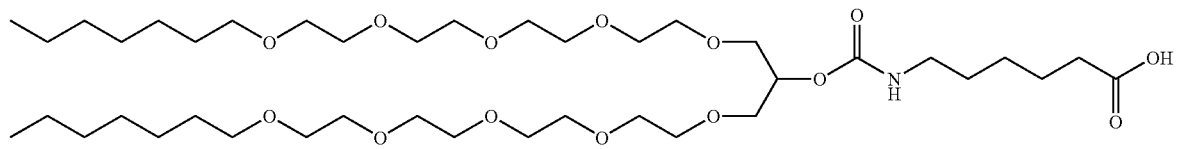

6

6. 6-Aminocaproic acid (0.157 g, 1.2 mmol) and K$_2$CO$_3$ (0.276 g, 2.0 mmol) were dissolved in H$_2$O (DI, 8 mL). Then 5 (0.80 g, 1.0 mmol) was dissolved in THF (1.0 mL) and added dropwise. Oil droplets formed when 3 was added and ethanol (2 mL) was added and the reaction was stirred overnight at RT. Crude reaction was diluted with H$_2$O (30 mL), acidified to pH ~1 with HCl, washed CH$_2$Cl$_2$ (2×35 mL), organic layers dried MgSO$_4$, and evaporated to dryness. Column chromatography (silica, ethyl acetate/MeOH, 20:1) afforded 6 a clear oil (0.720 g, 46% yield)

7

7. Activated using Method II: 6 (0.356 g, 0.46 mmol), N-hydroxysuccinimide (0.063 g, 0.55 mmol), EDCI (0.115 g, 0.6 mmol), and CH$_2$Cl$_2$ (3 mL). Column chromatography (silica, ethyl acetate) afforded 7 a clear oil (0.180 g, 45% yield).

8.17 Hexanoic acid 2-[2-(2-{2-[2-[6-(2,5-dioxo-pyrrolidin-1-yloxycarbonyloxy)-hexylcarbamoyloxy]-3-(2-{2-[2-(2-hexanoyloxy-ethoxy)-ethoxy]-ethoxy}-ethoxy)-propoxy]-ethoxy}-ethoxy)-ethyl ester

1

1. Prepared in the same manner as shown in example 9.15: Tetraethylene glycol (58.27 g, 0.3 mol), NaOH solution (12 g in 12 mL of H$_2$O), benzyl chloride (10.6 mL, 0.092 mol). Column chromatography (silica, ethyl acetate) afforded 1 a yellowish oil (16.8 g, 64% yield).

2

2. Prepared in the same manner as shown in example 9.14: 1 (9.6 g, 34 mmol), NaH (0.898 g, 37 mmol), tetrahydrofuran (50 mL), epichlorohydrin (13.2 mL, 0.17 mol). Column chromatography (silica, ethyl acetate) afforded 2 a clear oil (6.78 g, 58% yield).

3

3. Prepared in the same manner as shown in example 9.14: Tetraethylene glycol (4.85 g, 20 mmol), 2 (6.78 g, 25 mmol), BF$_3$.OEt$_2$ (0.25 mL, 2.0 mmol), CH$_2$Cl$_2$ (75 mL). Column chromatography (silica, CHCl$_3$/MeOH, 20:1) afforded 3 a clear oil (2.85 g, 27% yield).

4

4. To a solution of 3 (2.80 g, 5.2 mmol) in CH$_2$Cl$_2$ (20 mL), was added TEA (0.8 mL, 5.7 mmol) and the solution was cooled to 0° C. Then hexanoyl chloride (0.73 mL, 5.2 mmol) was added dropwise. The reaction was stirred at 0° C. for 0.5 h, then RT overnight. Crude reaction was diluted with CH$_2$Cl$_2$ (80 mL), washed H$_2$O (100 mL), sat. NaHCO$_3$ (100 mL), H₂O (100 mL), dried MgSO₄, and evaporated to dryness. Column chromatography (silica, ethyl acetate/MeOH, 15:1) to afford 4 a yellowish oil (1.95 g, 59% yield).

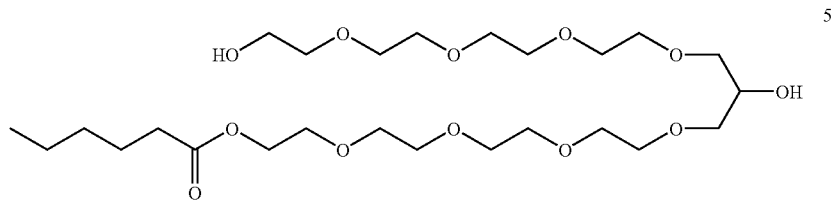

5. To a solution of 4 (1.94 g, 3.1 mmol) in ethyl acetate (20 mL) was added palladium (1.60 g, 5 wt % on activated carbon). The reaction was sealed and stirred under H2 overnight. Crude reaction mixture was filtered through Celite, washed ethyl acetate and evaporated to dryness to afford 6 a clear oil (1.09 g, 65% yield).

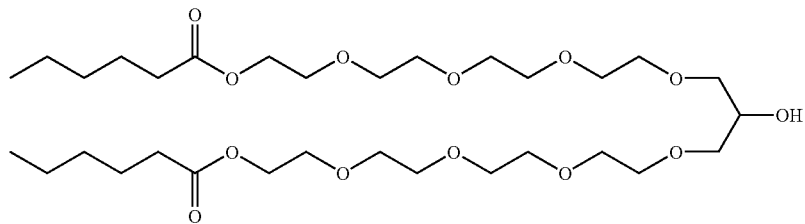

6. To a solution of 5 (1.09 g, 2.0 mmol) in CH₂Cl₂ (14 mL), was added TEA (0.31 mL, 2.2 mmol) and the solution was cooled to 0° C. Then hexanoyl chloride (0.28 mL, 2.0 mmol) was added dropwise. The reaction was stirred at 0° C. for 0.5 h, then RT overnight. Crude reaction was diluted with CH₂Cl₂ (86 mL), washed H₂O (100 mL), sat. NaHCO₃ (100 mL), H₂O (100 mL), dried MgSO₄, and evaporated to dryness. Column chromatography (silica, ethyl acetate/MeOH, 15:1) to afford 6 a yellowish oil (0.698 g, 55% yield).

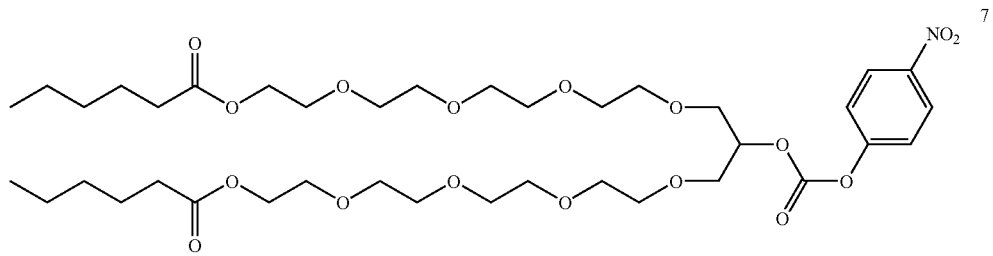

7. Prepared in the same manner as shown in example 9.14: 4-Nitrochloroformate (0.332 g, 1.65 mmol), 6 (0.698 g, 1.1 mmol), TEA (0.28 mL, 2.0 mmol), CH₂Cl₂ (7 mL). Column chromatography (silica, ethyl acetate) afforded 7 a yellowish oil (0.688 g, 78% yield).

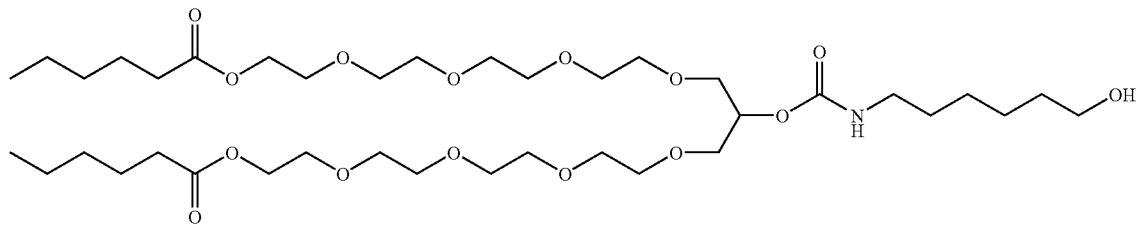

8. Prepared in the same manner as shown in example 9.14: 6-amino-1-hexanol (0.142 g, 1.2 mmol), 7 (0.488 g, 0.6 mmol), TEA (0.12 mL, 0.9 mmol), CH₂Cl₂ (5 mL). Column chromatography (silica, ethyl acetate/MeOH, 15:1) afford 8 a clear oil (0.30 g, 65% yield).

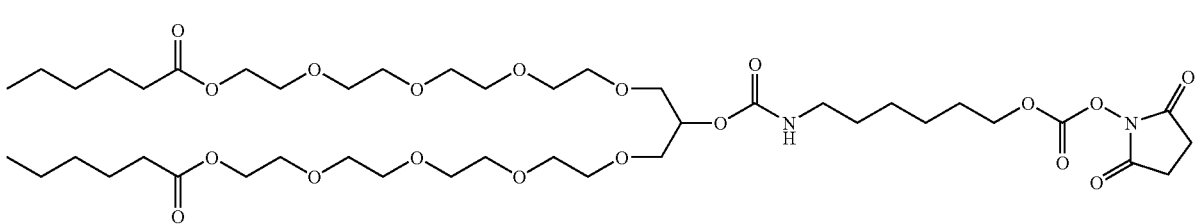

9. Activated using Method I: N,N'-Disuccinimidyl carbonate (0.118 g, 0.46 mmol), 8 (0.30 g, 0.38 mmol), TEA (80 µL, 0.57 mmol), acetonitrile (4 mL). Washings afforded 9 a clear oil (0.344 g, 90% yield).

8.18 6-{2-(2-[2-[2-(2-Hexyloxy-ethoxy)-ethoxy]-ethoxy}-ethoxy)-1-[6-(2-{2-[2-(2-methoxy-ethoxy)-ethoxy]-ethoxy]-ethoxy)-hexyloxymethyl]-ethoxycarbonylamino}-hexanoic acid 2,5-dioxo-pyrrolidin-1-yl ester

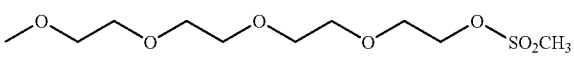

1. Prepared in the same manner as shown in example 9.15: Tetraethylene glycol monomethyl ether (25 g, 0.12 mol), TEA (19.5 mL, 0.14 mol), methanesulphonyl chloride (10.0 mL, 0.13 mol), CH₂Cl₂ (100 mL) afforded 1 a yellow oil (31.35 g, 91% yield).

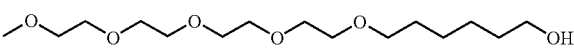

2. 1,6-hexane diol (7.93 g, 0.084 mol) was dissolved in tetrahydrofuran (200 mL). Potassium t-butoxide (10.37 g, 0.092 mol) was added portionwise over 0.5 h and stirred an additional 1 h. Then 1 (12.0 g, 0.042 mol) dissolved in tetrahydrofuran (40 mL) added added dropwise via addition funnel and the reaction was stirred overnight at RT. Crude reaction was filtered through Celite, washed CH₂Cl₂, and evaporated to dryness. The resultant oil was dissolved in CH₂Cl₂ (300 mL), washed H₂O (2×300 mL), dried MgSO₄, evaporated to dryness. Column chromatography (silica, ethyl acetate) afforded 2 a clear oil (5.09 g, 39% yield).

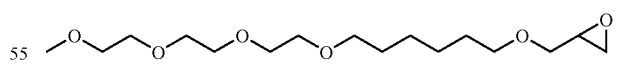

3. To a solution of 2 (5.0 g, 16 mmol) in tetrahydrofuran (35 mL) was added NaH (0.422 g, 17.6 mmol) portion wise and reaction was stirred for 2 h. Then epichlorohydrin (6.3 mL, 8.0 mmol) was added dropwise and the reaction was stirred at RT for 48 h. The crude reaction mixture was filtered through Celite and washed CH₂Cl₂. The resultant oil was dissolved in CH₂Cl₂ (125 mL), washed H₂O (125 mL), sat. NaHCO₃ (125 mL), H₂O (125 mL), dried MgSO₄, and evaporated to dryness Column chromatography (silica, ethyl acetate/MeOH, 20:1) afforded 3 a clear oil (2.00 g, 34% yield).

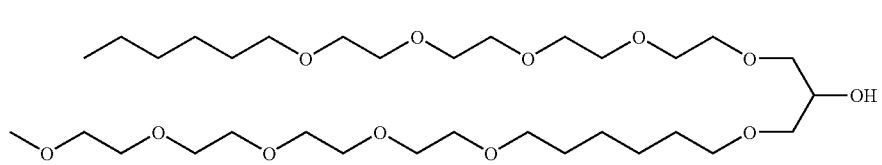

4. Prepared in the same manner as shown in example 9.14: 2 (1.34 g, 4.8 mmol), 3 (1.75 g, 4.8 mmol), BF$_3$.OEt$_2$ (0.06 mL, 0.48 mmol), CH$_2$Cl$_2$ (30 mL). Column chromatography (silica, ethyl acetate/MeOH, 20:1) afforded 4 a clear oil (1.05 g, 34% yield).

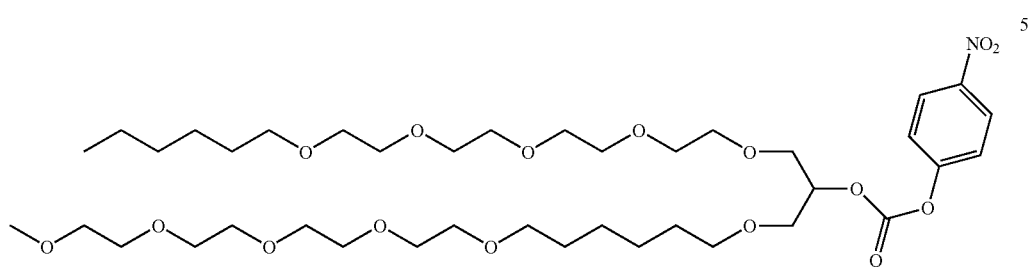

5. Prepared in the same manner as shown in example 9.14: 4-Nitrochloroformate (0.464 g, 2.3 mmol), 4 (1.0 g, 9.5 mmol), TEA (2.1 mL, 1.55 mmol), CH$_2$Cl$_2$ (10 mL). Column chromatography (silica, ethyl acetate to ethyl acetate/MeOH, 20:1) afforded 5 a yellowish oil (0.663 g, 53% yield).

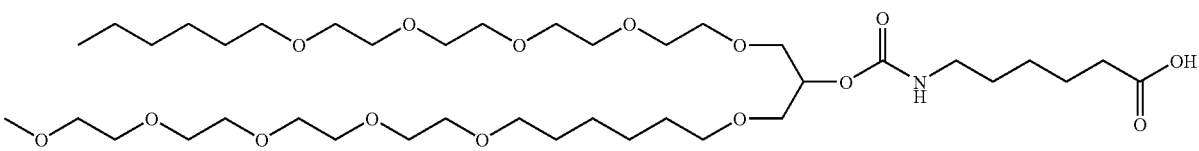

6. Prepared in the same manner as shown in example 9.14: 6-Aminocaproic acid (0.054 g, 0.41 mmol), 5 (0.277 g, 0.34 mmol), K$_2$CO$_3$ (0.094 g, 0.068 mmol), H$_2$O (DI, 5 mL) afforded 6 a clear oil (0.268 g, 96% yield).

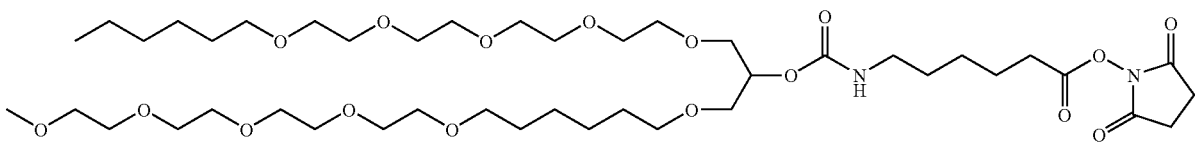

7. Activated using Method II: 6 (0.268 g, 0.34 mmol), N-hydroxysuccinimide (0.047 g, 0.41 mmol), EDCI (0.084 g, 0.44 mmol), and CH$_2$Cl$_2$ (4 mL). Column chromatography (silica, ethyl acetate/MeOH, 15:1) afforded 7 a clear oil (0.178 g, 58% yield).

8.19 Synthesis of Multi-Branched Oligomer

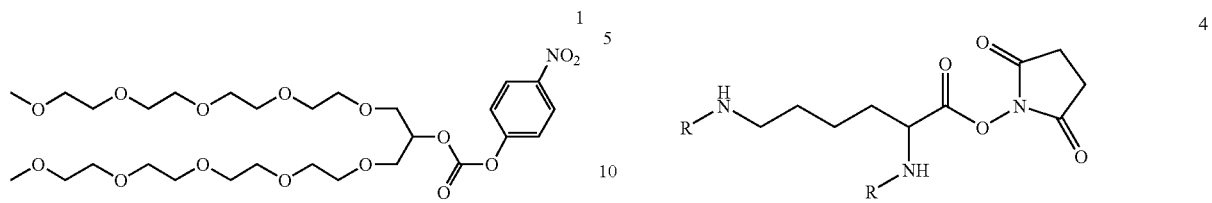

1. As prepared in Example 9.14.

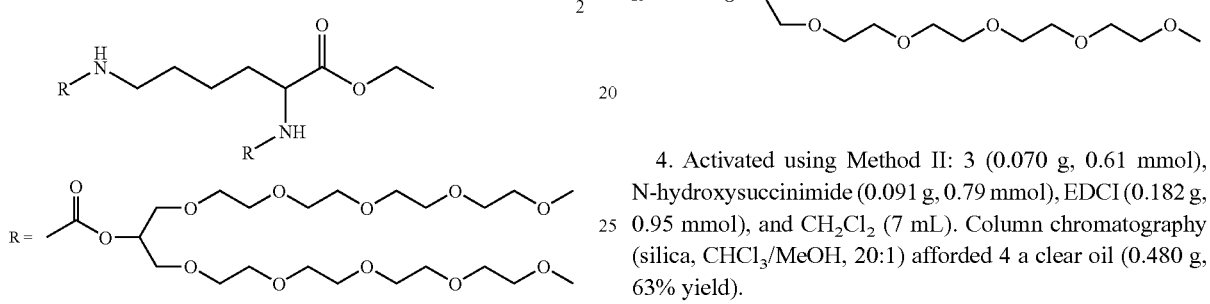

2. L-Lysine ethyl ester dihydrochloride (0.32 g, 1.3 mmol) and 1 (1.71 g, 2.7 mmol) were dissolved in DMF (30 mL) and TEA (0.90 mL, 6.5 mmol) was added. The reaction mixture was stirred overnight at room temperature. Crude reaction was evaporated to dryness, dissolve $CH_2Cl_2$ (30 mL), washed 1M HCl (30 mL), $H_2O$ (30 mL), dried $MgSO_4$, and evaporated to dryness. Column chromatography (Silica, $CHCl_3$/MeOH, 25:1) afforded 2 a clear oil (1.01 g, 66% yield).

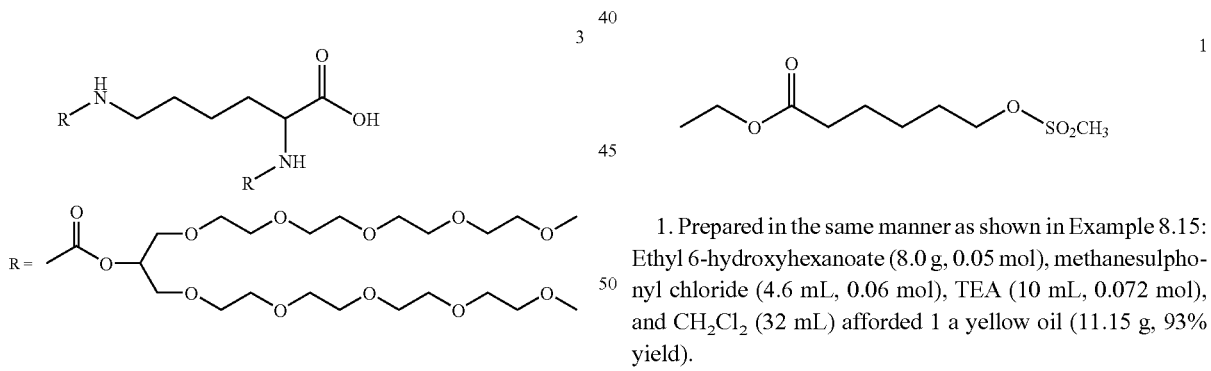

3. A solution of 2 (1.0 g, 0.85 mmol) in 1M NaOH (10 mL) was stirred for 6H at RT. Crude reaction was diluted with sat. NaCl (50 mL), acidified to pH ~2, washed $CH_2Cl_2$ (2×50 mL), dried $MgSO_4$, and evaporated to dryness to afford 3 a clear oil (0.724 g, 74% yield).

4. Activated using Method II: 3 (0.070 g, 0.61 mmol), N-hydroxysuccinimide (0.091 g, 0.79 mmol), EDCI (0.182 g, 0.95 mmol), and $CH_2Cl_2$ (7 mL). Column chromatography (silica, $CHCl_3$/MeOH, 20:1) afforded 4 a clear oil (0.480 g, 63% yield).

8.20 Synthesis of Sugar-PEG-Alkyl Modifying Moiety 2,2-Dimethyl-propionic acid 4,5-bis-(2,2-dimethyl-propionyloxy)-6-(2,2-dimethyl-propionyloxymethyl)-3-{6-[2-(2-{2-[2-(2,5-dioxo-pyrrolidin-1-yloxycarbonyloxy)-ethoxy]-ethoxy}-ethoxy)-ethoxy]-hexanoylamino}-tetrahydro-pyran-2-yl ester)

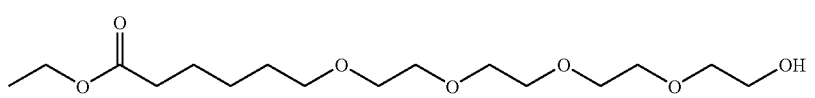

1. Prepared in the same manner as shown in Example 8.15: Ethyl 6-hydroxyhexanoate (8.0 g, 0.05 mol), methanesulphonyl chloride (4.6 mL, 0.06 mol), TEA (10 mL, 0.072 mol), and $CH_2Cl_2$ (32 mL) afforded 1 a yellow oil (11.15 g, 93% yield).

2. Tetraethylene glycol (19.1 g, 0.098 mol) was dissolved in tetrahydrofuran (190 mL) and NaH (1.69 g, 0.071 mol) was added portion wise over 0.5 h. The reaction was stirred an additional 1 h and then 1 (23.0 g, 0.13 mol) dissolved in tetrahydrofuran (10 mL) was added. The reaction was stirred overnight at RT. The crude reaction was filtered through Celite, washed CH₂Cl₂, and evaporated to dryness. The resultant oil was dissolved in CH₂Cl₂ (200 mL), washed sat. NaCl (200 mL), H₂O (200 mL), dried MgSO₄, and evaporated to dryness. Column chromatography (silica, ethyl acetate/MeOH, 25:1) afforded 2 a clear oil (1.60 g, 10% yield).

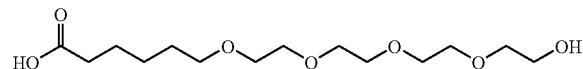

3

3. A solution of 2 (1.60 g, 4.7 mmol) in 1 M NaOH (6 mL) was stirred for 2 h at RT. The crude reaction was diluted with sat. NaCl (24 mL), acidified to pH ~2, washed CH₂Cl₂ (2×30 mL), dried MgSO₄, and evaporated to dryness to afford 3 a clear oil (1.08 g, 73% yield).

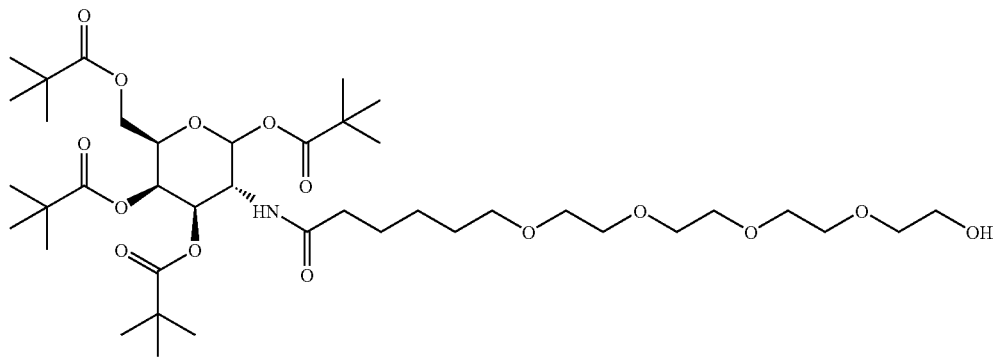

4

4. 2,3,4,6-Tetra-O-pivaloyl-β-D-galactospyranosylamine (0.836 g, 1.6 mmol) and 3 (0.50 g, 1.6 mmol) were dissolved in CH₂Cl₂ (8 mL). Then EDCI (0.368 g, 1.92 mmol) was added and the reaction was stirred overnight at RT. After stirring overnight, reaction was incomplete so EDCI (0.368 g, 1.92 mmol) was added and the reaction was stirred overnight at RT. Crude reaction was diluted with CH₂Cl₂ (22 mL), washed 1 M HCl (30 mL), H₂O (30 mL), sat. NaCl (30 mL), dried MgSO₄, and evaporated to dryness. Column chromatography (silica, ethyl acetate/MeOH) afforded 4 a viscous oil (0.397 g, 31% yield).

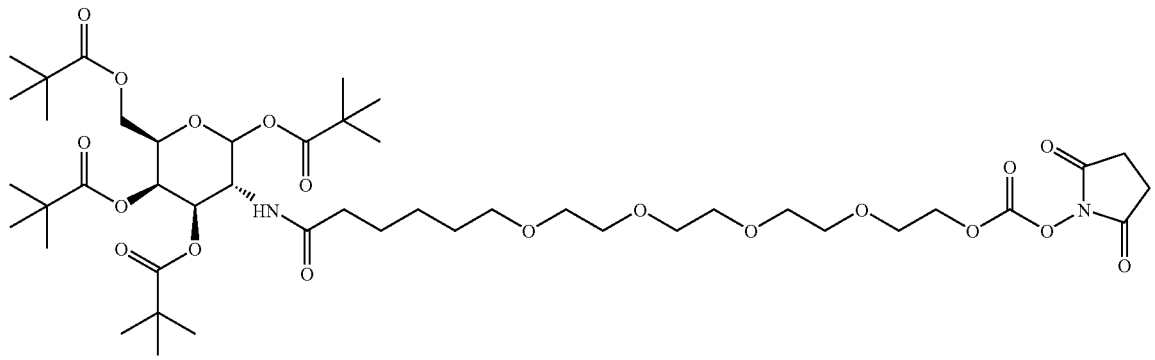

5

5. Activated using Method I: 4 (0.397 g, 0.50 mmol), N-hydroxysuccinimide (0.063 g, 0.60 mmol), TEA (0.10 mL, 0.75 mmol), and acetonitrile (4 mL). Column chromatography (silica, ethyl acetate) afforded 5 a viscous oil (0.256 g, 56% yield).

8.21 Hydrolyzable, Non-hydrolyzable and Pegylated Natriuretic Conjugates

The present example is provided to demonstrate the utility of the present invention for providing natriuretic compound conjugates that have been modified to include virtually all classes of oligomeric moieties, particularly non-hydrolyzed oligomers, microPAGylated oligomers, and hydrolyzable oligomers.

The present hBNP conjugates were synthesized utilizing various oligomers conjugated at different positions on the peptide. The conjugates having the best combination of traits (agonist activity at the receptor, resistance to proteolysis, and oral bioavailability) have become the lead candidates for more extensive in vivo testing.

The native hBNP was obtained from a contract peptide synthesis company. The amphiphilic oligomers that were used in the conjugation came from a supply of oligomers and from oligomers designed and synthesized specifically for conjugation to hBNP. The conjugation followed a three-tiered conjugation strategy as illustrated in FIG. 2. Class 1 oligomers were tested first. Because extensive conjugation with Class 1 oligomers lessened activity, tri and tetra conjugates with Class 2 oligomers were investigated. Because Class 2 oligomers were not as efficacious, two pro-drug conjugates (Class 3 oligomers) were evaluated.

A first class of conjugates is non-hydrolysable. For conjugates of this class, the drug substance that is dosed (i.e., the conjugate) is the substance that acts at the receptor. In other words, the oligomer and its attachment to the peptide remain intact from the time of dosing to the time of clearance. These oligomers may generally be comprised of an alkyl portion and a PEG portion. To maximize the effectiveness of the oligomer to make the conjugate orally available and resistant to proteolysis, the lengths of the alkyl and PEG portions can be altered and the order can be switched. The extent of conjugation (e.g. mono-, diconjugate) can also be manipulated. Some oligomers that can provide conjugates falling within this first class as well as methods for providing such conjugates are described in U.S. Pat. No. 5,359,030 to Ekwuribe; U.S. Pat. No. 5,438,040 to Ekwuribe; U.S. Pat. No. 5,681,811 to Ekwuribe; U.S. Pat. No. 6,191,105 to Ekwuribe; U.S. application Ser. No. 09/474,915, filed Dec. 31, 1999; U.S. application Ser. No. 09/459,443, filed Dec. 13, 1999; and U.S. application Ser. No. 09/873,797, filed Jun. 4, 2001, the disclosures of which are incorporated by reference herein in their entireties.

A second class of conjugates are microPAGylated. For conjugates of this class, the alkyl portion of the oligomer is cleaved once the conjugate is in the bloodstream. These conjugates may be particularly useful when conjugation occurs within a region of the natriuretic pepide that is necessary for binding to receptor, NPR-A. In such cases, the first class of oligomers may be beneficial to stability and delivery, but may be detrimental to activity. The second class of conjugates reduces or eliminates that problem. The amphiphilic oligomer remains intact through the digestive tract and enhances absorption in the upper duodenum. Once in circulation, the alkyl portion is cleaved. Thus, a smaller oligomer is attached to the circulating peptide when it reaches the receptor. In some embodiments, the decreased steric hindrance leads to increased activity at the receptor. Some oligomers that can provide conjugates falling within this second class as well as methods for providing such conjugates are described in U.S. Pat. No. 6,309,633 to Ekwuribe et al. and U.S. application Ser. No. 10/018,879, filed Dec. 19, 2001, the disclosures of which are incorporated by reference herein in their entireties.

A third class of conjugates is fully hydrolysable. For conjugates of this class, the entire oligomer is cleaved once the conjugate is absorbed. Like the second class, these conjugates may be particularly useful when conjugation occurs within a region that is necessary for binding. However, in the event that the microPAGylated conjugates still do not retain sufficient activity, the third class of conjugates may completely obviate the possibility of the oligomer interfering with receptor binding. In this case, the conjugate remains intact through the digestive tract. Once the conjugate is absorbed, the oligomer is cleaved, which releases the native peptide in circulation.

Conjugation of hBNP. The carboxyl group of the amphiphilic oligomer ($C_6PEG_7$) is activated with N-hydroxy succinimide, a common activating group in peptide chemistry. Once activated, the oligomers are attached to the peptide either in aqueous or DMSO solution. hBNP has four sites for conjugation: three Lys residues and the N-terminus. By varying the stoichiometry of the reaction, the extent of conjugation (mono-, di-, etc.) can be controlled. Product distribution can be altered by varying the reaction conditions. As preferred sites for conjugation are discovered through the activity assays, preferential synthesis of the desired conjugates can be obtained by varying the stoichiometry and the reaction conditions.

Choice of PEG-alkyl Oligomers. By varying the relative length of the alkane (hydrophobic) and PEG (hydrophilic) components, the amphiphilicity and solution structure of the conjugate can be improved. The PEG portion is very flexible in solution and may play an important role in resistance to enzymes. The alkyl portion may enhance absorption in the gut and/or enable interaction with cell membranes. The latter feature may be particularly important when the target is a membrane-bound protein on the cell surface, such as NPR-A. Thus, the choice of the oligomer may determine the effectiveness of the conjugate in terms of enzyme stability and oral bioavailability.

Purification of hBNP Conjugates. The reaction mixtures are purified on a preparative HPLC column (C-18) with a solvent gradient system made of isopropanol/water (0.1% trifluoroacetic acid). The solvent is evaporated and lyophilized to give dry products. Purity of the conjugates is determined by reversed-phase HPLC and mass spectrometry.

8.21.1 Class 1 Oligomers: Non-Hydrolyzable

Over thirty conjugates that utilized non-hydrolyzable oligomers (Class 1) were synthesized. For conjugates of this class, the drug substance that is dosed is the substance that acts as the receptor. In other words, the oligomer and its attachment to the peptide remain intact from the time of dosing to the time of clearance. Peptide mapping experiments revealed the sites on hBNP to which the oligomers were attached. By changing the amount of oligomer added to the reaction, product distribution could be skewed. The predominant monoconjugate that formed was conjugated at $Lys^3$; the predominant diconjugate had the oligomers attached at the $Lys^3$ and $Ly^{s4}$. By varying the reaction conditions, the triconjugate and/or tetraconjugate could be formed as the exclusive product. The triconjugate featured oligomer attachment at $Lys^3$, $Lys^{14}$, and $Lys^{27}$. The tetra conjugate added a fourth attachment at the N-terminus. Initially all the available mono, di, tri, and tetra conjugates were isolated for testing activity in vitro. Based on the activity data, the $Lys^3$ monoconjugates when using Class 1 oligomers were focused.

8.21.2 Class 2 Oligomers: Micropegylated

Eight conjugates that utilized micropegylation (Class 2) were synthesized based on the theory that, because Lys14 and Lys27 are in (or proximal to) the binding portion of BNP, micropeg conjugation of these sites would enable the peptide to be more fully conjugated and still retain activity. The amphiphilic oligomer remains intact through the digestive tract and enhances absorption in the upper duodenum. Once in circulation, the alkyl portion is cleaved. Thus, a smaller oligomer is attached to the circulating peptide when it reaches the receptor. Tri- and tetra-conjugates of this class were synthesized both before and after cleavage of the alkyl group. Even after the alkyl groups were cleaved, small PEG units attached to BNP at three or four sites were detrimental to activity (data shown in the next section), though these conjugates retained a therapeutically significant degree of activity.

8.21.3 Class 3 Oligomers: Hydrolyzable Oligomers

Eight conjugates that utilized fully hydrolyzable oligomers (Class 3) were synthesized. For conjugates of this class, the conjugate remains intact through the digestive tract. Once the conjugate is absorbed, the oligomer is cleaved, releasing the native peptide in circulation. Like the second class, these conjugates are useful when conjugation occurs within a region that is necessary for binding. However, in situations where the micropegylated conjugates still do not retain activity, the third class of conjugates completely obviates the possibility of the oligomer interfering with receptor binding. Mono, di, tri, and tetra conjugates were made from this class of oligomers. Tri and tetra conjugates were less stable. Two conjugates were tested.

The reaction mixtures were purified on a preparative HPLC column (C18) with a solvent gradient system made of isopropanol/water (0.1% trifluoroacetic acid). The solvent was evaporated and lyophilized to provide the conjugates was dry powders. Purities of the conjugates were determined by reverse-phase HPLC and mass spectrometry.

Native BNP was examined in the assay to provide a measure of activity for the native, wild-type hBNP peptide. The native hBNP peptide used was the 1-32 amino acid sequence, SPKMVQGSGCFGRKMDRISSSSGLGCKVLRRH, (SEQ ID NO: 99-) in which $C^{10}$ and $C^{26}$ are joined by a disulfide bond to form a bond. The results and structures of twenty-nine of the constructs are provided in Table 1. The BNP conjugates were assessed for EC50 and Emax, and these values were compared to those obtained under the same experimental conditions for the native peptide. These data as compared to native BNP (1-32 aa) without an oligomeric moiety are provided in Table 1. The results point to a preference for the monoconjugate BNP that included a Class 1 modifying moiety Lys3 (BNP-002), and the monoconjugate BNP that include a Class 2 modifying moiety at Lys 14 or Lys 27.

The mono-1, mono-2, mono-3 and mono-4 are the monoconjugates of BNP and labeled as in the order they elute on HPLC. In the following Table, the mono-1 BNP is the BNP peptide conjugate that that includes the indicated modifying moiety (oligomer structure) at the Lys-3 BNP residue. The mono-2 and mono-3 co-elute on HPLC and its a mixture of Lys-14 and Lys-27. The diconjugates are generally obtained as a mixtures that elute closely together on HPLC. The major diconujates are Lys3/Lys14 and Lys3/Lys27. The predominant triconjugate is conjugated at Lys3, Lys14, and Lys27. The product identified as "mono-4" includes the modifying moiety (oligomer) at the N-terminus of the BNP peptide. The "mono-1" includes the modifying moiety conjugated at Lys3 of the BNP peptide. The "mono-2" product includes the modifying moiety (oligomer) conjugated at Lys14 of the BNP peptide, or at Lys 27 of the BNP peptide. For results see the table set forth in FIGS. 6*a-d*.

8.22 Natriuretic Peptide Candidates—Urodilatin, Dendroaspis Natriuretic Peptide (DNP), and Canine Natriuretic Peptide It is anticipated that the present conjugation technology may be used with many different natriuretic peptides and analogs of these peptides to construct any number of different bioactive natriuretic peptide conjugate embodiments with retained pharmacological activity, enhanced cell-membrane permeability, and/or protease resistance. In addition to the hBNP described in several of the examples here, these candidate peptides include by way of a partial list, peptides, peptide fragments and whole peptides, and multi-constructs peptides prepared and/or isolated from the following assembly of bioequivalent peptides/proteins. It is within the scope of the present invention to include these constructs and conservative substituted constructs thereof in the preparation of the embodiments, the present invention, as well as in pharmaceutical preparations containing these constructs in a conjugated from with at least one modifying moiety as defined herein in the treatment of congestive heart failure. These peptides posses a structure amenable to modifying conjugation moiety.

1. Urodilatin (hANP with Four Additional Residues at the N-Terminus)

TAPRSLRRSSCFGGRMDRIGAQSGLGCNSFX$^1$Y (SEQ ID NO. 100)

The amino acid T defines a modifying moiety conjugation site. In the above sequence, $X^1$ is lysine or an amino acid other than arginine. Where $X^1$ is lysine, a second modifying moiety conjugation site is provided.

2. Canine Natriuretic Peptide (Canine NP)

Canine BNP offers natural advantages for manufacturing of conjugates. No conjugation sites exist in the loop region. Conjugation sites are present in the N- and C-terminal tails. These features would enable conjugation without substantial loss of activity. It should also lead to a smaller distribution of products, resulting in higher yield and easier purification.

(SEQ. ID. NO. 101)
SPX$^1$MMHX$^2$GGCFGRRLDRIGSLSGLGCNVLRX$^3$Y

The amino acid sites of $X_1$, $X_2$, and $X_3$ present modifying moiety conjugation sites. In this neutral peptide, all 3 sites of the peptide are available for conjugation with a modifying moiety. The loop region is identified at amino acid 10 (C) to amino acid 26 (C). It is envisioned that any 2 or all 3 of the amino acids at position 3, 14, or 27 may be substituted with a residue other than Lys, such as Arg.

3. Dendroaspis Natriuretic Peptide (DNP)

(SEQ ID NO. 102)
EVX$^1$YDPCFGH X$^2$IDRINHVSN LGCPSLRDPRPNAPSTSA

The amino acid site of the $X_1$ and $X_2$ are modifying moiety conjugation sites. In this example, both $X_1$ and $X^2$ are the amino acid Lys. In some embodiments, $X^1$ is Arg or $X^2$ is Arg. The N terminus is also a conjugation site. Preferably, where $X^1$ is lysine, $X^2$ is arginine (or other than lysine). Optionally, the peptide may include a further conjugation site at the N-terminus.

4. C-Type Natriuretic Peptide (CNP)

```
GLSK¹GCFGLK²LDRIGSMSGLGC        (SEQ ID NO. 103)
```

The amino acid site of the $K^1$ and $K^2$ are modifying moiety conjugation sites. In this example, both $K^1$ and $K^2$ are the amino acid Lys. However, analogs of the peptide may include an Arg (R) in place of Lys at either or both of these positions in the peptide. Optionally, the peptide may include a further conjugation site at the N-terminus.

5. ANP (Human)(Rat)(Porcine)

```
SLRRSSCFGGRXDRIGAQSGLGCNSFRY    (SEQ ID NO. 104)
```

In this example, X is Met(M) or Ile(I), and wherein a modifying moiety conjugation site is at the N-terminus, or R is changed to K to provide a modifying moiety site.

8.23 Agonist Activity at the Human Natriuretic Peptide Receptor A (NPR-A)

The vasorelaxant, natriuretic, and diuretic properties of BNP are ascribed to a secondary messenger, cyclic GMP (cGMP). The production of cGMP is accomplished by guanylate cyclase, an enzyme that is activated when BNP binds to the natriuretic peptide receptor A (NPR-A) on the surface of endothelial cells. The ability of the conjugates with either non-hydrolyzable (Class 1) or micropegylated (Class 2) oligomers to stimulate the production of cGMP in human aortic endothelial cells (HAEC) expressing the natriuretic peptide receptor-A (NPR-A) was evaluated. For the micropeglyated group, the conjugates were tested with and without the alkyl portion attached. The conjugates with fully hydrolyzable oligomers (Class 3) were not evaluated in this assay because the compound that is ultimately released in circulation is the native peptide.

Tri- and tetra-conjugates utilizing non-hydrolyzable (Class 1) oligomers were less active. Therefore, tri- and tetra-conjugates utilizing micropegylated (Class 2) oligomers were prepared and tested. The in vitro data generated from these Class 2 oligomers is presented in Table 2.

TABLE 2

In vitro activity of hBNP conjugates utilizing Class 2 oligomers.

| hBNP or hBNP Conjugate | Extent of Conjugation | Average $EC_{50}$ (nM) | Average $E_{max}$ % |
|---|---|---|---|
| Native hBNP | None | 236 (+/−) 120 | 100 |
| BN-007 | Tri | >10,000 | <20 |
| BN-008 | Tetra | >10,000 | <20 |
| BN-010 | Tetra | >10,000 | <20 |
| BN-013 | Tetra | >10,000 | <20 |
| BN-014 | Tri | >10,000 | 26.5 |
| BN-015 | Tetra | >10,000 | <20 |
| BN-016 | Tetra | >10,000 | 24.6 |
| BN-018 | Tetra | >10,000 | <20 |

FIG. 3 shows the activity curves for various Lys-3 conjugates utilizing Class 1 oligomers. The four conjugates in Table 2 demonstrates an average $E_{max}$ and an average $EC_{50}$ closest to those the activity obtained with native forms of the BNP peptide (Table 3) and were thus evaluated further in other assays.

TABLE 3

In vitro activity of hBNP conjugates.

| Compound | Average $EC_{50}$ (nM) | Average $E_{max}$ (%) | n |
|---|---|---|---|
| Native hBNP | 236 (+/−) 120 | 100 | 25 |
| BN-002 | 387 (+/−) 171 | 102 | 5 |
| BN-021 | 355 (+/−) 140 | 90 | 5 |
| BN-022 | 364 (+/−) 99 | 79 | 5 |
| BN-024 | 296 (+/−) 172 | 87 | 6 |

Primary HAEC were purchased from Clonetics for cGMP screening. Cells were plated into 12 well plates the day before the experiment. On the day of the experiment, cells were pre-incubated for 10 min at 37° C. with 0.5 mM IBMX to inhibit phosphodiesterases. Test compounds were added to the cells for an additional 60 min at 37° C. and the incubation was stopped by lysing cells to measure cGMP. An ELISA-based cGMP kit was used to measure cGMP production (CatchPoint-cyclic GMP Fluorescent Assay Kit, catalog #R8074, Molecular Devices Corp, Sunnyvale, Calif.). This kit measures cGMP via a competitive immunoassay in 96-well format. Cell lysates were added to the coated microplate followed by the addition of an anti-cGMP antibody and a horseradish peroxidase (HRP)-cGMP conjugate. Plates were incubated for two hours at room temperature, followed by four washes. A substrate solution was added and the fluorescent intensity of each well was quantitated. The fluorescent signal intensity decreased with increasing levels of cGMP. Native hBNP was be tested in each experiment as a positive control.

8.24 BNP Conjugates and Increased Resistance to Proteases

The natriuretic compound that were active in vitro are being tested for their stability in the presence of various proteases, such as trypsin and chymotrypsin. The stability of these compounds conjugated to proteases can be determined by the half-lives of the compound conjugates in the presence of trypsin and chymotrypsin. Thus, several conjugates evaluated in these assays had a longer half-life than did native hBNP. For example, see FIG. 4.

Conjugates were incubated with the enzyme for 2 to 120 minutes at 37° C. Digestions were stopped by adding a 1:1 1% trifluoroacetic acid (TFA): isopropanol quenching solution. Digestion of the hBNP conjugates were compared to the digestion of native hBNP in each experiment. The amount of parent compound remaining in each sample was quantitated by HPLC analysis.

8.25 BNP Conjugates and Oral Bioavailability

The conjugates that were active in vitro were tested for their oral bioavailabily in rats. The conjugates were administered to the gastrointestinal tract by oral gavage and the presence of hBNP conjugates in the bloodstream was assayed using available radioimmunoassay procedures. The antibodies for detection of hBNP are specific; cross reactivity with rat BNP is less than 1%. Consequently, cross reactivity and interference by endogenous rat BNP was not an issue.

Adult, male rats weighing approximately 250 g were used for determining oral bioavailability of hBNP and hBNP conjugates. Rats were fasted overnight and tap water was provided ad libitum (except for a period of no water for 2 hours pre-dosing until 1 hour post dosing).

Prior to dosing, rats were weighed and distributed throughout the dosing groups by body weight so that each dosing group weighed approximately the same. Five rats were used per time point. Conjugates were administered in a liquid fatty acid formulation at a dose of 2.5 mg/kg. Blood samples were taken at 5, 15, 30, and 60 min after dosing. Central venous blood for all dosing experiments was collected and centrifuged. Plasma samples were frozen at −80° C. for analysis.

The plasma concentrations of hBNP conjugates were measured by a commercial immunoradiometric assay (IRMA) specific for the quantitative determination of human BNP in plasma (SHIONORIA™ BNP, Catalog # 127024, Shionogi & Co., Ltd, Osaka, Japan). Blood was drawn from the dosed rats into EDTA coated plastic polyethylene telepthalate (PET) blood collection tubes and centrifuged at 1600-2000×g for 5 minutes in a refrigerated (2-8° C.) centrifuge. Samples were stored in plastic tubes at −80° C. in non-frost free freezers until analysis. 500 μL of sample were used for the IRMA. 100 μL of the sample was added to a tube with 200 μL of $^{125}$I-BNP reagent and one anti-BNP antibody coated bead. Each tube was vortexed and incubated without shaking, for 18 to 22 hours at 2 to 8° C. The tubes were then aspirated and washed with 2.0 mL of washing solution (buffer solution+ 0.05% NaN$_3$) and then reaspirated. The wash process was repeated and the contents of the tube aspirated. The remaining radioactivity in each tube was counted by a gamma counter. The radioactivity was directly proportional to the concentration of hBNP or HBNP conjugates in the sample. In order to accurately quantify samples of hBNP conjugates and allow for differences of antibody recognition between hBNP conjugates and the native molecule, concentration was determined from a standard curve obtained for the appropriate hBNP conjugate.

The four conjugates that were dosed in rats were all detectable in circulation five minutes after dosing (FIG. 5). These four conjugates were BNP-002, BN-021, BN-022, and BN-024.

8.26 Preparation of a Diconjugate, a Monoconjugate and a Triconjugate Polymer Modifications on the Peptide Structure The present example is provided to demonstrate the utility for the present invention in the creation of multi-conjugate forms of the bioactive peptide of choice. By way of example, the present description will describe a monoconjugate, a diconjugate and a triconjugate form of the human natriuretic peptide, hBNP.

Protocol for Conjugating to hBNP:

The oligomers would be attached via the same procedure used for conjugation to hBNP. One difference will be more of the activated oligomer may be added (1-10 equivalents; preferably 3-5 equivalents).

Lysines are in the tails of the sequence. Multiple conjugation sites would presumably afford greater stability in the presence of proteases. The lack of conjugation sites within the loop is advantageous for binding at the NPR-A binding motif.

8.27 Synthesis of an hBNP Amphiphilic Polymer Conjugate

By using amphiphilic oligomers of different size and chemical composition, the absorption and partitioning properties of a peptide conjugate, such as hBNP conjugate, can be altered. Conjugate screening is used to determine which of the conjugates retain the activity of the native peptide and show enhanced resistance to enzymes. The conjugates that have a desirable combination of traits (e.g., agonist activity at the receptor, resistance to proteolysis, and oral bioavailability) may become lead candidates for more extensive in vivo testing.

8.27.1 General Procedure for Conjugation to BNP

Monoconjugate hBNP use sites Lys 3 or Lys 14, or Lys 27, or at the N-terminus of the peptide.

Method I: Preparation of Monoconjugates h-BNP (1 equiv) was dissolved in DMSO (1 ml/35 mg of h-BNP). The activated oligomer (1.1 equiv) was dissolved in a minimal amount of THF and added to the solution of h-BNP in DMSO. The reaction was monitored by HPLC. Samples for HPLC monitoring were prepared by taking 50 μL of the reaction and diluting it in 500 μL of H$_2$O containing 0.1% TFA. Reactions were carried out for 45 min. If reactions were not immediately purified they were frozen until purification could be performed.

Method II: Preparation of Multiple Conjugates h-BNP (1 equiv) was dissolved in DMSO (1 ml/35 mg of h-BNP). Once h-BNP was dissolved, TEA (120 equiv) was added and the solution stirred for 5 min. Then the activated oligomer (2.2 equiv for diconjugate, 4 equiv for triconjugate, 5 equiv for tetraconjugate) was dissolved in a minimal amount of THF and added to the solution of h-BNP in DMSO. The reaction was monitored by HPLC. Samples for HPLC monitoring were prepared by taking 50 μL of the reaction and diluting it in 500 μL of H$_2$O containing 0.1% TFA. Reactions were carried out for 45 min. If reactions were not immediately purified they were frozen until purification could be performed.

Diconjugate HBNP use sites Lys 3, and Lys 14, or Lys 3 and Lys 27 site on hBNP.

Triconjugate hBNP use sites Lys 3, Lys 14 and Lys 27.

8.28 Natriuretic Compound Analogs

The present example is provided to demonstrate the utility of the present invention for providing a variety of forms of bioactive BNP-like peptide and peptide fragments thereof for use in the practice of the present invention. These variant forms, or analogs, are characterized by the presence of one or more mutated amino acids in place of a naturally occurring amino acid from the corresponding native peptide/protein.

1. Analog of hBNP-loop region alone

CFGRXMDRISSSSGLGC-            (SEQ ID NO. 105)

wherein X is an amino acid other than Lys, or X is Arg or Gly.

2. Analog of hBNP-3Arg or an amino acid other than Lys

-SPRMVQGSG-CFGRKMDRISSSSGLGC(SEQ ID NO. 106)-X$^2$- wherein $X^2$ is 1 to 10 amino acids, preferably 1-6 amino acids in length. In some embodiments, $X^2$ is KVLRRH (SEQ ID NO. 32), KVLRR (SEQ ID NO.31), KVLR (SEQ ID NO. 30), KVL, KV, K, RVLRRH (SEQ ID NO. 13), RVLRR (SEQ ID NO. 16), RVLR (SEQ ID NO. 17), RVL, RV, or R.

3. Analog of hBNP-3 mutation sites; 3Arg, 14Arg, 27Arg (SEQ ID NO. 107)
SPX$^1$MVQGSG-CFGRX$^2$MDRISSSSGLGC-X$^3$VLRRH wherein $X^1$ is Lys or an amino acid other than Lys, $X^2$ is an amino acid other than Lys, and $X^3$ is Lys or an amino acid other than Lys. In some embodiments, $X^1$, $X^2$, and $X^3$, are independently Arg or Gly. In other embodiments, $X^1$ is Lys, $X^2$ and $X^3$ are independently Arg or Gly. In a preferred embodiment, at lease one of $X^1$, $X^2$, and $X^3$ is Lys.

4. Analog of hBNP-14 and 27Arg, and a terminal modification site, $X^1$.

```
X¹SPKMVQGSG-CFGRX²MDRISSSSGLGC-X³VLRRH-    (SEQ ID NO. 108)
```

Wherein $X^1$ is a C-terminus modification site (Ser); and wherein $X^2$ and $X^3$ are an amino acid other than Lys. In some embodiments $X^2$ and $X^3$ are independently Arg or Gly. In other embodiments, $X^2$ is Arg and $X^3$ is Lys.

5. Analog of hBNP-14Arg (All fragments in which one or both tails are shortened up to the loop)

```
X¹---CFGRRMDRISSSSGLGC(SEQ ID NO. 109)- X²
``` wherein $X^1$ is 1 to 10 amino acids, preferably 1-9 amino acids in length, and wherein $X^2$ is 1 to 10, preferably 1-6 amino acids in length. $X^1$ may comprise SPKMVQGSGC (SEQ ID NO. 110), PKMVQGSGC (SEQ ID NO. 111), KMVQGSGC (SEQ ID NO. 112), MVQGSGC (SEQ ID NO. 113), VQGSGC (SEQ ID NO. 114), QGSGC (SEQ ID NO. 115), GSGC (SEQ ID NO. 116), SGC, GC, C, SPK, SPKM (SEQ ID NO. 10), SPKMV (SEQ ID NO. 9), SPK-MVQ (SEQ ID NO. 8), SPKMVQ (SEQ ID NO. 8), KMVQ (SEQ ID NO. 117), KMV, KMVQG (SEQ ID NO. 118), KMVQGS (SEQ ID NO. 119), KMVQGSG (SEQ ID NO. 12), or KMVQGSGC (SEQ ID NO. 120). $X^2$ may comprise KVLRRH (SEQ ID NO. 32), KVLRR (SEQ ID NO. 31), KVLR (SEQ ID NO. 30), KVL, KV, K, RVLRRH (SEQ ID NO. 13), RVLRR (SEQ ID NO. 14), RVLR (SEQ ID NO. 15), RVL, RV, or R.

6. Analog of hBNP 1-29-3Arg or amino acids other than Lys

```
SP X¹MVQGSG-CFGRKMDRISSSSGLGC- KVL    (SEQ ID NO. 121)
``` wherein $X^1$ is Arg, or amino acid other than Lys

7. Analog of hBNP 1-26-3Arg or amino acid other than Lys

```
SPX¹MVQGSG-CFGRKMDRISSSSGLGC    (SEQ ID NO. 122)
``` wherein $X^1$ is Arg, Gly, or another amino acid other than Lys.

8. Analog of hBNP-shortened C-terminal tail Lys 14 Arg, 27Arg, or amino acid other than Lys

```
X¹ - CFGRRMDRISSSSGLGC-RVLRRH    (SEQ ID NO. 123)
``` wherein $X^1$ is 1 to 10 amino acids, preferably 1 to 9 amino acids in length. $X^1$ may comprise SPKMVQGSGC (SEQ ID NO. 110), PKMVQGSGC (SEQ ID NO. 111), KMVQGSGC (SEQ ID NO. 112), MVQGSGC (SEQ ID NO. 113), VQGSGC (SEQ ID NO. 114), QGSGC (SEQ ID NO. 115), GSGC (SEQ ID NO. 116), SGC, GC, or C.

9. Analog hBNP-Lys 14Arg or an amino acid other than Lys

```
-CFGR X¹MDRIX²GLGC-    (SEQ. ID. NO. 124)
``` wherein $X^1$ is Arg or an amino acid other than Lys, and $X^2$ is one to four amino acids. In some embodiments, $X^2$ is SSSS (SEQ. ID. NO. 3), SSS, SS, S, KSSS (SEQ. ID. NO. 4), KSS, or KS.

10. Analog hBNP-Arg 30 Lys or other equivalent amino acid of like charge

```
SPKMVQGSGCFGRKMDRISSSSGLGCKVRX₁RH    (SEQ ID NO. 125)
``` wherein $X^1$ is Lys or an amino acid other than Arg.

11. Analog of hBNP-27Arg or an amino acid other than Lys

```
SPKMVQGSGCFGRKMDRISSSSGLGC X¹VLRRH    (SEQ ID NO. 126)
``` wherein $X^1$ is Arg or an amino acid other than Lys.

12. Extension Forms of hBNP

```
                                          (SEQ ID NO. 127)
-SPKMVQGSG-CFGRKMDRISSSSGLGC- KVLRRH - X²
```

$X^2$ is Lys, Cys, or Lys+Xaa$_n$, where n is 1-100, 1-50 or 1-10, and Xaa is any amino acid, or group of amino acids independently selected, or an unknown amino acid 13. Deletion mutant analog -hBNP

```
-CFGR X¹MDRIX²GLGC -    (SEQ ID NO. 128)
``` wherein $X^1$ is Arg or an amino acid other than Lys and wherein $X^2$ is 1 to 4 amino acids, such as SSSS (SEQ ID NO. 3), SSS, SS, S, KSSS (SEQ ID NO. 4), KSS, or KS.

14. hBNP Analog Receptor Specificity

```
SPZ¹MVQGSG-CFGRZ²MDRISSSSX¹X²X³C    (SEQ ID NO. 129)
```

Wherein $Z^1$ is arginine or an amino acid other than lysine, and wherein $Z^2$ is arginine or an amino acid other than lysine, wherein $X^1$ is Gly, Met, Leu, Phe, Ile or a conservative substitutions thereof, wherein $X^2$ is Leu, Trp, Tyr, and Phe or a conservative substitutions thereof, and wherein $X^3$ is Gly, Arg, or a conservative substitution thereof. In another embodiment of this analog, $Z^1$ is lysine and $Z^2$ is arginine or an amino acid other than lysine.

15. ANP analogs

```
K CFKGKNDRX¹ KX² QSGLX³C-NSFKY    (SEQ ID NO. 130)
```

Wherein $X^2$ is T, A, R, H, P, E;
Wherein $X^2$ is K, N-methyl, Arg, S, D, or P;
Wherein $X^3$ is Arg, K, Y, F, S, P, Orn, Har, Har, p-amidinophenyl Ala, I, any other amino acid that has a positive charge other than Gly, or Try 9.26 Recombinant Production of Native BNP and BNP-Pro-Peptide and Pro-Peptide Approach to Manufacturing of BNP Conjugate An oral route of administration will require a large volume supply of BNP peptide. Due to the high cost and supply volume limitations associated with synthetic means to supply BNP, a recombinant technology will be preferred for preparing the conjugated BNP peptide. A recombinant technology for the supply of peptide for the production of the conjugate is described here.

9.26.1 Selection Of Recombinant Technology

The goal is to select a high expression recombinant technology that is known to express small proteins (>10,000K) free of glycosylation and have the peptides secreted in soluble form for easy isolation.

An *E-coli* based expression system (U.S. Pat. No. 5,114,923, Seilhamer et. al. is incorporated herein by reference), is used for production of bulk BNP for the approved drug Natrecor®. Use of the *E-coli* bacterial system is well known and well utilized in the industry for the past many decades for recombinant production of single chain proteins. The *E-coli* system is in general a simpler system for laboratory uses. Many new *E-coli* systems have been developed with high cell density to provide high yield of protein expression. However, in general, there exists a limitation to the use of an *E-coli* based system because of its tendency to secrete the protein in its insoluble form into an inclusion body and to be improperly folded (improper disulfide bond between cysteine amino acid residues). These limitations often leads to high cost of goods, expensive down stream processing steps must be implemented to isolate the protein from inclusion body, and refolding the improperly folded protein to its natural state.

9.27 Construct of Pro-Protein (Pro-BNP) Sequences

The natriuretic compound may also be a multipeptide having two or more natriuretic compound units in sequence and optionally including a spacer sequence between the natriuretic compound unit, and the construct may also optionally comprise a leader and/or extendor sequence at either or both ends of the natriuretic peptide compound. For example, without limiting the multipeptide, to any particular construct, the multipeptide may have the following structures:

NP-[NP]$_n$;
NP-[Spacer-NP]$_n$;
Leader-NP-[NP]$_n$;
Leader-NP-[Spacer-NP]$_n$;
Leader-[Spacer-NP]$_n$;
Leader-[Spacer-NP]$_n$-Extension;
Leader-NP-[Spacer-NP]$_n$-Extension;

where n may, for example be 1, 2, 3, 4, 5, 6, 7, 8, 9, 10; NP is a natriuretic peptide or natriuretic peptide analog:

8.29 Pro-BNP

The invention also provides a pro-X-polypeptide, where X is a natriuretic peptide. The Pro-X-peptide for BNP can be designed to carry a leader peptide as the Pro moiety and which can be linked to BNP sequence via an enzymatic cleavage site. A gene sequence can be designed that encodes the expression of peptide as pro-BNP peptide in the selected recombinant technology. The pro-moiety can also be selected to aid more efficient purification from the fermentation scheme. Pro-BNP peptide can be conjugated post-expression with the oligomer and then the pro moiety can be cleaved by a selected enzyme, mobilized or immobilized, to provide the BNP conjugate which can be more easily purified via conventional chromatographic methods in high yield. Specific enzyme cleavage sites will be included between pro moiety and BNP sequence so that the pro moiety can be enzymatically cleaved to yield the BNP sequence.

8.29.1 Pro-BNP Model Synthesis

The pro-BNP construct will be assessed with a synthetic pro-BNP model having a BNP sequence and additional specific amino acids. This synthetic model will be conjugated with oligomer and subjected to cleavage by a specific enzyme to monitor the production of BNP-Oligomer conjugate.

8.29.2 Designs of Pro-BNP

The leader sequence (promoiety) can include a small peptide with a specific enzyme cleavage sequence based on the synthetic model. Other functional amino acid sequences can also be inserted in the leader/spacer sequence to allow easy purification of the pro-BNP protein. The leader sequence can also serve as the pro-moiety to protect the N-terminus from undesired modification during conjugation and can be cleaved upon specific enzyme treatment. Other features can also be built into the leader peptide sequences to allow ease of isolation as pro-BNP or as pro-BNP oligomer conjugate. The leader peptide can also be attached to the C-terminus of the BNP sequence. The leader peptide can also be designed to allow attachment of known fusion proteins.

8.29.3 Pro-BNP Expression

Functionally specific leader sequences can be provided at the N-terminus or/and C-terminus of BNP for insertion into the expression gene sequence or expression cassette of the selected recombinant technology. The expression sequence of a known fusion protein (see Gaken et al, 2000, the entire disclosure of which is incorporated herein by reference for its teaching concerning fusion proteins) can also be inserted into the expression gene in one of the constructs. Using established procedures, the successful transformation expressed genes in the cells can be monitored. The positive transgenic isolates or cells can be isolated and grown for evaluation for the expression of the designed proteins. Expressed proteins can be purified and sequenced. The purified pro-BNP constructs can then be evaluated. Selected cell lines can be characterized and selected for selection future use.

8.29.4 Construction of Pro-Pentapeptide BNP-1 with Trypsin and Carboxy Peptidase-B Cleavage Spacers and His Tagged Leader Peptide The coding sequence for the full length of pro-pentapeptide BNP-1 can be provided according to the following formula: Leader-NP-[Spacer-NP]$_n$ where:

```
Spacer is
-Arg-Arg-Asp-Ala-Glu-Asp-Pro-Arg,   (SEQ ID NO. 79)

Leader is
Glu-Gly-Asp-Arg-Arg,                (SEQ ID NO. 80)

Extension is
(His)6-Glu-Gly-Asp-Arg-Arg;         (SEQ ID NO. 81)

NP is hBNP.
```

In this embodiment, the NP or NP conjugate can be released using a Trypsin and Carboxypeptidse B enzyme cocktail.

(a) Plasmid Construction

Using the standard molecular biology techniques, a plasmid is constructed for expressing the amino acid sequence of pro-pentapeptide BNP-1 [(His)$_6$-Glu-Gly-Asp-Arg-Arg.)-BNP-Arg-Arg-Asp-Ala-Glu-Asp-BNP-Arg-Arg-Asp-Ala-Glu-Asp-BNP-Arg-Arg-Asp-Ala-Glu-Asp-BNP-Arg-Arg-Asp-Ala-Glu-Asp-BNP] (SEQ ID NO. 131). The plasmid is Codon optimized for the host cell (e.g., *E. coli*) used.

DNA fragment coding this multipeptide sequence is assembled synthetically, starting from post leader sequence and the cleavage sites are added in the order of 3' of the His tag/5' of BNP sequence. cDNA of the sequence is purified from ployacrylamide gel using standard techniques. The plasmid structure is confirmed by restriction enzyme analysis.

(b) Expression and Cell Recovery

The *E-coli* cells expressing pro-pentapeptide BNP-1 are cultured with nutrients sufficient to produce the pro-multipeptide. The (His)$_6$ tag pro-penta BNP is recovered from the cells by cell disruption followed by centrifugation, tangential filtration/untrafiltration, homogenization and solubilization of inclusion bodies.

(c) Isolation of the Pro-Pentapeptide BNP-1 from the Soulubilized Inclusion Via affinity Chromatography A HiTrp chelating ($Ni^{2+}$) HP column (Amersham Bioscience) is prepared and the columns are washed with 10 column volumes of distilled water to remove the storage solution, is charged with metal ion solution ($NiSO_4$, 0.1 M) and washed with distilled water to remove unbound. The filtered solution after inclusion body solubilization, is loaded to this column and the column is washed with 10 column volume of biding buffer (20 mM phosphate buffer, pH 7.4, containing 0.5M sodium chloride and 20 mM imidazole), Using a linear gradient 10 column volumes of elution buffer (20 mM sodium phosphate, pH 7.4, containing 0.5M Sodium chloride and 0.5M imidazole) the column is eluted and followed by another 2 column volume of elution buffer at 100%. This procedure purifies the $(His)_6$ tag pentapeptide from other components from the cell recovery sample via chelation to $Ni^{2+}$ affinity of the column. The purity of the pentapeptide is analyzed by RP-HPLC method to be >30%.

(d) Purification and Analysis

The pentapeptide is then further purified via C-18 preparative —HPLC to a purity>75%. The purified pentapeptide is analyzed by ES/MS analysis and provided M+1 ion peaks for the expected MW of pro-pentapeptide BNP-1. Micro sequencing of the material is used to confirm the amino acid sequence of the multipeptide.

8.29.5 Production of Multiple Units of Lys-3 BNP Conjugate from Pro-Pentapeptide BNP-1

(a) Conjugation of Pentapeptide

Pro-pentapeptide BNP-1 ($3.20\times10^{-4}$ mmol) is dissolved in 5 mL of DMSO. To the solution is added 45 uL of triethylamine. The solution is allowed to stir for 5 minutes before a solution of activated PEG7-hexyl oligomer ($19.6\times10^{-4}$ mmol) in ethanol is added. After the reaction has progressed such that HPLC analysis indicates that the pro-multipeptide has been consumed (or the concentration of pro-multipeptide is no longer decreasing), the reaction is quenched by addition of 0.5 mL of 50% aqueous acetic acid solution. The reaction mixture is then processed and exchanged into 100 mM Tris-HCl Buffer, pH 7.6. The major composition of this mixture is expected to be conjugated multipeptide at Lys3 of each BNP unit.

(b) Enzyme Cocktail Cleavage of Oligomer-Conjugated Pro-Pentapeptide BNP-1 to Conjugated BNP Units An aliquot of the Tris-HCl solution of the product mixture from Example 2(a) is analyzed by HPLC to determine the polypeptide concentration therein. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6.

The crude mixture (1 mol eq.) is then allowed to react with trypsin ($1.39\times10^{-3}$ mol eq) and carboxypeptidase B ($4.56\times10^{-4}$ mol eq.). After 30 minutes, the reaction is quenched by addition of 1% trifluoroacetic acid in acetonitrile. The product mixture of the reaction is processed and analyzed by HPLC. Retention time (versus that of reference standards) and mass spectral analysis are used to determine identity. The expected products of the reaction are Lys3 hexyl-PEG7-conjugated BNP, Lys14 hexyl-PEG7-oligomer-conjugated BNP, Lys 27 hexyl-PEG7-oligomer-conjugated BNP, Di hexyl-PEG7-oligomer conjugated BNP, Des Arg-His BNP and Des Arg-His hexyl-PEG7-oligomer conjugated (Lys3 or Lys14 or Lys27) BNP. The major composition of this mixture is Lys3-hexyl-PEG7-conjugated BNP.

8.29.6 Purification of Pro-Pentapeptide BNP-1 Conjugates from Crude Conjugation Mixture Each major product obtained from the conjugation reaction described in Example 2(b) is isolated using reversed-phase HPLC. A column (1.0 cm. i.d.×25 cm. length) is packed with a commercially available C18 stationary phase known to be useful for the resolution of polypeptides and proteins, and then is incorporated into an HPLC system. The system is equilibrated with elution buffer that comprises a mixture of 75% mobile phase A ($H_2O$ with 0.1% trifluoroacetic acid) and 25% mobile phase B (acetonitrile with 0.1% trifluoroacetic acid). The Tris-HCl solution of the product mixture from Example 21(a) is applied to the column, and the major products are separated and eluted using a gradient elution in which the percentage of the acetonitrile component is increased from 25%-55% over 120 minutes. Fractions are collected and analyzed by HPLC to determine the identity and purity of the product therein. Common fractions of each product are pooled, and the solvent is removed by rotary evaporation. The identity and purity of each product peak are determined by HPLC and mass spectrometry. The expected products consist of 3 multipeptide monoconjugates (conjugated at either Lys3 or Lys 14 or Lys 27 of each unit of BNP), 3 multipeptide diconjugate (conjugated at Lys3 & Lys14 or Lys14 & Lys27 or Lys27 & Lys3), 1 multipeptide triconjuagte (conjugated at Lys3, Lys14 and Lys 27) and 1 multipeptide tetraconjugate (conjugated at N-terminal of leader peptide, Lys3, Lys14 and Lys 27).

8.29.7 Preparation of Lys3-Hexyl-PEG7-Oligomer Conjugated BNP from Enzyme Cocktail Cleavage of Isolated Conjugate of Pro-Pentapeptide BNP-1

The conjugate, monoconjugated Lys3-hexyl-PEG7-oligomer pro-pentapeptide BNP-1, that is obtained using the procedure described in Example 3 is dissolved in 100 mM Tris-HCl Buffer, pH 7.6, and the resulting solution is analyzed by HPLC to determine the polypeptide concentration therein. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The crude mixture (1 mol eq.) is then allowed to react with trypsin ($1.39\times10^{-3}$ mol eq.) and carboxypeptidase B ($4.56\times10^{-4}$ mol eq.). After 30 minutes, the reaction is quenched by addition of 1% trifluoroacetic acid in acetonitrile. The products are processed and analyzed by HPLC. Retention time (compared to that of reference standards) and mass spectral analysis are used to determine identity. The expected products of the reaction are respective of each conjugates used. For example, Monoconjugated Lys3-hexyl-PEG7-oligomer-conjugated pro-pentapeptide BNP-1 is to provide Lys3-hexyl-PEG7-oligomer-conjugated BNP and Des Arg-His Lys3-hexyl-PEG7-oligomer-conjugated BNP.

8.29.8 Site Selective Conjugation at Lys3 of Pro-Pentapeptide BNP-1 in Borate Buffer/Organic Solvent Pro-pentapeptide BNP-1 (0.0195 mmol) can be dissolved in 5 mL of 50 mM boric acid. The solution can brought to pH 9.3 with 4N sodium hydroxide solution and added to 1 mL ethanol and adjusted to pH 10.4-10.9 with sodium hydroxide. To the above stirred solution can added a solution of activated methylheptaethylene glycol ((PEG7)-hexyl oligomer) (7.5× 0.0195 mmol) in 1 mL ethanol. The course of the conjugation (acylation) reaction is monitored by HPLC and the pH is maintained at pH 10.5 using 4N sodium hydroxide. When reaction appeared to be complete after 20 minutes, it is quenched by addition of 4N hydrochloric acid to pH 6.8. The reaction mixture is then processed and exchanged into 100 mM Tris-HCl Buffer, pH 7.6. The HPLC profile of the product mixture showed >40% conjugation at Lys3 of each unit of the BNP unit of pro-pentapeptide BNP-1

8.29.9 Site Selective Conjugation at Lys3 of Native hBNP in Borate Buffer/Organic Solvent Pro-pentapeptide BNP-1 (0.0195 mmol) is dissolved in 5 mL of 50 mM boric acid. The solution is brought to pH 9.3 with 4N sodium hydroxide solution and added to 1 mL ethanol and adjusted to pH 10.4-10.9 with sodium hydroxide. To the above stirred solution was added a solution of activated methylheptaethylene glycol ((PEG7)-hexyl oligomer) (1.6× 0.0195 mmol) in 1 mL ethanol. The course of the conjugation (acylation) reaction is monitored by HPLC and the pH is maintained at pH 10.5 using 4N sodium hydroxide. When reaction appeared to be complete after 20 minutes, it is quenched by addition of 4N hydrochloric acid to pH 6.8. The reaction mixture is then processed and exchanged into 100 mM Tris-HCl Buffer, pH 7.6. The HPLC profile of the product mixture is expected to show >40% conjugation at $Lys^3$ of the BNP molecule.

BIBLIOGRAPHY

The following references are incorporated herein in their entireties:

American Heart Association (2001). 2002 *Heart and Stroke Statistical Update*, Dallas, Tex., American Heart Association.

Anderson, W. R., N. Ekwuribe, A. Ansari, T. M. Harris and D. Surguladze (1999). "Structure activity relationship assessment of conjugated enkephalins in centrally mediated analgesia." Soc. for Neuroscience, Abstracts 25((1)): 180.

Association, A. H. (2001). 2002 Heart and stroke statistical update. Dallas, Tex., American Heart Association.

Chin, M. H. and L. Goldman (1997). "Correlates of early hospital readmission or death in patients with congestive heart failure." Am J Cardiol 79(12): 1640-4.

Ekwuribe, N. Conjugation-stabilized therapeutic agent compositions, delivery and diagnostic formulations comprising the same, and method of making and using the same. U.S. Pat. No. 5,681,811.

Ekwuribe, N., M. Ramaswamy, H. S. Allaudeen and J. S. Rajagopalan (1999). "Oral insulin delivery: hydrolysable amphiphilic oligomer conjugates prolong glucose reduction." Proceed. Intl. Symp. Control Release Bioactive Materials, Abstracts: 240.

Gaken et. al., (2000) Gene Therapy, 7:1979-1985.

Hussar, D. A. (2002). "New drugs of 2001." J Am Pharm Assoc (Wash) 42(2): 227-63; quiz 263-6.

Kawai, K., K. Hata, H. Takaoka, H. Kawai and M. Yokoyama (2001). "Plasma brain natriuretic peptide as a novel therapeutic indicator in idiopathic dilated cardiomyopathy during beta-blocker therapy: a potential of hormone-guided treatment." Am Heart J 141(6): 925-32.

Kayser, S. R. (2002). "The use of nesiritide in the management of acute decompensated heart failure." Prog Cardiovasc Nurs 17(2): 89-95.

Krishnan, B. R., M. Ramaswamy, J. S. Rajagopalan, W. R. Anderson, H. S. Allaudeen, S. Myung and N. Ekwuribe (1999). "Oral delivery of calcitonin by conjugation with amphiphilic oligomers." Proceed. Intl. Symp. Control Release Bioactive Materials, Abstracts: 43.

Krumholz, H. M., Y. T. Chen, Y. Wang, V. Vaccarino, M. J. Radford and R. I. Horwitz (2000). "Predictors of readmission among elderly survivors of admission with heart failure." Am Heart J 139(1 Pt 1): 72-7.

Krumholz, H. M., E. M. Parent, N. Tu, V. Vaccarino, Y. Wang, M. J. Radford and J. Hennen (1997). "Readmission after hospitalization for congestive heart failure among Medicare beneficiaries." Arch Intern Med 157(1): 99-104.

Maisel, A. S., P. Krishnaswamy, R. M. Nowak, J. McCord, J. E. Hollander, P. Duc, T. Omland, A. B. Storrow, W. T. Abraham, A. H. Wu, P. Clopton, P. G. Steg, A. Westheim, C. W. Knudsen, A. Perez, R. Kazanegra, H. C. Herrmann and P. A. McCullough (2002). "Rapid measurement of B-type natriuretic peptide in the emergency diagnosis of heart failure." N Engl J Med 347(3): 161-7.

Massie, B. M. and N. B. Shah (1997). "Evolving trends in the epidemiologic factors of heart failure: rationale for preventive strategies and comprehensive disease management." Am Heart J 133(6): 703-12.

McDonagh, T. A., S. D. Robb, D. R. Murdoch, J. J. Morton, I. Ford, C. E. Morrison, H. Tunstall-Pedoe, J. J. McMurray and H. J. Dargie (1998). "Biochemical detection of left-ventricular systolic dysfunction." Lancet 351(9095): 9-13.

McNairy, M., N. Gardetto, P. Clopton, A. Garcia, P. Krishnaswamy, R. Kazanegra, M. Ziegler and A. S. Maisel (2002). "Stability of B-type natriuretic peptide levels during exercise in patients with congestive heart failure: implications for outpatient monitoring with B-type natriuretic peptide." Am Heart J 143(3): 406-11.

Nagaya, N., T. Nishikimi, M. Uematsu, T. Satoh, S. Kyotani, F. Sakamaki, M. Kakishita, K. Fukushima, Y. Okano, N. Nakanishi, K. Miyatake and K. Kangawa (2000). "Plasma brain natriuretic peptide as a prognostic indicator in patients with primary pulmonary hypertension." Circulation 102(8): 865-70.

O'Connell, J. B. and M. R. Bristow (1994). "Economic impact of heart failure in the United States: time for a different approach." J Heart Lung Transplant 13(4): S107-12.

Packer, M. and H. M. Cohn (1999). "Consensus recommendations for the management of chronic heart failure. On behalf of the membership of the advisory council to improve outcomes nationwide in heart failure." Am J Cardiol 83(2A): 1A-38A.

Remingtons, The Science and Practice of Pharmacy (9th Edition, 1995)

Richards, A. M., M. G. Nicholls, T. G. Yandle, C. Frampton, E. A. Espiner, J. G. Turner, R. C. Buttimore, J. G. Lainchbury, J. M. Elliott, H. Ikram, I. G. Crozier and D. W. Smyth (1998). "Plasma N-terminal pro-brain natriuretic peptide and adrenomedullin: new neurohormonal predictors of left ventricular function and prognosis after myocardial infarction." Circulation 97(19): 1921-9.

Stewart, S., J. E. Marley and J. D. Horowitz (1999). "Effects of a multidisciplinary, home-based intervention on unplanned readmissions and survival among patients with chronic congestive heart failure: a randomised controlled study." Lancet 354(9184): 1077-83.

Sudoh, T., K. Kangawa, N. Minamino and H. Matsuo (1988). "A new natriuretic peptide in porcine brain." Nature 332 (6159): 78-81.

Sudoh, T., et. al., (1989), Biophys. Res. Com., 159 (3): 1427-1433.

Sudoh, T., et. al., (2002), U.S. Patent Application U.S. 2002/0086843A, EPO 542,863B1(1997)

Tsuchihashi, M., H. Tsutsui, K. Kodama, F. Kasagi, S. Setoguchi, M. Mohr, T. Kubota and A. Takeshita (2001). "Medical and socioenvironmental predictors of hospital readmission in patients with congestive heart failure." Am Heart J 142(4): E7.

Yamamoto, K., J. C. Burnett, Jr., M. Jougasaki, R. A. Nishimura, K. R. Bailey, Y. Saito, K. Nakao and M. M. Redfield (1996). "Superiority of brain natriuretic peptide as a hormonal marker of ventricular systolic and diastolic dysfunction and ventricular hypertrophy." Hypertension 28(6): 988-94.
U.S. Pat. No. 5,674,710—Seilhamer et. al.
U.S. Pat. No. 6,034,231—Tanaka, et. al.
U.S. Patent No 2003/0069186 A1—Burnett, Jr., et. al.
U.S. Pat. No. 6,492,560 B2—Wilbur et. al.
U.S. Pat. No. 6,013,630—Shimkets, et. al.
U.S. Pat. No. 6,586,396—Seilhamer, et. al.
U.S. Pat. No. 6,525,022—Lowe, et. al.
U.S. Pat. No. 6,028,055—Lowe, et al.
U.S. Pat. No. 5,114,923—Seilhamer et. al.
PCTUS0217567

```
                              SEQUENCE LISTING

<160> NUMBER OF SEQ ID NOS: 142

<210> SEQ ID NO 1
<211> LENGTH: 17
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (5)..(5)
<223> OTHER INFORMATION: Xaa is an amino acid to which a modifying
      moiety may be attached

<400> SEQUENCE: 1

Cys Phe Gly Arg Xaa Met Asp Arg Ile Ser Ser Ser Ser Gly Leu Gly
1               5                   10                  15

Cys

<210> SEQ ID NO 2
<211> LENGTH: 17
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (5)..(5)
<223> OTHER INFORMATION: Xaa is Lysine
<220> FEATURE:
<221> NAME/KEY: MISC_FEATURE
<222> LOCATION: (10)..(10)
<223> OTHER INFORMATION: Xaa is Ser or Lys
<220> FEATURE:
<221> NAME/KEY: MISC_FEATURE
<222> LOCATION: (11)..(11)
<223> OTHER INFORMATION: Xaa is Ser and may be present or absent
<220> FEATURE:
<221> NAME/KEY: MISC_FEATURE
<222> LOCATION: (12)..(12)
<223> OTHER INFORMATION: Xaa is Ser and may be present or absent
<220> FEATURE:
<221> NAME/KEY: MISC_FEATURE
<222> LOCATION: (13)..(13)
<223> OTHER INFORMATION: Xaa is Ser and may be present or absent

<400> SEQUENCE: 2

Cys Phe Gly Arg Xaa Met Asp Arg Ile Xaa Xaa Xaa Xaa Gly Leu Gly
1               5                   10                  15

Cys

<210> SEQ ID NO 3
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 3
```

```
Ser Ser Ser Ser
1

<210> SEQ ID NO 4
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 4

Lys Ser Ser Ser
1

<210> SEQ ID NO 5
<211> LENGTH: 17
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (5)..(5)
<223> OTHER INFORMATION: Xaa is any amino acid other than lysine,
      preferably arginine

<400> SEQUENCE: 5

Cys Phe Gly Arg Xaa Met Asp Arg Ile Ser Ser Ser Ser Gly Leu Gly
1               5                   10                  15

Cys

<210> SEQ ID NO 6
<211> LENGTH: 9
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (3)..(3)
<223> OTHER INFORMATION: Xaa is lysine or arginine

<400> SEQUENCE: 6

Ser Pro Xaa Met Val Gln Gly Ser Gly
1               5

<210> SEQ ID NO 7
<211> LENGTH: 7
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (3)..(3)
<223> OTHER INFORMATION: Xaa is lysine or arginine

<400> SEQUENCE: 7

Ser Pro Xaa Met Val Gln Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Natriuretic peptide
<220> FEATURE:
```

```
<221> NAME/KEY: MISC_FEATURE
<222> LOCATION: (3)..(3)
<223> OTHER INFORMATION: Xaa is lysine or arginine

<400> SEQUENCE: 8

Ser Pro Xaa Met Val Gln
1               5

<210> SEQ ID NO 9
<211> LENGTH: 5
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (3)..(3)
<223> OTHER INFORMATION: Xaa is lysine or arginine

<400> SEQUENCE: 9

Ser Pro Xaa Met Val
1               5

<210> SEQ ID NO 10
<211> LENGTH: 4
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (3)..(3)
<223> OTHER INFORMATION: Xaa is lysine or arginine

<400> SEQUENCE: 10

Ser Pro Xaa Met
1

<210> SEQ ID NO 11
<211> LENGTH: 8
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (2)..(2)
<223> OTHER INFORMATION: Xaa is lysine or arginine

<400> SEQUENCE: 11

Pro Xaa Met Val Gln Gly Ser Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (1)..(1)
<223> OTHER INFORMATION: Xaa is lysine or arginine

<400> SEQUENCE: 12

Xaa Met Val Gln Gly Ser Gly
1               5

<210> SEQ ID NO 13
```

```
<211> LENGTH: 6
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (1)..(1)
<223> OTHER INFORMATION: Xaa is lysine or arginine

<400> SEQUENCE: 13

Xaa Val Leu Arg Arg His
1               5

<210> SEQ ID NO 14
<211> LENGTH: 5
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (1)..(1)
<223> OTHER INFORMATION: Xaa is lysine or arginine

<400> SEQUENCE: 14

Xaa Val Leu Arg Arg
1               5

<210> SEQ ID NO 15
<211> LENGTH: 4
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (1)..(1)
<223> OTHER INFORMATION: Xaa is lysine or arginine

<400> SEQUENCE: 15

Xaa Val Leu Arg
1

<210> SEQ ID NO 16
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 16

Arg Val Leu Arg Arg
1               5

<210> SEQ ID NO 17
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 17

Arg Val Leu Arg
1

<210> SEQ ID NO 18
<211> LENGTH: 25
<212> TYPE: PRT
```

```
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (1)..(1)
<223> OTHER INFORMATION: Xaa is Lys or an amino acid other than Lys,
      wherein at least one of X1, X12 and X25 is Lys and at least one
      of X1, X12 and X25 is an amino acid other than Lys
<220> FEATURE:
<221> NAME/KEY: DISULFID
<222> LOCATION: (8)..(24)
<223> OTHER INFORMATION: may be conjugated by a disulfide bond
<220> FEATURE:
<221> NAME/KEY: MISC_FEATURE
<222> LOCATION: (12)..(12)
<223> OTHER INFORMATION: Xaa is Lys or an amino acid other than Lys,
      wherein at least one of X1, X12 and X25 is Lys and at least one
      of X1, X12 and X25 is an amino acid other than Lys
<220> FEATURE:
<221> NAME/KEY: MISC_FEATURE
<222> LOCATION: (25)..(25)
<223> OTHER INFORMATION: Xaa is Lys or an amino acid other than Lys,
      wherein at least one of X1, X12 and X25 is Lys and at least one
      of X1, X12 and X25 is an amino acid other than Lys

<400> SEQUENCE: 18

Xaa Met Val Gln Gly Ser Gly Cys Phe Gly Arg Xaa Met Asp Arg Ile
1               5                   10                  15

Ser Ser Ser Ser Gly Leu Gly Cys Xaa
            20                  25

<210> SEQ ID NO 19
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 19

Val Leu Arg Arg His
1               5

<210> SEQ ID NO 20
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 20

Val Leu Arg Arg
1

<210> SEQ ID NO 21
<211> LENGTH: 18
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (5)..(5)
<223> OTHER INFORMATION: Xaa is any amino acid or an unconjugated Lys,
      wherein at least one of X5 and X18 is an amino acid comprising a
      modifying moiety conjugation site coupled to the modifying moiety
<220> FEATURE:
<221> NAME/KEY: MISC_FEATURE
<222> LOCATION: (18)..(18)
<223> OTHER INFORMATION: Xaa is any amino acid or an unconjugated Lys,
      wherein at least one of X5 and X18 is an amino acid comprising a
      modifying moiety conjugation site coupled to the modifying moiety
```

```
<400> SEQUENCE: 21

Cys Phe Gly Arg Xaa Met Asp Arg Ile Ser Ser Ser Gly Leu Gly
1               5                   10                  15

Cys Xaa

<210> SEQ ID NO 22
<211> LENGTH: 17
<212> TYPE: PRT
<213> ORGANISM: Artificial Sequence
<220> FEATURE:
<223> OTHER INFORMATION: Natriuretic peptide

<400> SEQUENCE: 22

Cys Phe Gly Arg Lys Met Asp Arg Ile Ser Ser Ser Gly Leu Gly
1               5                   10                  15

Cys

<210> SEQ ID NO 23
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 23

Gln Gly Ser Gly
1

<210> SEQ ID NO 24
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 24

Val Gln Gly Ser Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Natriuretic peptide

<400> SEQUENCE: 25

Met Val Gln Gly Ser Gly
1               5

<210> SEQ ID NO 26
<211> LENGTH: 7
<212> TYPE: PRT
<213> ORGANISM: Artificial Sequence
<220> FEATURE:
<223> OTHER INFORMATION: Natriuretic peptide

<400> SEQUENCE: 26

Lys Met Val Gln Gly Ser Gly
1               5

<210> SEQ ID NO 27
<211> LENGTH: 8
<212> TYPE: PRT
```

```
<213> ORGANISM: Artificial Sequence
<220> FEATURE:
<223> OTHER INFORMATION: Natriuretic peptide

<400> SEQUENCE: 27

Pro Lys Met Val Gln Gly Ser Gly
1               5

<210> SEQ ID NO 28
<211> LENGTH: 9
<212> TYPE: PRT
<213> ORGANISM: Artificial Sequence
<220> FEATURE:
<223> OTHER INFORMATION: Natriuretic peptide

<400> SEQUENCE: 28

Ser Pro Lys Met Val Gln Gly Ser Gly
1               5

<210> SEQ ID NO 29
<211> LENGTH: 9
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (1)..(1)
<223> OTHER INFORMATION: Xaa is the 102 amino acid sequence of positions
      1-99 for the human BNP protein or a C-terminal portion thereof.

<400> SEQUENCE: 29

Ser Pro Lys Met Val Gln Gly Ser Gly
1               5

<210> SEQ ID NO 30
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 30

Lys Val Leu Arg
1

<210> SEQ ID NO 31
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 31

Lys Val Leu Arg Arg
1               5

<210> SEQ ID NO 32
<211> LENGTH: 6
<212> TYPE: PRT
<213> ORGANISM: Artificial Sequence
<220> FEATURE:
<223> OTHER INFORMATION: Natriuretic peptide

<400> SEQUENCE: 32

Lys Val Leu Arg Arg His
1               5
```

```
<210> SEQ ID NO 33
<211> LENGTH: 23
<212> TYPE: PRT
<213> ORGANISM: Artificial Sequence
<220> FEATURE:
<223> OTHER INFORMATION: Natriuretic peptide

<400> SEQUENCE: 33

Cys Phe Gly Arg Lys Met Asp Arg Ile Ser Ser Ser Ser Gly Leu Gly
1               5                   10                  15

Cys Lys Val Leu Arg Arg His
            20

<210> SEQ ID NO 34
<211> LENGTH: 9
<212> TYPE: PRT
<213> ORGANISM: Artificial Sequence
<220> FEATURE:
<223> OTHER INFORMATION: Natriuretic peptide

<400> SEQUENCE: 34

Ser Pro Lys Met Val Gln Gly Ser Gly
1               5

<210> SEQ ID NO 35
<211> LENGTH: 17
<212> TYPE: PRT
<213> ORGANISM: Artificial Sequence
<220> FEATURE:
<223> OTHER INFORMATION: Natriuretic peptide
<220> FEATURE:
<221> NAME/KEY: DISULFID
<222> LOCATION: (1)..(17)

<400> SEQUENCE: 35

Cys Phe Gly Arg Arg Leu Asp Arg Ile Gly Ser Leu Ser Gly Leu Gly
1               5                   10                  15

Cys

<210> SEQ ID NO 36
<211> LENGTH: 6
<212> TYPE: PRT
<213> ORGANISM: Artificial Sequence
<220> FEATURE:
<223> OTHER INFORMATION: Natriuretic peptide

<400> SEQUENCE: 36

Asn Val Leu Arg Arg Tyr
1               5

<210> SEQ ID NO 37
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 37

Asn Val Leu Arg Arg
1               5

<210> SEQ ID NO 38
<211> LENGTH: 5
<212> TYPE: PRT
<213> ORGANISM: Artificial Sequence
<220> FEATURE:
```

<223> OTHER INFORMATION: Natriuretic peptide

<400> SEQUENCE: 38

Asn Val Leu Arg Tyr
1               5

<210> SEQ ID NO 39
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 39

Asn Val Leu Arg
1

<210> SEQ ID NO 40
<211> LENGTH: 3
<212> TYPE: PRT
<213> ORGANISM: Artificial Sequence
<220> FEATURE:
<223> OTHER INFORMATION: Natriuretic peptide

<400> SEQUENCE: 40

Asn Val Leu
1

<210> SEQ ID NO 41
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 41

Asn Ser Phe Arg Tyr
1               5

<210> SEQ ID NO 42
<211> LENGTH: 19
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (5)..(5)
<223> OTHER INFORMATION: Xaa is lysine or arginine
<220> FEATURE:
<221> NAME/KEY: MISC_FEATURE
<222> LOCATION: (6)..(6)
<223> OTHER INFORMATION: Xaa is leucine or methionine
<220> FEATURE:
<221> NAME/KEY: MISC_FEATURE
<222> LOCATION: (12)..(12)
<223> OTHER INFORMATION: Xaa is glycine or serine
<220> FEATURE:
<221> NAME/KEY: MISC_FEATURE
<222> LOCATION: (14)..(14)
<223> OTHER INFORMATION: Xaa is leucine or serine

<400> SEQUENCE: 42

Cys Phe Gly Arg Xaa Xaa Asp Arg Ile Lys Met Xaa Ser Xaa Ser Gly
1               5                   10                  15

Leu Gly Cys

<210> SEQ ID NO 43

```
<211> LENGTH: 4
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (1)..(1)
<223> OTHER INFORMATION: Xaa is arginine, histidine or glutamine
<220> FEATURE:
<221> NAME/KEY: MISC_FEATURE
<222> LOCATION: (2)..(2)
<223> OTHER INFORMATION: Xaa is aspartic acid, lysine or glycine

<400> SEQUENCE: 43

Xaa Xaa Ser Gly
1

<210> SEQ ID NO 44
<211> LENGTH: 5
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (1)..(1)
<223> OTHER INFORMATION: Xaa is methionine or valine
<220> FEATURE:
<221> NAME/KEY: MISC_FEATURE
<222> LOCATION: (2)..(2)
<223> OTHER INFORMATION: Xaa is arginine, histidine, or glutamine
<220> FEATURE:
<221> NAME/KEY: MISC_FEATURE
<222> LOCATION: (3)..(3)
<223> OTHER INFORMATION: Xaa is aspartic acid, lysine or glycine

<400> SEQUENCE: 44

Xaa Xaa Xaa Ser Gly
1               5

<210> SEQ ID NO 45
<211> LENGTH: 6
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (1)..(1)
<223> OTHER INFORMATION: Xaa is threonine or methionine
<220> FEATURE:
<221> NAME/KEY: MISC_FEATURE
<222> LOCATION: (2)..(2)
<223> OTHER INFORMATION: Xaa is methionine or valine
<220> FEATURE:
<221> NAME/KEY: MISC_FEATURE
<222> LOCATION: (3)..(3)
<223> OTHER INFORMATION: Xaa is arginine, histidine or glutamine
<220> FEATURE:
<221> NAME/KEY: MISC_FEATURE
<222> LOCATION: (4)..(4)
<223> OTHER INFORMATION: Xaa is aspartic acid, lysine or glycine

<400> SEQUENCE: 45

Xaa Xaa Xaa Xaa Ser Gly
1               5

<210> SEQ ID NO 46
<211> LENGTH: 7
<212> TYPE: PRT
<213> ORGANISM: Artificial Sequence
<220> FEATURE:
```

```
<223> OTHER INFORMATION: Natriuretic peptide
<220> FEATURE:
<221> NAME/KEY: MISC_FEATURE
<222> LOCATION: (2)..(2)
<223> OTHER INFORMATION: Xaa is threonine or methionine
<220> FEATURE:
<221> NAME/KEY: MISC_FEATURE
<222> LOCATION: (3)..(3)
<223> OTHER INFORMATION: Xaa is methionine or valine
<220> FEATURE:
<221> NAME/KEY: MISC_FEATURE
<222> LOCATION: (4)..(4)
<223> OTHER INFORMATION: Xaa is arginine, histidine or glutamine
<220> FEATURE:
<221> NAME/KEY: MISC_FEATURE
<222> LOCATION: (5)..(5)
<223> OTHER INFORMATION: Xaa is aspartic acid, lysine or glycine

<400> SEQUENCE: 46

Lys Xaa Xaa Xaa Xaa Ser Gly
1               5

<210> SEQ ID NO 47
<211> LENGTH: 8
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (3)..(3)
<223> OTHER INFORMATION: Xaa is threonine or methionine
<220> FEATURE:
<221> NAME/KEY: MISC_FEATURE
<222> LOCATION: (4)..(4)
<223> OTHER INFORMATION: Xaa is methionine and valine
<220> FEATURE:
<221> NAME/KEY: MISC_FEATURE
<222> LOCATION: (5)..(5)
<223> OTHER INFORMATION: Xaa is arginine, histidine or glutamine
<220> FEATURE:
<221> NAME/KEY: MISC_FEATURE
<222> LOCATION: (6)..(6)
<223> OTHER INFORMATION: Xaa is aspartic acid, lysine or glycine

<400> SEQUENCE: 47

Pro Lys Xaa Xaa Xaa Xaa Ser Gly
1               5

<210> SEQ ID NO 48
<211> LENGTH: 9
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (4)..(4)
<223> OTHER INFORMATION: Xaa is threonine or methionine
<220> FEATURE:
<221> NAME/KEY: MISC_FEATURE
<222> LOCATION: (5)..(5)
<223> OTHER INFORMATION: Xaa is methionine or valine
<220> FEATURE:
<221> NAME/KEY: MISC_FEATURE
<222> LOCATION: (6)..(6)
<223> OTHER INFORMATION: Xaa is arginine, histidine or glutamine
<220> FEATURE:
<221> NAME/KEY: MISC_FEATURE
<222> LOCATION: (7)..(7)
<223> OTHER INFORMATION: Xaa is aspartic acid, lysine or glycine

<400> SEQUENCE: 48

Ser Pro Lys Xaa Xaa Xaa Xaa Ser Gly
```

<210> SEQ ID NO 49
<211> LENGTH: 4
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (1)..(1)
<223> OTHER INFORMATION: Xaa is asparagine or lysine

<400> SEQUENCE: 49

Xaa Val Leu Arg
1

<210> SEQ ID NO 50
<211> LENGTH: 5
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (1)..(1)
<223> OTHER INFORMATION: Xaa is asparagine or lysine
<220> FEATURE:
<221> NAME/KEY: MISC_FEATURE
<222> LOCATION: (5)..(5)
<223> OTHER INFORMATION: Xaa is arginine or lysine

<400> SEQUENCE: 50

Xaa Val Leu Arg Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (1)..(1)
<223> OTHER INFORMATION: Xaa is Asn or Lys
<220> FEATURE:
<221> NAME/KEY: misc_feature
<222> LOCATION: (5)..(5)
<223> OTHER INFORMATION: Xaa is Arg or Lys
<220> FEATURE:
<221> NAME/KEY: misc_feature
<222> LOCATION: (6)..(6)
<223> OTHER INFORMATION: Xaa is Tyr or His

<400> SEQUENCE: 51

Xaa Val Leu Arg Xaa Xaa
1               5

<210> SEQ ID NO 52
<211> LENGTH: 20
<212> TYPE: PRT
<213> ORGANISM: Artificial Sequence
<220> FEATURE:
<223> OTHER INFORMATION: Natriuretic peptide

<400> SEQUENCE: 52

Asp Ser Gly Cys Phe Gly Arg Arg Leu Asp Arg Ile Gly Ser Leu Ser
1               5                   10                  15

Gly Leu Gly Cys

-continued

```
<210> SEQ ID NO 53
<211> LENGTH: 6
<212> TYPE: PRT
<213> ORGANISM: Artificial Sequence
<220> FEATURE:
<223> OTHER INFORMATION: Natriuretic peptide

<400> SEQUENCE: 53

Asn Val Leu Arg Arg Tyr
1               5

<210> SEQ ID NO 54
<211> LENGTH: 23
<212> TYPE: PRT
<213> ORGANISM: Artificial Sequence
<220> FEATURE:
<223> OTHER INFORMATION: Natriuretic peptide
<220> FEATURE:
<221> NAME/KEY: DISULFID
<222> LOCATION: (1)..(17)

<400> SEQUENCE: 54

Cys Phe Gly Arg Lys Met Asp Arg Ile Ser Ser Ser Ser Gly Leu Gly
1               5                   10                  15

Cys Lys Val Leu Arg Arg His
            20

<210> SEQ ID NO 55
<211> LENGTH: 9
<212> TYPE: PRT
<213> ORGANISM: Artificial Sequence
<220> FEATURE:
<223> OTHER INFORMATION: Natriuretic peptide

<400> SEQUENCE: 55

Ser Pro Lys Met Val Gln Gly Ser Gly
1               5

<210> SEQ ID NO 56
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 56

Glu Asp Ala Gly Glu
1               5

<210> SEQ ID NO 57
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 57

Arg Thr Arg Arg
1

<210> SEQ ID NO 58
<211> LENGTH: 4
<212> TYPE: PRT
<213> ORGANISM: Artificial Sequence
<220> FEATURE:
```

```
<223> OTHER INFORMATION: Natriuretic peptide
<220> FEATURE:
<221> NAME/KEY: misc_feature
<222> LOCATION: (2)..(2)
<223> OTHER INFORMATION: Xaa is any amino acid

<400> SEQUENCE: 58

Arg Xaa Lys Arg
1

<210> SEQ ID NO 59
<211> LENGTH: 10
<212> TYPE: PRT
<213> ORGANISM: Artificial Sequence
<220> FEATURE:
<223> OTHER INFORMATION: Natriuretic peptide

<400> SEQUENCE: 59

His His His His His His Ala Asp Gly Glu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Natriuretic peptide

<400> SEQUENCE: 60

His His His His His His Ala Asp Arg Thr Arg Arg
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (10)..(10)
<223> OTHER INFORMATION: Xaa is any amino acid

<400> SEQUENCE: 61

His His His His His His Ala Asp Arg Xaa Lys Arg
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Natriuretic peptide

<400> SEQUENCE: 62

His His His His His His Ala Asp Arg Glu Arg Arg
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Natriuretic peptide

<400> SEQUENCE: 63

His His His His His His Ala Asp Arg Val
1               5                   10
```

-continued

<210> SEQ ID NO 64
<211> LENGTH: 9
<212> TYPE: PRT
<213> ORGANISM: Artificial Sequence
<220> FEATURE:
<223> OTHER INFORMATION: Natriuretic peptide

<400> SEQUENCE: 64

His His His His His His Ala Asp Lys
1               5

<210> SEQ ID NO 65
<211> LENGTH: 10
<212> TYPE: PRT
<213> ORGANISM: Artificial Sequence
<220> FEATURE:
<223> OTHER INFORMATION: Natriuretic peptide

<400> SEQUENCE: 65

His His His His His His Ala Asp Lys Ile
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Natriuretic peptide

<400> SEQUENCE: 66

His His His His His His Ala Asp Arg Thr
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Natriuretic peptide

<400> SEQUENCE: 67

His His His His His His Ala Asp Arg Ile
1               5                   10

<210> SEQ ID NO 68
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 68

Ala Asp Gly Glu
1

<210> SEQ ID NO 69
<211> LENGTH: 10
<212> TYPE: PRT
<213> ORGANISM: Artificial Sequence
<220> FEATURE:
<223> OTHER INFORMATION: Natriuretic peptide

<400> SEQUENCE: 69

His His His His His His Ala Asp Gly Glu
1               5                   10

```
<210> SEQ ID NO 70
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 70

Arg Glu Arg Arg
1

<210> SEQ ID NO 71
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 71

Glu Ala Asp Gly Glu
1               5

<210> SEQ ID NO 72
<211> LENGTH: 13
<212> TYPE: PRT
<213> ORGANISM: Artificial Sequence
<220> FEATURE:
<223> OTHER INFORMATION: Natriuretic peptide

<400> SEQUENCE: 72

His His His His His His Ala Asp Gly Arg Thr Arg Arg
1               5                   10

<210> SEQ ID NO 73
<211> LENGTH: 4
<212> TYPE: PRT
<213> ORGANISM: Artificial Sequence
<220> FEATURE:
<223> OTHER INFORMATION: Natriuretic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 73

Arg Xaa Leu Arg
1

<210> SEQ ID NO 74
<211> LENGTH: 11
<212> TYPE: PRT
<213> ORGANISM: Artificial Sequence
<220> FEATURE:
<223> OTHER INFORMATION: Natriuretic peptide

<400> SEQUENCE: 74

His His His His His His Ala Asp Gly Arg Val
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Natriuretic peptide

<400> SEQUENCE: 75
```

```
His His His His His His Ala Asp Gly Asp Lys
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Natriuretic peptide

<400> SEQUENCE: 76

His His His His His His Ala Asp Gly Lys Ile
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Natriuretic peptide

<400> SEQUENCE: 77

His His His His His His Ala Asp Gly Arg Thr
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Natriuretic peptide

<400> SEQUENCE: 78

His His His His His His Ala Asp Gly Arg Ile
1               5                   10

<210> SEQ ID NO 79
<211> LENGTH: 8
<212> TYPE: PRT
<213> ORGANISM: Artificial Sequence
<220> FEATURE:
<223> OTHER INFORMATION: Natriuretic peptide

<400> SEQUENCE: 79

Arg Arg Asp Ala Glu Asp Pro Arg
1               5

<210> SEQ ID NO 80
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 80

Glu Gly Asp Arg Arg
1               5

<210> SEQ ID NO 81
<211> LENGTH: 11
<212> TYPE: PRT
<213> ORGANISM: Artificial Sequence
<220> FEATURE:
<223> OTHER INFORMATION: Natriuretic peptide

<400> SEQUENCE: 81

His His His His His His Glu Gly Asp Arg Arg
```

```
1               5               10
```

<210> SEQ ID NO 82
<211> LENGTH: 8
<212> TYPE: PRT
<213> ORGANISM: Artificial Sequence
<220> FEATURE:
<223> OTHER INFORMATION: Natriuretic peptide

<400> SEQUENCE: 82

```
Arg Arg Asp Ala Glu Asp Arg Arg
1               5
```

<210> SEQ ID NO 83
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 83

```
Glu Gly Asp Arg Arg
1               5
```

<210> SEQ ID NO 84
<211> LENGTH: 6
<212> TYPE: PRT
<213> ORGANISM: Artificial Sequence
<220> FEATURE:
<223> OTHER INFORMATION: Natriuretic peptide

<400> SEQUENCE: 84

```
His His His His His His
1               5
```

<210> SEQ ID NO 85
<211> LENGTH: 8
<212> TYPE: PRT
<213> ORGANISM: Artificial Sequence
<220> FEATURE:
<223> OTHER INFORMATION: Natriuretic peptide

<400> SEQUENCE: 85

```
Arg Gly Asp Ala Glu Asp Pro Arg
1               5
```

<210> SEQ ID NO 86
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 86

```
Glu Gly Asp Pro Arg
1               5
```

<210> SEQ ID NO 87
<211> LENGTH: 11
<212> TYPE: PRT
<213> ORGANISM: Artificial Sequence
<220> FEATURE:
<223> OTHER INFORMATION: Natriuretic peptide

<400> SEQUENCE: 87

```
His His His His His His Glu Gly Asp Pro Arg
1               5                   10
```

```
<210> SEQ ID NO 88
<211> LENGTH: 9
<212> TYPE: PRT
<213> ORGANISM: Artificial Sequence
<220> FEATURE:
<223> OTHER INFORMATION: Natriuretic peptide

<400> SEQUENCE: 88

Ala Arg Gly Asp Ala Glu Asp Pro Arg
1               5

<210> SEQ ID NO 89
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 89

Glu Gly Asp Pro Arg
1               5

<210> SEQ ID NO 90
<211> LENGTH: 11
<212> TYPE: PRT
<213> ORGANISM: Artificial Sequence
<220> FEATURE:
<223> OTHER INFORMATION: Natriuretic peptide

<400> SEQUENCE: 90

His His His His His His Glu Gly Asp Pro Arg
1               5                   10

<210> SEQ ID NO 91

<400> SEQUENCE: 91

000

<210> SEQ ID NO 92
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 92

Asp Asp Ala Gly Glu
1               5

<210> SEQ ID NO 93
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 93

Ala Asp Gly Glu
1

<210> SEQ ID NO 94
<211> LENGTH: 4
<212> TYPE: PRT
<213> ORGANISM: Artificial Sequence
<220> FEATURE:
```

```
<223> OTHER INFORMATION: Natriuretic peptide

<400> SEQUENCE: 94

Glu Ala Gly Glu
1

<210> SEQ ID NO 95
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 95

Glu Gly Asp Ala
1

<210> SEQ ID NO 96
<211> LENGTH: 11
<212> TYPE: PRT
<213> ORGANISM: Artificial Sequence
<220> FEATURE:
<223> OTHER INFORMATION: Natriuretic peptide

<400> SEQUENCE: 96

Glu Gly Asp Ala His His His His His His Glu
1               5                   10

<210> SEQ ID NO 97
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 97

Glu Gly Asp Ala Glu
1               5

<210> SEQ ID NO 98
<211> LENGTH: 11
<212> TYPE: PRT
<213> ORGANISM: Artificial Sequence
<220> FEATURE:
<223> OTHER INFORMATION: Natriuretic peptide

<400> SEQUENCE: 98

Glu His His His His His His Ala Asp Gly Glu
1               5                   10

<210> SEQ ID NO 99
<211> LENGTH: 32
<212> TYPE: PRT
<213> ORGANISM: Artificial Sequence
<220> FEATURE:
<223> OTHER INFORMATION: Natriuretic peptide
<220> FEATURE:
<221> NAME/KEY: DISULFID
<222> LOCATION: (10)..(26)

<400> SEQUENCE: 99

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
                20                  25                  30
```

```
<210> SEQ ID NO 100
<211> LENGTH: 32
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (31)..(31)
<223> OTHER INFORMATION: Xaa is lysine or an amino acid other than
      arginine, wherein if Xaa is lysine, a second modifying moiety
      conjugation site is provided.

<400> SEQUENCE: 100

Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asn Ser Phe Xaa Tyr
            20                  25                  30

<210> SEQ ID NO 101
<211> LENGTH: 32
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (3)..(3)
<223> OTHER INFORMATION: Xaa is an available site for conjugation with
      a modifying moiety, and may be substituted with a residue other
      than Lys, such as Arg.
<220> FEATURE:
<221> NAME/KEY: misc_feature
<222> LOCATION: (7)..(7)
<223> OTHER INFORMATION: Xaa is an available site for conjugation with a
      modifying moiety, and may be substituted with a residue other than
      Lys, such as Arg.
<220> FEATURE:
<221> NAME/KEY: DISULFID
<222> LOCATION: (10)..(26)
<220> FEATURE:
<221> NAME/KEY: misc_feature
<222> LOCATION: (31)..(31)
<223> OTHER INFORMATION: Xaa is an available site for conjugation with a
      modifying moiety, and may be substituted with a residue other than
      Lys, such as Arg.

<400> SEQUENCE: 101

Ser Pro Xaa Met Met His Xaa Gly Gly Cys Phe Gly Arg Arg Leu Asp
1               5                   10                  15

Arg Ile Gly Ser Leu Ser Gly Leu Gly Cys Asn Val Leu Arg Xaa Tyr
            20                  25                  30

<210> SEQ ID NO 102
<211> LENGTH: 38
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (3)..(3)
<223> OTHER INFORMATION: X3 is an available site for conjugation with a
      modifying moiety. Preferably, when X3 is lysine, X11 is arginine
      or an  amino acid other than lysine
<220> FEATURE:
<221> NAME/KEY: misc_feature
<222> LOCATION: (11)..(11)
<223> OTHER INFORMATION: X11 is an available site for conjugation with a
      modifying moiety. Preferably, when X3 is lysine, X11 is arginine
      or an amino acid other than lysine

<400> SEQUENCE: 102
```

```
Glu Val Xaa Tyr Asp Pro Cys Phe Gly His Xaa Ile Asp Arg Ile Asn
1               5                   10                  15

His Val Ser Asn Leu Gly Cys Pro Ser Leu Arg Asp Pro Arg Pro Asn
            20                  25                  30

Ala Pro Ser Thr Ser Ala
            35

<210> SEQ ID NO 103
<211> LENGTH: 22
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (4)..(4)
<223> OTHER INFORMATION: Xaa is a modifying moiety conjugation site and
      is either Lys or Arg
<220> FEATURE:
<221> NAME/KEY: misc_feature
<222> LOCATION: (10)..(10)
<223> OTHER INFORMATION: Xaa is a modifying moiety conjugation site and
      is either Lys or Arg

<400> SEQUENCE: 103

Gly Leu Ser Xaa Gly Cys Phe Gly Leu Xaa Leu Asp Arg Ile Gly Ser
1               5                   10                  15

Met Ser Gly Leu Gly Cys
            20

<210> SEQ ID NO 104
<211> LENGTH: 28
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (12)..(12)
<223> OTHER INFORMATION: Xaa is Met or Ile

<400> SEQUENCE: 104

Ser Leu Arg Arg Ser Ser Cys Phe Gly Gly Arg Xaa Asp Arg Ile Gly
1               5                   10                  15

Ala Gln Ser Gly Leu Gly Cys Asn Ser Phe Arg Tyr
            20                  25

<210> SEQ ID NO 105
<211> LENGTH: 17
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (5)..(5)
<223> OTHER INFORMATION: Xaa is an amino acid other than Lys, or X is
      Arg or Gly.

<400> SEQUENCE: 105

Cys Phe Gly Arg Xaa Met Asp Arg Ile Ser Ser Ser Ser Gly Leu Gly
1               5                   10                  15

Cys

<210> SEQ ID NO 106
<211> LENGTH: 26
```

```
<212> TYPE: PRT
<213> ORGANISM: Artificial Sequence
<220> FEATURE:
<223> OTHER INFORMATION: Natriuretic peptide

<400> SEQUENCE: 106

Ser Pro Arg Met Val Gln Gly Ser Gly Cys Phe Gly Arg Lys Met Asp
1               5                   10                  15

Arg Ile Ser Ser Ser Ser Gly Leu Gly Cys
            20                  25

<210> SEQ ID NO 107
<211> LENGTH: 32
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (3)..(3)
<223> OTHER INFORMATION: X3 is an amino acid other than Lys. In some
      embodiments, X3, X14 and X27 are independently Arg or Gly.  In
      other embodiments, X3 is Lys, X14 and X27 are independently Arg
      or Gly. Preferedly, at least one of X3, X14 and X27 is Lys.
<220> FEATURE:
<221> NAME/KEY: misc_feature
<222> LOCATION: (14)..(14)
<223> OTHER INFORMATION: X14 is an amino acid other than Lys. In some
      embodiments, X3, X14 and X27 are independently Arg or Gly.  In
      other embodiments, X3 is Lys, X14 and X27 are independently Arg or
      Gly. Preferedly, at least one of X3, X14 and X27 is Lys.
<220> FEATURE:
<221> NAME/KEY: misc_feature
<222> LOCATION: (27)..(27)
<223> OTHER INFORMATION: X27 is an amino acid other than Lys. In some
      embodiments, X3, X14 and X27 are independently Arg or Gly.  In
      other embodiments, X3 is Lys, X14 and X27 are independently Arg or
      Gly.  Preferedly, at least one of X3, X14 and X27 is Lys.

<400> SEQUENCE: 107

Ser Pro Xaa Met Val Gln Gly Ser Gly Cys Phe Gly Arg Xaa Met Asp
1               5                   10                  15

Arg Ile Ser Ser Ser Ser Gly Leu Gly Cys Xaa Val Leu Arg Arg His
            20                  25                  30

<210> SEQ ID NO 108
<211> LENGTH: 33
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (1)..(1)
<223> OTHER INFORMATION: Xaa is a C-terminus modification site (Ser)
<220> FEATURE:
<221> NAME/KEY: misc_feature
<222> LOCATION: (15)..(15)
<223> OTHER INFORMATION: Xaa is an amino acid other than lysine
<220> FEATURE:
<221> NAME/KEY: misc_feature
<222> LOCATION: (28)..(28)
<223> OTHER INFORMATION: Xaa is an amino acid other than lysine

<400> SEQUENCE: 108

Xaa Ser Pro Lys Met Val Gln Gly Ser Gly Cys Phe Gly Arg Xaa Met
1               5                   10                  15

Asp Arg Ile Ser Ser Ser Ser Gly Leu Gly Cys Xaa Val Leu Arg Arg
            20                  25                  30

His
```

```
<210> SEQ ID NO 109
<211> LENGTH: 17
<212> TYPE: PRT
<213> ORGANISM: Artificial Sequence
<220> FEATURE:
<223> OTHER INFORMATION: Natriuretic peptide

<400> SEQUENCE: 109

Cys Phe Gly Arg Arg Met Asp Arg Ile Ser Ser Ser Ser Gly Leu Gly
1               5                   10                  15

Cys

<210> SEQ ID NO 110
<211> LENGTH: 10
<212> TYPE: PRT
<213> ORGANISM: Artificial Sequence
<220> FEATURE:
<223> OTHER INFORMATION: Natriuretic peptide

<400> SEQUENCE: 110

Ser Pro Lys Met Val Gln Gly Ser Gly Cys
1               5                   10

<210> SEQ ID NO 111
<211> LENGTH: 9
<212> TYPE: PRT
<213> ORGANISM: Artificial Sequence
<220> FEATURE:
<223> OTHER INFORMATION: Natriuretic peptide

<400> SEQUENCE: 111

Pro Lys Met Val Gln Gly Ser Gly Cys
1               5

<210> SEQ ID NO 112
<211> LENGTH: 8
<212> TYPE: PRT
<213> ORGANISM: Artificial Sequence
<220> FEATURE:
<223> OTHER INFORMATION: Natriuretic peptide

<400> SEQUENCE: 112

Lys Met Val Gln Gly Ser Gly Cys
1               5

<210> SEQ ID NO 113
<211> LENGTH: 7
<212> TYPE: PRT
<213> ORGANISM: Artificial Sequence
<220> FEATURE:
<223> OTHER INFORMATION: Natriuretic peptide

<400> SEQUENCE: 113

Met Val Gln Gly Ser Gly Cys
1               5

<210> SEQ ID NO 114
<211> LENGTH: 6
<212> TYPE: PRT
<213> ORGANISM: Artificial Sequence
<220> FEATURE:
<223> OTHER INFORMATION: Natriuretic peptide

<400> SEQUENCE: 114

Val Gln Gly Ser Gly Cys
```

```
<210> SEQ ID NO 115
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 115

Gln Gly Ser Gly Cys
1               5

<210> SEQ ID NO 116
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 116

Gly Ser Gly Cys
1

<210> SEQ ID NO 117
<211> LENGTH: 4
<212> TYPE: PRT
<213> ORGANISM: Artificial Sequence
<220> FEATURE:
<223> OTHER INFORMATION: Natriuretic peptide

<400> SEQUENCE: 117

Lys Met Val Gln
1

<210> SEQ ID NO 118
<211> LENGTH: 5
<212> TYPE: PRT
<213> ORGANISM: Artificial Sequence
<220> FEATURE:
<223> OTHER INFORMATION: Natriuretic peptide

<400> SEQUENCE: 118

Lys Met Val Gln Gly
1               5

<210> SEQ ID NO 119
<211> LENGTH: 6
<212> TYPE: PRT
<213> ORGANISM: Artificial Sequence
<220> FEATURE:
<223> OTHER INFORMATION: Natriuretic peptide

<400> SEQUENCE: 119

Lys Met Val Gln Gly Ser
1               5

<210> SEQ ID NO 120
<211> LENGTH: 8
<212> TYPE: PRT
<213> ORGANISM: Artificial Sequence
<220> FEATURE:
<223> OTHER INFORMATION: Natriuretic peptide

<400> SEQUENCE: 120

Lys Met Val Gln Gly Ser Gly Cys
1               5
```

<210> SEQ ID NO 121
<211> LENGTH: 29
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (3)..(3)
<223> OTHER INFORMATION: Xaa is Arg, or an amino acid other than Lys

<400> SEQUENCE: 121

Ser Pro Xaa Met Val Gln Gly Ser Gly Cys Phe Gly Arg Lys Met Asp
1               5                   10                  15

Arg Ile Ser Ser Ser Ser Gly Leu Gly Cys Lys Val Leu
            20                  25

<210> SEQ ID NO 122
<211> LENGTH: 26
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (3)..(3)
<223> OTHER INFORMATION: Xaa is Arg, Gly, or another amino acid other
      than Lys.

<400> SEQUENCE: 122

Ser Pro Xaa Met Val Gln Gly Ser Gly Cys Phe Gly Arg Lys Met Asp
1               5                   10                  15

Arg Ile Ser Ser Ser Ser Gly Leu Gly Cys
            20                  25

<210> SEQ ID NO 123
<211> LENGTH: 23
<212> TYPE: PRT
<213> ORGANISM: Artificial Sequence
<220> FEATURE:
<223> OTHER INFORMATION: Natriuretic peptide

<400> SEQUENCE: 123

Cys Phe Gly Arg Arg Met Asp Arg Ile Ser Ser Ser Ser Gly Leu Gly
1               5                   10                  15

Cys Arg Val Leu Arg Arg His
            20

<210> SEQ ID NO 124
<211> LENGTH: 17
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (5)..(5)
<223> OTHER INFORMATION: Xaa is Arg or an amino acid other than Lys.
<220> FEATURE:
<221> NAME/KEY: misc_feature
<222> LOCATION: (10)..(10)
<223> OTHER INFORMATION: Xaa is any amino acid.
<220> FEATURE:
<221> NAME/KEY: misc_feature
<222> LOCATION: (11)..(11)
<223> OTHER INFORMATION: Xaa is any amino acid and may be absent or
      present
<220> FEATURE:

```
<221> NAME/KEY: misc_feature
<222> LOCATION: (12)..(12)
<223> OTHER INFORMATION: Xaa is any amino acid and may be absent or
      present
<220> FEATURE:
<221> NAME/KEY: misc_feature
<222> LOCATION: (13)..(13)
<223> OTHER INFORMATION: Xaa is any amino acid and may be absent or
      present

<400> SEQUENCE: 124

Cys Phe Gly Arg Xaa Met Asp Arg Ile Xaa Xaa Xaa Xaa Gly Leu Gly
1               5                   10                  15

Cys

<210> SEQ ID NO 125
<211> LENGTH: 32
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (30)..(30)
<223> OTHER INFORMATION: Xaa is Lys or an amino acid other than Arg.

<400> SEQUENCE: 125

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Arg Xaa Arg His
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (27)..(27)
<223> OTHER INFORMATION: Xaa  is Arg or an amino acid other than Lys.

<400> SEQUENCE: 126

Ser Pro Lys Met Val Gln Gly Ser Gly Cys Phe Gly Arg Lys Met Asp
1               5                   10                  15

Arg Ile Ser Ser Ser Ser Gly Leu Gly Cys Xaa Val Leu Arg Arg His
            20                  25                  30

<210> SEQ ID NO 127
<211> LENGTH: 33
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (33)..(33)
<223> OTHER INFORMATION: Xaa is Lys or Cys

<400> SEQUENCE: 127

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

Xaa
```

```
<210> SEQ ID NO 128

<400> SEQUENCE: 128

000

<210> SEQ ID NO 129
<211> LENGTH: 26
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (3)..(3)
<223> OTHER INFORMATION: Xaa is arginine or an amino acid other than
      lysine
<220> FEATURE:
<221> NAME/KEY: misc_feature
<222> LOCATION: (14)..(14)
<223> OTHER INFORMATION: Xaa is arginine or an amino acid other than
      lysine.
<220> FEATURE:
<221> NAME/KEY: misc_feature
<222> LOCATION: (23)..(23)
<223> OTHER INFORMATION: Xaa23 is Gly, Met, Leu, Phe, Ile or a
      conservative substitutions thereof.
<220> FEATURE:
<221> NAME/KEY: misc_feature
<222> LOCATION: (24)..(24)
<223> OTHER INFORMATION: Xaa is Leu, Trp, Tyr, and Phe or a conservative
      substitutions thereof.
<220> FEATURE:
<221> NAME/KEY: misc_feature
<222> LOCATION: (25)..(25)
<223> OTHER INFORMATION: Xaa is Gly, Arg, or a conservative substitution
      thereof.

<400> SEQUENCE: 129

Ser Pro Xaa Met Val Gln Gly Ser Gly Cys Phe Gly Arg Xaa Met Asp
1               5                   10                  15

Arg Ile Ser Ser Ser Ser Xaa Xaa Xaa Cys
            20                  25

<210> SEQ ID NO 130
<211> LENGTH: 22
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (9)..(9)
<223> OTHER INFORMATION: Xaa is Thr, Ala, Arg, His, Pro, or Glu.
<220> FEATURE:
<221> NAME/KEY: misc_feature
<222> LOCATION: (11)..(11)
<223> OTHER INFORMATION: Xaa is Lys, N-methyl, Arg, Ser,Asp, or Pro.
<220> FEATURE:
<221> NAME/KEY: misc_feature
<222> LOCATION: (16)..(16)
<223> OTHER INFORMATION: Xaa is Arg, Lys, Tyr, Phe, Ser, Pro, Orn, Har,
      Har, p-amidinophenyl Ala, Ile, any other amino acid that has a
      positive charge other than Gly, or Try.

<400> SEQUENCE: 130

Lys Cys Phe Gly Lys Asn Asp Arg Xaa Lys Xaa Gln Ser Gly Leu Xaa
1               5                   10                  15

Cys Asn Ser Phe Lys Tyr
            20
```

```
<210> SEQ ID NO 131
<211> LENGTH: 40
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (12)..(12)
<223> OTHER INFORMATION: Xaa is BNP
<220> FEATURE:
<221> NAME/KEY: misc_feature
<222> LOCATION: (19)..(19)
<223> OTHER INFORMATION: Xaa is BNP
<220> FEATURE:
<221> NAME/KEY: misc_feature
<222> LOCATION: (26)..(26)
<223> OTHER INFORMATION: Xaa is BNP
<220> FEATURE:
<221> NAME/KEY: misc_feature
<222> LOCATION: (33)..(33)
<223> OTHER INFORMATION: Xaa is BNP
<220> FEATURE:
<221> NAME/KEY: misc_feature
<222> LOCATION: (40)..(40)
<223> OTHER INFORMATION: Xaa is BNP

<400> SEQUENCE: 131

His His His His His His Glu Gly Asp Arg Arg Xaa Arg Arg Asp Ala
1               5                   10                  15

Glu Asp Xaa Arg Arg Asp Ala Glu Asp Xaa Arg Arg Asp Ala Glu Asp
            20                  25                  30

Xaa Arg Arg Asp Ala Glu Asp Xaa
        35                  40

<210> SEQ ID NO 132
<211> LENGTH: 30
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (1)..(1)
<223> OTHER INFORMATION: Xaa is an amino acid or series of amino acids
      native to a natriuretic peptide.
<220> FEATURE:
<221> NAME/KEY: misc_feature
<222> LOCATION: (3)..(3)
<223> OTHER INFORMATION: Xaa3, Xaa14, Xaa27 are independently selected
      from the group consisting of Lys, Arg and Gly, and at least one
      of Xaa3, Xaa14, and Xaa27 is a Lys.
<220> FEATURE:
<221> NAME/KEY: misc_feature
<222> LOCATION: (14)..(14)
<223> OTHER INFORMATION: Xaa3, Xaa14, Xaa27 are independently selected
      from the group consisting of Lys, Arg and Gly, and at least one
      of Xaa3, Xaa14, and Xaa27 is a Lys.
<220> FEATURE:
<221> NAME/KEY: misc_feature
<222> LOCATION: (27)..(27)
<223> OTHER INFORMATION: Xaa3, Xaa14, Xaa27 are independently selected
      from the group consisting of Lys, Arg and Gly, and at least one
      of Xaa3, Xaa14, and Xaa27 is a Lys.

<400> SEQUENCE: 132

Xaa Pro Xaa Met Val Gln Gly Ser Gly Cys Phe Gly Arg Xaa Met Asp
1               5                   10                  15

Arg Ile Ser Ser Ser Ser Gly Leu Gly Cys Xaa Val Leu Arg
            20                  25                  30

<210> SEQ ID NO 133
```

```
<211> LENGTH: 17
<212> TYPE: PRT
<213> ORGANISM: Artificial Sequence
<220> FEATURE:
<223> OTHER INFORMATION: Natriuretic peptide
<220> FEATURE:
<221> NAME/KEY: DISULFID
<222> LOCATION: (1)..(17)
<220> FEATURE:
<221> NAME/KEY: misc_feature
<222> LOCATION: (5)..(5)
<223> OTHER INFORMATION: Xaa is Gly, Arg, or Lys.

<400> SEQUENCE: 133

Cys Phe Gly Arg Xaa Met Asp Arg Ile Ser Ser Ser Ser Gly Leu Gly
1               5                   10                  15

Cys

<210> SEQ ID NO 134
<211> LENGTH: 29
<212> TYPE: PRT
<213> ORGANISM: Artificial Sequence
<220> FEATURE:
<223> OTHER INFORMATION: Natriuretic peptide

<400> SEQUENCE: 134

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu
            20                  25

<210> SEQ ID NO 135
<211> LENGTH: 26
<212> TYPE: PRT
<213> ORGANISM: Artificial Sequence
<220> FEATURE:
<223> OTHER INFORMATION: Natriuretic peptide

<400> SEQUENCE: 135

Ser Pro Lys Met Val Gln Gly Ser Gly Cys Phe Gly Arg Lys Met Asp
1               5                   10                  15

Arg Ile Ser Ser Ser Ser Gly Leu Gly Cys
            20                  25

<210> SEQ ID NO 136
<211> LENGTH: 25
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (1)..(1)
<223> OTHER INFORMATION: Xaa1, Xaa12 and Xaa25 are each independently
      selected from the group consisting of Lys, Gly and Arg, with the
      proviso that at least one of Xaa1, Xaa12 and Xaa25 is Arg or Gly.
<220> FEATURE:
<221> NAME/KEY: misc_feature
<222> LOCATION: (12)..(12)
<223> OTHER INFORMATION: Xaa1, Xaa12 and Xaa25 are each independently
      selected from the group consisting of Lys, Gly and Arg, with the
      proviso that at least one of Xaa1, Xaa12 and Xaa25 is Arg or Gly.
<220> FEATURE:
<221> NAME/KEY: misc_feature
<222> LOCATION: (25)..(25)
<223> OTHER INFORMATION: Xaa1, Xaa12 and Xaa25 are each independently
      selected from the group consisting of Lys, Gly and Arg, with the
      proviso that at least one of Xaa1, Xaa12 and Xaa25 is Arg or Gly.

<400> SEQUENCE: 136
```

```
Xaa Met Val Gln Gly Ser Gly Cys Phe Gly Arg Xaa Met Asp Arg Ile
 1               5                  10                  15

Ser Ser Ser Ser Gly Leu Gly Cys Xaa
            20                  25
```

```
<210> SEQ ID NO 137
<211> LENGTH: 32
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (14)..(14)
<223> OTHER INFORMATION: Xaa14 is Lys and Xaa27 is other than Lys, or
      Xaa14 and Xaa27 are
      other than Lys. FEATURE:
<221> NAME/KEY: misc_feature
<222> LOCATION: (27)..(27)
<223> OTHER INFORMATION: Xaa14 is Lys and Xaa27 is other than Lys, or
      Xaa14 and Xaa27 are other than

<400> SEQUENCE: 137

Ser Pro Lys Met Val Gln Gly Ser Gly Cys Phe Gly Arg Xaa Met Asp
 1               5                  10                  15

Arg Ile Ser Ser Ser Ser Gly Leu Gly Cys Xaa Val Leu Arg Arg His
            20                  25
```

```
<210> SEQ ID NO 138
<211> LENGTH: 17
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (5)..(5)
<223> OTHER INFORMATION: Xaa5 is an amino acid that does not comprise a
      conjugation site.
<220> FEATURE:
<221> NAME/KEY: misc_feature
<222> LOCATION: (15)..(15)
<223> OTHER INFORMATION: Xaa15 is an amino acid that comprises a
      modifying moiety conjugation site.

<400> SEQUENCE: 138

Cys Phe Gly Arg Xaa Met Asp Arg Ile Ser Ser Ser Ser Gly Xaa Gly
 1               5                  10                  15

Cys
```

```
<210> SEQ ID NO 139
<211> LENGTH: 9
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (3)..(3)
<223> OTHER INFORMATION: Xaa comprises a modifying moiety conjugation
      site

<400> SEQUENCE: 139

Ser Pro Xaa Met Val Gln Gly Ser Gly
 1               5
```

```
<210> SEQ ID NO 140
<211> LENGTH: 6
```

```
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (1)..(1)
<223> OTHER INFORMATION: Xaa is an amino acid other than Lys.

<400> SEQUENCE: 140

Xaa Val Leu Arg Arg His
1               5

<210> SEQ ID NO 141
<211> LENGTH: 13
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (5)..(5)
<223> OTHER INFORMATION: Xaa is an amino acid other than Lys.

<400> SEQUENCE: 141

Cys Phe Gly Arg Xaa Met Asp Arg Ile Gly Leu Gly Cys
1               5                   10

<210> SEQ ID NO 142
<211> LENGTH: 17
<212> TYPE: PRT
<213> ORGANISM: Artificial Sequence
<220> FEATURE:
<223> OTHER INFORMATION: Natriuretic peptide
<220> FEATURE:
<221> NAME/KEY: misc_feature
<222> LOCATION: (5)..(5)
<223> OTHER INFORMATION: Xaa  is an amino acid other than lysine
<220> FEATURE:
<221> NAME/KEY: misc_feature
<222> LOCATION: (10)..(10)
<223> OTHER INFORMATION: Xaa  is any amino acid
<220> FEATURE:
<221> NAME/KEY: misc_feature
<222> LOCATION: (11)..(11)
<223> OTHER INFORMATION: Xaa  is any amino acid and may be absent or
     present
<220> FEATURE:
<221> NAME/KEY: misc_feature
<222> LOCATION: (12)..(12)
<223> OTHER INFORMATION: Xaa  is any amino acid and may be absent or
     present
<220> FEATURE:
<221> NAME/KEY: misc_feature
<222> LOCATION: (13)..(13)
<223> OTHER INFORMATION: Xaa  is any amino acid and may be absent or
     present

<400> SEQUENCE: 142

Cys Phe Gly Arg Xaa Met Asp Arg Ile Xaa Xaa Xaa Xaa Gly Leu Gly
1               5                   10                  15

Cys
```

What is claimed is:

1. A natriuretic compound conjugate comprising:
   (a) a biologically active natriuretic compound wherein the natriuretic compound comprises a brain natriuretic peptide (BNP) or a biologically active peptide segment of BNP that exhibits NPR-A receptor binding activity, and comprises:
   (i) a disulfide loop for binding to the NPR-A receptor; and
   (ii) at least one modifying moiety conjugation site; and
   (b) at least one modifying moiety attached to said modifying moiety conjugation site, wherein the modifying moiety conjugation site comprises a Lysine amino acid residue of BNP, wherein the modifying moiety comprises a polyalkylene glycol moiety "PAGn" moiety wherein the PAG moiety is a polyethylene glycol moiety and n is 1 to 8, and at least one of the following groups; a linking group "X" attached to the PAG moiety; an internal alkyl group "(—CH$_2$—)o" wherein o is 4 to 10;
wherein the modifying moiety is a formula:

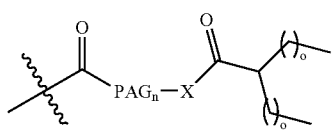

(Formula II)

wherein PAG is described above
X' is —O— or —N—; and
each o is described above wherein said natriuretic compound conjugate exhibits one or more advantages selected from the group consisting of increased resistance to enzymatic degradation relative to a corresponding unconjugated natriuretic compound, increased circulating half life, increased bioavailability, and prolonged duration of effect.

2. The natriuretic compound conjugate of claim 1 further defined as retaining a therapeutically significant percentage of cGMP stimulating activity relative to the corresponding unconjugated natriuretic compound wherein the therapeutically significant percentage of cGMP stimulating activity ranges from about 30 to about 90% activity.

3. The natriuretic compound conjugate of claim 1 further defined as more hydrophilic than a corresponding unconjugated natriuretic compound.

4. The natriuretic compound conjugate of claim 1 further defined as more amphiphilic than a corresponding unconjugated natriuretic compound.

5. The natriuretic compound conjugate of claim 1 further defined as more lipophilic than a corresponding unconjugated natriuretic compound.

6. The natriuretic compound conjugate of claim 1 wherein the natriuretic compound comprises a sequence:
A$^1$PX$^1$MVQGSGCFGRX$^2$MDRISSSSGLGCX$^3$VLR (SEQ ID NO. 132),
wherein
A$^1$ is an amino acid or series of amino acids native to a natriuretic peptide,
X$^1$, X$^2$ and X$^3$ are independently selected from the group consisting of Lys, Arg and Gly, and at least one of X$^1$, X$^2$ and X$^3$ is a Lys.

7. The natriuretic compound conjugate of claim 1 wherein the natriuretic compound comprises a brain natriuretic peptide of SEQ ID NO. 99.

8. The natriuretic compound conjugate of claim 1 wherein the natriuretic compound comprises:
a. an amino acid sequence
X$^1$—C$^1$FGRX$^2$MDRISSSSGLGC$^2$—X$^3$ (SEQ ID NO. 133),
wherein
X$^1$ is optionally present and when present is an amino acid sequence having from 1-10 amino acids;
X$^2$ is Gly, Arg, or Lys; and
X$^3$ is optionally present and when present is an amino acid sequence having from 1-10 amino acids;
b. a disulfide bond between C$^1$ and C$^2$ to form a loop.

9. The natriuretic compound conjugate of claim 8 wherein X$^1$ is Arg or Gly.

10. The natriuretic compound conjugate of claim 8 wherein X$^1$ is selected from the group consisting of:
a. Lys;
b. Gly;
c. Arg;
d. SG-, GSG-, QGSG-(SEQ ID NO. 23), VQGSG-(SEQ ID NO. 24), MVQGSG-(SEQ ID NO. 25), PKM-VQGSG-(SEQ ID NO. 27), and SPKMVQGSG-(SEQ ID NO. 28);
e. hBNP segments of d comprising a substitution selected from the group consisting of Lys-to-Gly and Lys-to-Arg;
f. hBNP segments of d comprising a substitution selected from the group consisting of Gly-to-Lys and Arg-to-Lys;
g. hBNP segments of d comprising an inserted Lys;
h. N-terminal tails and C-terminal segments of N-terminal tails of natriuretic peptides;
i. N-terminal tails and C-terminal segments of h comprising a substitution selected from the group consisting of Lys-to-Gly and Lys-to-Arg;
j. N-terminal tails and C-terminal segments of h comprising a substitution selected from the group consisting of Gly-to-Lys and Arg-to-Lys;
k. N-terminal tails and C-terminal segments of h comprising an inserted Lys.

11. The natriuretic compound conjugate of claim 8 wherein X$^3$ is selected from the group consisting of:
a. Lys;
b. Gly;
c. Arg;
d. hBNP segments Ky, KVL, KVLR (SEQ ID NO. 30), KVLRR (SEQ ID NO.31), and KVLRRH (SEQ ID NO. 32); and
e. hBNP segments of d comprising a substitution selected from the group consisting of Lys-to-Gly and Lys-to-Arg;
f. hBNP segments of d comprising a substitution selected from the group consisting of Gly-to-Lys and Arg-to-Lys;
g. hBNP segments of d comprising an inserted Lys;
h. C-terminal tails and N-terminal segments of C-terminal tails of natriuretic peptides;
i. C-terminal tails and N-terminal segments of C-terminal tails of h comprising a substitution selected from the group consisting of Lys-to-Gly and Lys-to-Arg;
j. C-terminal tails and N-terminal segments of C-terminal tails of h comprising a substitution selected from the group consisting of Gly-to-Lys and Arg-to-Lys;
k. C-terminal tails and N-terminal segments of C-terminal tails of h comprising an inserted Lys.

12. The natriuretic compound conjugate of claim 8 wherein the natriuretic compound comprises a sequence selected from the group consisting of:
a. SPKMVQGSGCCFGRKMDRISSSSGLGCKVL (SEQ ID NO. 134);
b. SPKMVQGSGCFGRKMDRISSSSGLGC (SEQ ID NO. 135); and
c. segments a or b comprising a substitution selected from the group consisting of Lys-to-Gly and Lys-to-Arg.

13. The natriuretic compound conjugate of claim 8 wherein X$^1$ comprises a 1-9 amino acid residue sequence from the N-terminus of hBNP.

14. The natriuretic compound conjugate of claim 8 wherein X$^1$ comprises SPX$^3$MVQGSG (SEQ ID NO.6), and wherein X$^2$ comprises a modifying moiety conjugation site.

15. The natriuretic compound conjugate of claim 8 wherein X$^3$ comprises a 1-6 amino acid residue sequence from the C-terminus of hBNP.

16. The natriuretic compound conjugate of claim 8 wherein X$^3$ comprises KVLRRH (SEQ. ID. NO. 32), KVLRR (SEQ ID NO. 31), KVLR (SEQ ID NO. 30), KVL, KV or K.

17. The natriuretic compound conjugate of claim 1 wherein the natriuretic compound comprises a native hBNP sequence having one or more mutations selected from the group consisting of Lys3Arg, Lys14Arg, Arg30Lys, Lys27Arg, and Arg31Lys.

18. The natriuretic compound conjugate of claim 1 wherein the natriuretic compound comprises a native hBNP sequence, having one or more insertions or deletions.

19. The natriuretic compound conjugate of claim 1 wherein the natriuretic compound comprises a native hBNP amino acid sequence and a N-terminal or C-terminal Lys.

20. The natriuretic compound conjugate of claim 1 further defined as:
   a. comprising a multipeptide comprising two or more amino acid sequences encoding a natriuretic compound;
   b. optionally comprising a spacer sequence between each set or adjacent natriuretic compound encoding sequences;
   c. optionally comprising an extension at either or both ends of the multipeptide, the extension comprising one or more amino acids.

21. The natriuretic compound conjugate of claim 20 wherein the at least one modifying moiety conjugation site is a Lys.

22. The natriuretic compound conjugate of claim 1 wherein the natriuretic compound consists of a native BNP.

23. The natriuretic compound conjugate of claim 1 wherein the natriuretic compound consists of a native hBNP.

24. The natriuretic compound conjugate of claim 1 wherein the internal amino acid residue is Lys3, Lys 14 or Lys 28.

25. The natriuretic compound conjugate of claim 1 wherein the natriuretic compound consists of a canine BNP.

26. The natriuretic compound conjugate of claim 1 wherein the natriuretic compound consists of urodilatin.

27. The natriuretic compound conjugate of claim 1 wherein the natriuretic compound consists of DNP.

28. The natriuretic compound conjugate of claim 1 wherein the natriuretic compound comprises the amino acid sequence Des His32, Des Arg31 hBNP.

29. The natriuretic compound conjugate of claim 1 wherein the natriuretic compound comprises an amino acid sequence:
   X$^1$MVQGSGCFGRX$^2$MDRISSSSGLGCX$^3$ (SEQ ID NO. 136),
   wherein X$^1$, X$^2$ and X$^3$ are each independently selected from the group consisting of Lys, Gly and Arg, with the proviso that at least one of X$^1$, X$^2$ and X$^3$ is Arg or Gly.

30. The natriuretic compound conjugate of claim 29 wherein the sequence comprises:
   a. N-terminal to X$^1$, an extension selected from the group consisting of: SPK, PK and K; and/or
   b. C-terminal to X$^3$, an extension selected from the group consisting of -VLRRH (SEQ ID NO. 19), -VLRR (SEQ ID NO. 20), -VLR, -VL, and -V.

31. The natriuretic compound conjugate of claim 29 wherein X$^1$ is Lys, X$^2$ is Arg and X$^3$ is Arg.

32. The natriuretic compound conjugate of claim 1 wherein the natriuretic compound comprises an amino acid sequence: CFGRX$^1$MDRISSSSGLGCX$^2$ (SEQ ID NO. 21),
   wherein X$^1$ and/or X$^2$ comprises a modifying moiety conjugation site coupled to the modifying moiety.

33. The natriuretic compound conjugate of claim 32 wherein X$^1$ comprises Lys coupled to the modifying moiety.

34. The natriuretic compound conjugate of claim 32 wherein X$^2$ comprises Lys coupled to the modifying moiety.

35. The natriuretic compound conjugate of claim 1 wherein the modifying moiety conjugation site comprises a moiety selected from the group consisting of an N-terminus of the natriuretic compound, and a C-terminus of the natriuretic compound.

36. The natriuretic compound conjugate of claim 1 wherein the natriuretic compound conjugate includes only one modifying moiety.

37. The natriuretic compound conjugate of claim 1 wherein:
   a. the natriuretic compound comprises a Lys$^3$ to Cys$^{26}$ segment of hBNP and a disulfide bond coupling Cys$^{10}$ of the segment to the Cys$^{26}$;
   b. a single modifying moiety coupled to the natriuretic compound at the Lys$^3$.

38. The natriuretic compound conjugate of claim 1 wherein the natriuretic compound comprises a Cys$^{10}$ to Cys$^{26}$ segment of hBNP and a disulfide bond coupling the Cys$^{10}$ to the Cys$^{26}$, wherein said natriuretic compound is a monoconjugate including a single modifying moiety coupled thereto at Lys$^{14}$ of the segment.

39. The natriuretic compound conjugate of claim 1 wherein the natriuretic compound comprises a Cys$^{10}$ to Lys$^{27}$ segment of hBNP, wherein said natriuretic compound is a monoconjugate including a single modifying moiety coupled thereto at Lys$^{27}$ of the segment.

40. The natriuretic compound conjugate of claim 1 wherein the natriuretic compound comprises a Cys$^{10}$ to His$^{32}$ segment of hBNP and a disulfide bond coupling the Cys$^{10}$ to Cys$^{26}$ of the segment, wherein said natriuretic compound is a monoconjugate including a single modifying moiety coupled thereto at Lys$^{27}$ of the segment.

41. The natriuretic compound conjugate of claim 1 wherein:
   a. the natriuretic compound consists of the hBNP amino acid sequence; and
   b. the natriuretic compound conjugate is a diconjugate comprising:
      i. a modifying moiety coupled to the natriuretic peptide at Lys$^3$ of the hBNP amino acid sequence; and
      ii. a modifying moiety coupled to the natriuretic peptide at Lys$^{14}$ of the hBNP amino acid sequence.

42. The natriuretic compound conjugate of claim 1 wherein:
   a. the natriuretic compound is hBNP; and
   b. the natriuretic compound conjugate is a diconjugate comprising:
      i. a modifying moiety coupled to the natriuretic peptide at Lys$^3$ of the hBNP amino acid sequence; and
      ii. a modifying moiety coupled to the natriuretic peptide at Lys27 of the hBNP amino acid sequence.

43. The natriuretic compound conjugate of claim 1 wherein the natriuretic compound sequence comprises an N-terminal tail and the modifying moiety is coupled to an amino acid which is positioned in the N-terminal tail.

44. The natriuretic compound conjugate of claim 43 wherein the N-terminal tail consists of a native sequence of an N-terminal tail of a natriuretic peptide or a C-terminal segment of an N-terminal tail of a natriuretic peptide.

45. The natriuretic compound conjugate of claim 1 wherein the modifying moiety is coupled to the natriuretic compound by a bond that is hydrolysable in vivo.

46. The natriuretic compound conjugate of claim 1 wherein the modifying moiety is coupled to the natriuretic compound by a bond that is hydrolysable in the bloodstream.

47. The natriuretic compound conjugate of claim 1 wherein the modifying moiety is coupled to the natriuretic compound by a bond that is not hydrolysable in vivo.

48. The natriuretic compound conjugate of claim 1 wherein the modifying moiety is coupled to the natriuretic compound by a bond that is not hydrolysable in the bloodstream.

49. The natriuretic compound conjugate of claim 1 wherein the modifying moiety is coupled to the natriuretic compound by a bond selected from the group consisting of ester, carbonate, carbamate, amide, ether, and amine.

50. The natriuretic compound conjugate of claim 1 wherein the modifying moiety is hydrolysable in vivo to yield a PAGylated natriuretic compound.

51. The natriuretic compound conjugate of claim 1 wherein the modifying moiety is hydrolysable in vivo to yield a PAGylated natriuretic compound comprising one or more PAG moieties having 1, 2, 3, 4, 5, or 6 PAG units.

52. A pharmaceutical formulation comprising the natriuretic compound conjugate of claim 1.

53. The pharmaceutical formulation of claim 52 formulated for a route of delivery selected from the group consisting of enteral, parenteral, oral, subcutaneous, sublingual, buccal, nasal, pulmonary, intravenous and intramuscular.

54. A method of treating a condition characterized by an excessive level of extracellular fluid, the method comprising administering to a subject in need thereof a pharmaceutically acceptable amount of the BNP natriuretic compound conjugate of claim 1.

55. The method of claim 54 wherein the condition comprises congestive heart failure.

56. The method of claim 54 wherein the condition comprises chronic congestive heart failure.

57. The method of claim 54 wherein the condition comprises acute congestive heart failure.

58. The method of claim 54 wherein the natriuretic compound conjugate is self administered.

59. The method of claim 54 wherein the natriuretic compound conjugate is orally administered.

60. The method of claim 54 wherein the natriuretic compound conjugate is administered via a route of administration selected from the group consisting of enteral, parenteral, oral, subcutaneous, sublingual, buccal, nasal, pulmonary, intravenous and intramuscular.

61. The method of claim 54 wherein the condition is hypertension.

* * * * *

UNITED STATES PATENT AND TRADEMARK OFFICE
CERTIFICATE OF CORRECTION

PATENT NO.      : 7,648,962 B2                                              Page 1 of 1
APPLICATION NO. : 10/999761
DATED           : January 19, 2010
INVENTOR(S)     : James et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 67 days.

Signed and Sealed this

Twenty-third Day of November, 2010

David J. Kappos
*Director of the United States Patent and Trademark Office*